US011352628B2

(12) United States Patent
Minomi et al.

(10) Patent No.: US 11,352,628 B2
(45) Date of Patent: *Jun. 7, 2022

(54) METHODS AND COMPOSITIONS FOR TREATING MALIGNANT TUMORS ASSOCIATED WITH KRAS MUTATION

(71) Applicant: Nitto Denko Corporation, Osaka (JP)

(72) Inventors: Kenjirou Minomi, Osaka (JP); Jihua Liu, San Marcos, CA (US); Li Wang, San Diego, CA (US); Bharat Majeti, San Diego, CA (US); Roger Adami, Carlsbad, CA (US); Wenbin Ying, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/540,973

(22) Filed: Aug. 14, 2019

(65) Prior Publication Data

US 2019/0367926 A1 Dec. 5, 2019

Related U.S. Application Data

(60) Division of application No. 15/636,528, filed on Jun. 28, 2017, now abandoned, which is a continuation-in-part of application No. 15/434,318, filed on Feb. 16, 2017, now Pat. No. 10,792,299, which is a continuation-in-part of application No. 14/979,573, filed on Dec. 28, 2015, now Pat. No. 9,580,710.

(60) Provisional application No. 62/266,672, filed on Dec. 13, 2015, provisional application No. 62/184,204, filed on Jun. 24, 2015.

(30) Foreign Application Priority Data

Dec. 26, 2014 (JP) ................................ 2014-266198

(51) Int. Cl.
C12N 15/113 (2010.01)
A61K 31/713 (2006.01)
A61K 31/7105 (2006.01)
A61K 9/127 (2006.01)

(52) U.S. Cl.
CPC .......... *C12N 15/1137* (2013.01); *A61K 9/127* (2013.01); *A61K 31/713* (2013.01); *A61K 31/7105* (2013.01); *C12N 15/113* (2013.01); *C12N 15/1135* (2013.01); *C12Y 205/01018* (2013.01); *C12N 2310/14* (2013.01); *C12N 2310/321* (2013.01); *C12N 2310/322* (2013.01); *C12N 2310/344* (2013.01); *C12N 2310/531* (2013.01); *C12N 2320/32* (2013.01)

(58) Field of Classification Search
CPC ............ C12N 15/1137; C12N 2310/14; C12N 2320/32; C12N 2310/322; A61K 31/713
See application file for complete search history.

(56) References Cited

U.S. PATENT DOCUMENTS

| 5,968,737 A | 10/1999 | Ali-Osman |
| 7,056,704 B2 | 6/2006 | Tuschl et al. |
| 7,605,251 B2 | 10/2009 | Tan et al. |
| 8,067,390 B2 | 11/2011 | Merritt |
| 8,101,741 B2 | 1/2012 | MacLachlan et al. |
| 8,367,628 B2 | 2/2013 | Goodwin |
| 8,603,995 B2 | 12/2013 | Labow et al. |
| 8,664,376 B2 | 3/2014 | Niitsu |
| 8,686,052 B2 | 4/2014 | Niitsu |
| 8,710,209 B2 | 4/2014 | Jin |
| 8,741,867 B2 | 6/2014 | Niitsu |
| 8,895,717 B2 | 11/2014 | Sood |
| 9,151,758 B2 | 10/2015 | Zetter |
| 9,206,424 B2 | 12/2015 | Jin |
| 9,580,710 B2 | 2/2017 | Minomi et al. |
| 9,771,582 B2 * | 9/2017 | Niitsu .................. C07F 9/6533 |
| 10,047,110 B2 | 8/2018 | Minomi et al. |
| 10,047,111 B2 | 8/2018 | Minomi et al. |
| 10,792,299 B2 | 10/2020 | Minomi et al. |
| 2004/0219600 A1 | 11/2004 | Williams, III |
| 2005/0255487 A1 | 11/2005 | Khvorova |
| 2007/0083334 A1 | 4/2007 | Mintz |
| 2007/0083945 A1 | 4/2007 | Byrum |
| 2009/0181379 A1 | 7/2009 | Corrales Izquierdo et al. |
| 2009/0220956 A1 | 9/2009 | Nuyten |
| 2010/0196482 A1 | 8/2010 | Radovic-Moreno et al. |

(Continued)

FOREIGN PATENT DOCUMENTS

| CA | 3028934 | 12/2017 |
| CN | 103619355 A | 3/2014 |

(Continued)

OTHER PUBLICATIONS

The Human Protein Atlas, retrieved from https://www.proteinatlas.org/ENSG00000133703-KRAS/tissue on Aug. 26, 2020 (Year: 2020).*
Machine translation of WO 2012176282 (Year: 2012).*
Riely (Clin Cancer Res 2008;14(5731 18) Sep. 15, 2008) (Year: 2008).*
Bayrak et al (Journal of Kidney Cancer and VHL 2014; 1(4):40-45) (Year: 2014).*
Kim (Experimental & Molecular Medicine (2015) 47, e137; doi:10.1038/emm.2014.99, 9 pages) (Year: 2015).*
Taylor et al. (Cancer Cell 18, 11-22, Jul. 13, 2010) (Year: 2010).*
Shigaki et al (Ann Surg Oncol (2013) 20:S485-S491) (Year: 2013).*
Turhal et al (Molecular and Clinical Oncology 3: 1275-1279, 2015) (Year: 2015).*

(Continued)

*Primary Examiner* — Richard A Schnizer
(74) *Attorney, Agent, or Firm* — Knobbe, Martens, Olson & Bear, LLP

(57) ABSTRACT

This invention provides methods and compositions for preventing, treating or ameliorating one or more symptoms of a malignant tumor, which may be associated with KRAS mutation in a mammal in need thereof, by administering to the mammal a therapeutically effective amount of a composition comprising one or more RNAi molecules that are active in reducing expression of GST-π.

20 Claims, 16 Drawing Sheets

Specification includes a Sequence Listing.

(56) References Cited

U.S. PATENT DOCUMENTS

| | | |
|---|---|---|
| 2013/0028885 A1 | 1/2013 | Zetter et al. |
| 2013/0052160 A1 | 2/2013 | Zitvogel |
| 2013/0053270 A1 | 2/2013 | Gill |
| 2013/0330401 A1 | 12/2013 | Payne et al. |
| 2013/0345286 A1 | 12/2013 | Gollob et al. |
| 2014/0134158 A1 | 5/2014 | Bardelli |
| 2014/0303237 A1 | 10/2014 | Shapiro et al. |
| 2014/0315975 A1 | 10/2014 | Niitsu et al. |
| 2014/0315976 A1 | 10/2014 | Brahmbhatt et al. |
| 2015/0328248 A1 | 11/2015 | Niitsu et al. |
| 2016/0186182 A1 | 6/2016 | Niitsu et al. |
| 2016/0186183 A1 | 6/2016 | Minomi et al. |
| 2016/0187319 A1 | 6/2016 | Tanaka |
| 2018/0002702 A1 | 1/2018 | Minomi et al. |

FOREIGN PATENT DOCUMENTS

| | | |
|---|---|---|
| EP | 2724729 | 4/2014 |
| EP | 2937099 | 10/2015 |
| JP | 2009-513151 A | 4/2009 |
| JP | 2009-536827 A | 10/2009 |
| JP | 2013-212113 A | 10/2013 |
| JP | 2017-014185 A | 1/2017 |
| JP | 2017-226626 A | 12/2017 |
| WO | WO 1998/021359 | 5/1998 |
| WO | WO 2004/094636 | 11/2004 |
| WO | WO 2007/061922 | 5/2007 |
| WO | WO 2012/176282 | 12/2012 |
| WO | WO 2013/075140 | 5/2013 |
| WO | WO 2013/192364 | 12/2013 |
| WO | WO 2014/098210 | 6/2014 |
| WO | WO 2014/136086 | 9/2014 |
| WO | WO 2016/106400 | 6/2016 |
| WO | WO 2016/106404 | 6/2016 |
| WO | WO 2016/106405 | 6/2016 |
| WO | WO 2016/106406 | 6/2016 |

OTHER PUBLICATIONS

Chen et al. (PLoS ONE, 9(5):e98293, 16 pages, 2014) (Year: 2014).*

Adler et.al, Regulation of JNK signaling by GSTp. EMBO J. 1999, 18, 1321-1334.

Bakker et al., Methyl-CpG binding domain protein 2 represses transcription from hypermethylated pi-class glutathione S-transferase gene promoters in hepatocellular carcinoma cells, J Biol Chem. 2002, vol. 277, Issue 25, pp. 22573-22580.

Ban et al., Transfection of Glutathione S-Transferase {GST}-π Antisense Complementary DNA Increases the Sensitivity of Colon Cancer Cell Line to Adriamycin, Cisplatin, Melphalan, and Etoposide, Cancer Res., Aug. 1, 1996, vol. 56, 3577-3582.

Birkeland et al., KRAS gene amplification and overexpression but not mutation associates with aggressive and metastatic endometrial cancer, 2012, Br J Cancer, vol. 107, pp. 1997-2004.

Cansar, Institute of Cancer Research; https://cansar.icr.ac.uk/cansar/cell-lines/A549/mutations/; retrieved online on Jun. 20, 2016.

Collins et al., KRAS as a key oncogene and therapeutic target in pancreatic cancer, Front Physiol. 2013, vol. 4, Article 107, pp. 1-8.

Esteller et al., Inactivation of Glutathione S-Transferase P1 Gene by Promoter Hypermethylation in Human Neoplasia, Cancer Res. 1998, vol. 58, pp. 4515-4518.

Futreal et al., A Census of Human Cancer Genes, Nature Reviews Cancer 2004, vol. 4, pp. 177-183.

GenBank Accession No. AC230665, Bos taurus clone CH240-502B15, Jul. 10, 2008 [online]. [Retrieved on May 1, 2016]. Retrieved from the internet <URL:http://www.ncbi.nlm.nih.gov/nuccore/AC230665>.

GenBank Accession No. AC114115, Rattus norvegicus clone CH230-2808, Working Draft Sequence, 6 unordered pieces, May 13, 2003 [online]. [Retrieved on Apr. 30, 2016). Retrieved from the internet <URL: http://www.ncbi.nlm.nih.gov/nuccore/AC114115>.

GenBank Accession No. AC230574, Bos taurus clone CH240-504M17, Jul. 10, 2008 [online]. [Retrieved Jn May 1, 2016]. Retrieved from the internet <URL:http://www.ncbi.nlm.nih.gov/nuccore/AC230574>.

GenBank Accession No. AW374759, MR1-CT005B-291199-003-a05 CT0058 Homo sapiens cDNA. rnRNA sequence, Jan. 9, 2011 [online]. {Retrieved on May 1, 2016). Retrieved from the internet <URL: http://www. cbi.nlm.nih.gov/nucesl/6B79413/>.

GenBank Accession No. BV207757, sqnm2244B3 Human DNA {Sequenom} Homo sapiens STS genomic, Oct. 17, 2009 [online]. [Retrieved on May 1, 2016]. Retrieved from the internet <URL: http://www.ncbi.nlm.nih.gov/ uccore/BV207757>.

GenBank Accession No. G0761423, 0010260TNA004657HT OTNA Ovis aries cDNA 5-, mRNA sequence g May 2009 [online]. [Retrieved on Apr. 30, 2016]. Retrieved from the internet <URL: http://www.ncbi.nlm.nih.gov/ ucest/G0761423>.

GenBank Accession No. G0786145, 0009200TNA002813HT OTNA Ovis aries cDNA 5-,.mRNA sequence May 6, 2009 [online). [Retrieved on Apr. 30, 2016]. Retrieved from the internet <URL: http://www.ncbi.nlm.nih.gov/ ucest/G0786145>.

GenBank Accession No. JU528663, TSA: Ctenomys sociabilis 330326.Ctso mRNA sequence, Oct. 10, 2012 [online].[Retrieved on Apr. 30, 2016). Retrieved from the internet <URL: http://www.ncbi.nlm.nih.gov/nuccore/ JU528663>.

Hayashi et al., Suppressive effect of sulindac on branch duct-intraductal papillary mucinous neoplasms, J Gastroenterol., 2009, vol. 44, pp. 964-975.

Hida et al., Serum Glutathione S-Transferase-π Level as a Tumor Marker for Non-Small Cell Lung Cancer—Potential predictive value in chemotherapeutic resonse, Cancer, Mar. 1, 1994, vol. 73, No. 5, pp. 1377-1382.

Hirata et al., Significance of Glutathione S-Transferase-π as a Tumor Marker in Patients with Oral Cancer, Cancer, Nov. 15, 1992, vol. 70, No. 10, pp. 2381-2387.

Hokaiwado, Glutathione S-transferase Pi mediates proliferation of androgen-independent prostate cancer cells, Carcinogenesis, Apr. 15, 2008, vol. 29, pp. 1134-1138.

Jackson et al., Expression profiling reveals off-target gene regulation by RNAi, 2003, Nature Biotechnology, vol. 21, pp. 535-637.

Jankova et al., Glutathione S-transferase Pi expression predicts response to adjuvant chemotherapy for stage C colon cancer: a matched historical control study, BMC Cancer, 2012, vol. 12, 196.

Jin et al., shRNA-mediated GSTP1 gene silencing enhances androgen-independent cell line DU145 chemosensitivity, Int Urol Nephrol. 2014, 46(6):1115-1121.

Love et al., Lipid-like materials for low-dose, in vivo gene silencing, Proc Natl Acad Sci U S A., 2010, vol. 107(5):1864-1869.

Matsunaga et al., C(H)OP refractory chronic lymphocytic leukemia patients in whom salvage chemotherapy chosen by evaluating multiple chemotherapeutic drug-resistant factors was remarkably effective, Int J Clin Oncol, 2003, vol. 8, pp. 326-331.

Miyanishi et al., Glutathione S-transferase-pi overexpression is closely associated with K-ras mutation during human colon carcinogenesis, Gastroenterology, 2001, vol. 121, pp. 865-874.

Morgan et al., Tumor Efficacy and Bone Marrow-sparing Properties of TER286, a Cytotoxin Activated by Glutathione S-Transferase, Cancer Res., Jun. 15. 1998, vol. 58, pp. 2568-2575.

Morrow et al, Structure of the human genomic glutathione S-transferase-π gene, Gene (1989) 75:3-11.

Morse M.A., The role of glutathione S-transferase P1-1 in colorectal cancer: friend or foe?, Gastroenterology, 2001, vol. 121 (4), pp. 1010-1013.

Müller et al., Thiazolides inhibit growth and induce glutathione-S-transferase Pi {GSTP1 )-dependent cell death in human colon cancer cells, 2008, Int. J_ Cancer, vol. 123, pp. 1797-1806.

Nakajima et al., Reversal of multiple drug resistance in cholangiocarcinoma by the glutathione S-transferase-pi-specific inhibitor O1-hexadecyl-gamma-glutamyl-S-benzylcysteinyl-D-phenylglycine ethylester. J Pharmacol Exp Ther. 2003; 306 (3): 861-869.

(56) References Cited

OTHER PUBLICATIONS

Niitsu et al., A proof of glutathione S-transferase-pi-related multidrug resistance by transfer of antisense gene to cancer cells and sense gene to bone marrow stem cell, Chem Biol Interact., 1998, vol. 111-112, pp. 325-332.

Niitsu et al., Serum Glutathione-S- Transferase-π as a Tumor Marker for Gastrointestinal Malignancies, Cancer, Jan. 15, 1989, vol. 63, pp. 317-323.

Nishita et al., Regulation of autophagy and MAPK signaling b) Jlutathione S-transferase Pi in KRAS mutated cancer cells, AACR 102nd Annual Meeting, 2011; Abstract No. 1065.

Patel et al., Rescue of paclitaxel sensitivity by repression of Prohibitin1 in drug-resistant cancer cells, PNAS Feb. 9, 2010, vol. 107, No. 6, pp. 2503-2508.

Petrini et al., GST-π and P-170 co-expression in multiple myeloma, Br J Haematol. 1995, vol. 90, Issue 2, pp. 393-397.

Qazilbash et al., Risk Factors for relapse after complete remission with high-dose therapy for multiple myeloma, Leuk Lymphoma. 2006, vol. 47, Issue 7, pp. 1360-1364.

Ruan et al., Analysis of EGFR signaling pathway in nasopharyngeal carcinoma cells by quantitative phosphoproteomics, Proteome Sci., Jun. 28, 2011, vol. 9, 35, in 11 pages.

Sawers, Glutathione S-transferase Pi {GSTP1) directly influences platinum drug chemosensitivity in ovarian tumour cell lines, British Journal of Cancer, 2014, 111(6):1150-1158.

Singhal et al., 1,3-bis(3,5-dichlorophenyl) Urea Compound 'COH-SR4' Inhibits Proliferation and Activates Apoptosis in Melanoma, Biochem Pharmacol., Dec. 1, 2012, vol. 84, Issue 11, pp. 1419-1427.

Steckel et al., Determination of synthetic lethal interactions in KRAS oncogene-dependent cancer cells reveals novel therapeutic targeting strategies, Cell Res. 2012, vol. 22(8), pp. 1227-1245.

Takahashi et al., [Glutathione S transferases-π], Article in Japanes; Gan To Kagaku Ryoho. 1994; 21 (7): 945-51, English summary p. 951.

Townsend et. al., Novel Role for Glutathione S-Transferase π—Regulator of Protein S-Glutathionylation Following Oxidative and Nitrosative Stress. J Biol Chem. 2009, vol. 284, 436-445.

Ui-Tei et al., Functional dissection of siRNA sequence by systematic DNA substitution: modified siRNA with a DNA seed arm is a powerful tool for mammalian gene silencing with significantly reduced off-target effect, Nucleic Acids Res., 2008, vol. 36(7), pp. 2136-2151.

Vaishnaw, Review A status report on RNAi therapeutics, Silence, Dec. 31, 2010, vol. 1, pp. 14-26.

Valtorta et al., KRAS gene amplification in colorectal cancer and impact on response to EGFR-targeted therapy, 2013, Int J Cancer, vol. 133, pp. 1259-1266.

Wagner et al., In Situ Evidence of KRAS Amplification and Association With Increased p21 Levels in Non-Small Cell Lung Carcinoma, 2009, Am J Clin Pathol, vol. 132, pp. 500-505.

Wang et al., Decreased expression of GST pi is correlated with a porr prognosis in human esophageal squamous carcinoma, BMC Cancer. 2010, vol. 10, 352.

Xu et al., Enhancing tumor cell response to chemotherapy through nanoparticle-mediated codelivery of siRNA and cisplatin prodrug, Proc Natl Acad Sci U S A, 2013, vol. 110, No. 46, pp. 18638-18643.

Xue et al., Small RNA combination therapy for lung cancer, Proc Natl Acad Sci U SA, 2014, vol. 111(34), pp. E3553-E3561.

Yin et.al, Glutathione S-transferase p elicits protection against H2O2-induced cell death via coordinated regulation of stress kinases. Cancer Res. 2000, vol. 60, 4053-4057.

International Search Report dated Aug. 30, 2018 for PCT International Application No. PCT/US2018/000054.

Chinese Office Action dated Mar. 25, 2019 for CN Application No. 201580071232.9.

Japanese Office Action dated Feb. 19, 2019 for JP Application 2018-535394.

Japanese Office Action dated Feb. 19, 2019 for JP Application 2018-134423.

Nagaprashantha et al., 2'-hydroxyflavanone inhibits proliferation, tumor vascularization and promotes normal differentiation in VHL-mutant renal cell carcinoma. Carcinogenesis. 2011. 32(4):568-575.

Noguchi et al., PI3K-AKT Network Roles in Infectious Diseases, J Infect Diseases. 2008. 82(3):161-167.

Tripathi, et al., Reactive nitrogen species regulate autophagy through ATM-AMPK-TSC2-mediated suppression of mTORC1. Proc Natl Acad Sci USA, 2013. 110(32):E2950-2957.

Japanese Office Action dated Oct. 15, 2019 for JP Application 2015-247725.

Extended European Search Report dated May 16, 2018 for ER Application No. 15874365.8.

Office Action issued in JP Application No. 2018-535394, dated Feb. 19, 2019.

Office Action issued in JP Application No. 2018-134423, dated Feb. 19, 2019.

Office Action issued in AU Application No. 2015369596, dated May 18, 2020.

Office Action issued in CN Application No. 201580071232.9, dated Mar. 25, 2019.

Office Action issued in CN Application No. 201580071232.9, dated Dec. 27, 2019.

Office Action issued is U.S. Appl. No. 15/434,318, dated Feb. 21, 2019.

Office Action issued in U.S. Appl. No. 15/434,318, dated May 31, 2019.

Office Action issued in U.S. Appl. No. 15/434,318, dated Jan. 10, 2020.

Office Action issued in U.S. Appl. No. 15/636,528, dated Mar. 15, 2019.

Office Action issued in U.S. Appl. No. 16/804,696, dated Oct. 8, 2021.

* cited by examiner

METHODS AND COMPOSITIONS FOR TREATING MALIGNANT TUMORS ASSOCIATED WITH KRAS MUTATION

SEQUENCE LISTING

This application includes a Sequence Listing submitted electronically as an ASCII file created on Aug. 14, 2019, named HRAK001.008P2D1_SL.txt, which is 127 KB in size, and is hereby incorporated by reference in its entirety.

BACKGROUND OF THE INVENTION

Glutathione S-transferases (IUBMB EC 2.5.1.18) are a family of enzymes that play an important role in detoxification by catalyzing the conjugation of many hydrophobic and electrophilic compounds with reduced glutathione. Based on their biochemical, immunologic, and structural properties, the soluble GSTs are categorized into four main classes: alpha, mu, pi, and theta. Some of these forms are suggested to act to prevent carcinogenesis by detoxifying proximate or ultimate carcinogens, especially electrophilic agents including Michael reaction acceptors, diphenols, quinones, isothiocyanates, peroxides, vicinal dimercaptans, etc. However, in neoplastic cells, specific forms are known to be expressed and have been known to participate in their resistance to anticancer drugs.

The glutathione S-transferase-π gene (GSTP1) is a polymorphic gene encoding active, functionally different GSTP1 variant proteins that are thought to function in xenobiotic metabolism and play a role in susceptibility to cancer. It is expressed abundantly in tumor cells. See, e.g., Aliya S. et al. Mol Cell Biochem., 2003 November; 253(1-2):319-327. Glutathione S-transferase-P is an enzyme that in humans is encoded by the GSTP1 gene. See, e.g., Bora P S, et al. (October 1991) J. Biol. Chem., 266 (25): 16774-16777. The GST-π isoenzyme has been shown to catalyze the conjugation of GSH with some alkylating anti-cancer agents, suggesting that over-expression of GST-π would result in tumor cell resistance.

Elevated serum GST-π levels were observed in patients with various gastrointestinal malignancies including gastric, esophageal, colonic, pancreatic, hepatocellular, and biliary tract cancers. Patients with benign gastrointestinal diseases had normal GST-π, but some patients with chronic hepatitis and cirrhosis had slightly elevated levels. Over 80% of patients with Stage III or IV gastric cancer and even about 50% of those with Stage I and II had elevated serum GST-π. See, e.g., Niitsu Y, et al. Cancer, 1989 Jan. 15; 63(2):317-23. Elevated GST-π levels in plasma were observed in patients with oral cancer, but patients with benign oral diseases had normal GST-π levels. GST-π was found to be a useful marker for evaluating the response to chemotherapy, for monitoring postoperative tumor resectability or tumor burden, and for predicting the recurrence of tumor in patients with oral cancer. See, e.g., Hirata S. et al. Cancer, 1992 Nov. 15;70(10):2381-7.

Immunohistochemical studies have revealed that many cancers, histologically classified as adenocarcinomas or squamous cell carcinomas, express GST-π. Plasma or serum GST-π levels are increased in 30-50% of patients with cancers of the gastrointestinal tract. This form is also suggested to participate in resistance to anticancer drugs such as cisplatin and daunorubicin, and its expression in cancer tissues may be of prognostic value in cancer patients.

The protein product of the normal human KRAS gene (V-Ki-ras2 Kirsten rat sarcoma viral oncogene homolog) performs a signaling function in normal tissue, and the mutation of a KRAS gene is a putative step in the development of many cancers. See, e.g. Kranenburg O, November 2005, Biochim. Biophys. Acta, 1756(2):81-82. The KRAS protein is a GTPase and is involved in several signal transduction pathways. KRAS acts as a molecular on/off switch which activates proteins necessary for the propagation of growth factor and signals of other receptors such as c-Raf and PI 3-kinase.

Mutation in KRAS can be related to malignant tumors, such as lung adenocarcinoma, mucinous adenoma, ductal carcinoma of the pancreas, and colorectal carcinoma. In human colorectal cancer, KRAS mutation appears to induce overexpression of GST-π via activation of AP-1. See, e.g., Miyanishi et al., Gastroenterology, 2001; 121 (4):865-74.

Mutant KRAS is found in colon cancer (Burmer G C, Loeb L A, 1989, Proc. Natl. Acad. Sci. U.S.A., 86(7):2403-2407), pancreatic cancer (Almoguera C, et al., 1988, Cell, 53(4):549-554) and lung cancer (Tam I Y, et al., 2006, Clin. Cancer Res., 12(5):1647-1653). KRAS accounts for 90% of RAS mutations in lung adenocarcinomas (Forbes S, et al. Cosmic 2005. Br J Cancer, 2006; 94:318-322).

KRAS gene may also be amplified in colorectal cancer. KRAS amplification can be mutually exclusive with KRAS mutations. See, e.g., Valtorta E, et al., 2013, Int. J. Cancer, 133(5):1259-65. Amplification of wild-type KRAS also has been observed in ovarian, gastric, uterine, and lung cancers. See, e.g., Chen Y, et al., 2014, PLoS ONE, 9(5):e98293.

Expression of GST-π increases in various cancer cells, which may be related to resistance to some anticancer agents. See, e.g. Ban et al., Cancer Res., 1996, 56(15):3577-82; Nakajima et al., J Pharmacol Exp Ther., 2003, 306(3): 861-9.

Agents for suppressing GST-π have been disclosed for inducing apoptosis in cells. However, such compositions and techniques also caused autophagy and required the combined action of various agents. See, e.g., US 2014/0315975 A1. Moreover, suppressing GST-π has not been found to shrink or reduce tumors. For example, in a cancer that was overexpressing GST-π, the weights of tumors were not affected by suppressing GST-π, although other effects were observed. See, e.g., Hokaiwado et al., Carcinogenesis, 2008, 29(6): 1134-1138.

There is an urgent need for methods and compositions to develop therapies for patients with KRAS associated malignancies.

What is needed are methods and compositions for preventing or treating malignant tumors. There is a continuing need for RNAi molecules, and other structures and compositions for preventing, treating, reducing or shrinking malignant tumors.

BRIEF SUMMARY

This invention relates to the fields of biopharmaceuticals and therapeutics composed of nucleic acid based molecules. More particularly, this invention relates to tumor therapies for preventing, treating or ameliorating KRAS-associated cancers in which the cancer cells contain a KRAS mutation or display aberrant KRAS expression levels. This invention further relates to a pharmaceutical composition containing one or more RNAi molecules for inhibiting expression of GST-π.

This invention relates to the surprising discovery that malignant tumor size can be reduced in vivo by treatment with siRNA inhibitors of GST-π.

In some embodiments, malignant tumors containing a KRAS mutation or displaying aberrant KRAS expression levels can be reduced by treatment with siRNA agents that modulate expression of GST-π.

This invention relates to methods and compositions for nucleic acid based therapeutic compounds against malignant tumors. In some embodiments, this invention provides RNAi molecules, structures and compositions that can silence expression of GST-π. The structures and compositions of this disclosure can be used in preventing, treating or reducing the size of malignant tumors.

This invention provides compositions and methods that may be used for treating a neoplasia in a subject. In particular, this invention provides therapeutic compositions that can decrease the expression of a GST-π nucleic acid molecule or polypeptide for treating a KRAS-associated neoplasia without unwanted autophagy.

In some aspects, this invention includes an inhibitory nucleic acid molecule that corresponds to, or is complementary to at least a fragment of a GST-π nucleic acid molecule, and that decreases GST-π expression in a cell.

In further aspects, the invention features a double-stranded inhibitory nucleic acid molecule that corresponds to, or is complementary to at least a fragment of a GST-π nucleic acid molecule that decreases GST-π expression in a cell. In certain embodiments, the double-stranded nucleic acid molecule is a siRNA or a shRNA.

In some aspects, this invention includes a vector encoding an inhibitory nucleic acid molecule described above. A vector can be a retroviral, adenoviral, adeno-associated viral, or lentiviral vector. In further embodiments, a vector can contain a promoter suitable for expression in a mammalian cell. Additional embodiments include cancer cells containing a KRAS mutation or displaying aberrant KRAS expression levels, which can also contain the vector, or an inhibitory nucleic acid molecule of any one of the above aspects. In further embodiments, the cells can be neoplastic cells in vivo.

In some embodiments, this invention includes methods for decreasing GST-π expression in a malignant tumor cell containing a KRAS mutation or displaying aberrant KRAS expression. Methods can include contacting the cell with an effective amount of an inhibitory nucleic acid molecule corresponding to, or complementary to at least a portion of a GST-π nucleic acid molecule, where the inhibitory nucleic acid molecule inhibits expression of a GST-π polypeptide, thereby decreasing GST-π expression in the cell.

In certain embodiments, the inhibitory nucleic acid molecule can be an antisense nucleic acid molecule, a small interfering RNA (siRNA), or a double-stranded RNA (dsRNA) that is active for inhibiting gene expression.

In additional embodiments, methods of this invention can decrease GST-π transcription or translation in malignant tumors.

In particular embodiments, this invention includes methods for decreasing GST-π expression in a malignant tumor cell, where the cell can be a human cell, a neoplastic cell, a cell in vivo, or a cell in vitro.

Embodiments of this invention can also provide methods for treating a subject having a neoplasm, where neoplasm cancer cells contain a KRAS mutation or display aberrant KRAS expression levels. Methods can involve administering to the subject an effective amount of an inhibitory nucleic acid molecule corresponding to, or complementary to a GST-π nucleic acid molecule, where the inhibitory nucleic acid molecule reduces GST-π expression, thereby treating the neoplasm. In some embodiments, methods of this invention can decrease the size of a neoplasm, relative to the size of the neoplasm prior to treatment or without treatment.

In various embodiments, an inhibitory nucleic acid molecule can be delivered in a liposome, a polymer, a microsphere, a nanoparticle, a gene therapy vector, or a naked DNA vector.

In further aspects, this invention features methods for treating a subject, e.g. a human patient, having a neoplasm in which the neoplasm cancer cells contain a KRAS mutation or display aberrant KRAS expression levels. In certain embodiments, the methods can include administering to the subject an effective amount of an inhibitory nucleic acid molecule, where the inhibitory nucleic acid molecule is an antisense nucleic acid molecule, a siRNA, or a dsRNA that inhibits expression of a GST-π polypeptide.

In particular embodiments, a cell of the neoplasm overexpresses GST-π.

In certain embodiments, the neoplasm can be a malignant tumor, or lung cancer, or pancreatic cancer.

Embodiments of this invention include the following:

A pharmaceutical composition for the treatment or therapy of a tumor associated with a mutation in the KRAS gene or overexpression of wild-type KRAS gene, the composition comprising RNAi molecules and pharmaceutically acceptable excipients, wherein the RNAi molecules comprise a nucleotide sequence corresponding to a target sequence of GST-π.

In some embodiments, the pharmaceutical composition includes RNAi molecules that have a duplex region comprising a nucleotide sequence corresponding to a target sequence of GST-π mRNA.

In certain aspects, the RNAi molecules are siRNAs or shRNAs that are active for suppressing gene expression.

The pharmaceutical composition can include pharmaceutically acceptable excipients such as one or more lipid compounds. The lipid compounds may include lipid nanoparticles. In certain embodiments, the lipid nanoparticles can encapsulate the RNAi molecules.

This invention further contemplates methods for preventing, treating or ameliorating one or more symptoms of a malignant tumor associated with KRAS mutation in a mammal in need thereof, the method comprising:

identifying a tumor cell in the mammal, the tumor cell comprising at least one of: (i) a mutation of the KRAS gene, and (ii) an aberrant expression level of KRAS protein; and administering to the mammal a therapeutically effective amount of a composition comprising one or more RNAi molecules that are active in reducing expression of GST-π.

In such methods, the mammal can be a human, and the GST-π can be a human GST-π. The RNAi molecule can be a siRNA, shRNA, or microRNA.

In certain embodiments, the RNAi molecule can have a duplex region, wherein the duplex region can include a nucleotide sequence corresponding to a target sequence of GST-π mRNA. The RNAi molecule can decrease expression of GST-π in the mammal.

In some embodiments, the administration can decrease expression of GST-π in the mammal by at least 5% for at least 5 days. In certain embodiments, the administration can decrease the volume of the malignant tumor in the mammal by at least 5%, or at least 10%, or at least 20%, or at least 30%, or at least 40%, or at least 50%. In additional embodiments, the method can reduce one or more symptoms of the malignant tumor, or delay or terminate progression or growth of the malignant tumor.

In certain embodiments, the administration can reduce growth of malignant tumor cells in the subject. The administration can reduce growth for at least 2%, or at least 5%, or at least 10%, or at least 15%, or at least 20% of the malignant tumor cells in the subject.

In general, the tumor cells can have increased levels of expression of wild type KRAS protein compared to that in a normal cell. In some embodiments, the tumor cell overexpress wild-type GST-π RNA or protein.

In particular, the tumor cell can have mutations in the KRAS protein at one or more of residues 12, 13 and 61.

This invention contemplates that the tumor cell can have mutations in the KRAS protein, and the tumor can be a cancer selected from lung cancer, colon cancer, and pancreatic cancer.

In some embodiments, the tumor cell can have mutations in the KRAS protein, and the tumor can be a sarcoma selected from the group consisting of lung adenocarcinoma, mucinous adenoma, ductal carcinoma of the pancreas, and colorectal carcinoma. In certain embodiments, the malignant tumor can be a sarcoma selected from the group of lung adenocarcinoma, mucinous adenoma, ductal carcinoma of the pancreas, colorectal carcinoma, breast cancer, and fibrosarcoma. Also, the malignant tumor can be located in an anatomical region selected from the group of lung, colon, pancreas, gallbladder, liver, breast, and any combination thereof.

Aspects of this invention can provide methods in which the administration is performed from 1 to 12 times per day. The administration can be performed for a duration of 1, 2, 3, 4, 5, 6 or 7 days. In certain embodiments, the administration can be performed for a duration of 1, 2, 3, 4, 5, 6, 8, 10 or 12 weeks.

A dose for administration can be from 0.01 to 2 mg/kg of the RNAi molecules at least once per day for a period up to twelve weeks. In some embodiments, the administration can provide a mean AUC(0-last) of from 1 to 1000 ug*min/mL and a mean $C_{max}$ of from 0.1 to 50 ug/mL for the GST-π RNAi molecule.

The administration can be by intravenous injection, intradermal injection, subcutaneous injection, intramuscular injection, intraperitoneal injection, oral, topical, infusion, or inhaled.

These and other aspects will become apparent from the following description of the embodiments taken in conjunction with the following drawings, although variations and modifications therein may be affected without departing from the spirit and scope of the novel concepts of the disclosure.

BRIEF DESCRIPTION OF THE DRAWINGS

FIG. 1 shows the profound reduction of orthotopic lung cancer tumors in vivo by a siRNA of this invention targeted to GST-π. The GST-π siRNA was administered in a liposomal formulation at a dose of 2 mg/kg to athymic nude mice presenting A549 orthotopic lung cancer tumors. Final primary tumor weights were measured at necropsy for the treatment group and a vehicle control group. The GST-π siRNA showed significant efficacy for inhibition of lung cancer tumors in this six-week study. As shown in FIG. 1, after 43 days, the GST-π siRNA showed markedly advantageous tumor inhibition, with final primary tumor average weights significantly reduced by 2.8-fold, as compared to control.

FIG. 2 shows tumor inhibition efficacy in vivo for a GST-π siRNA. A cancer xenograft model using A549 cells was utilized with a relatively low dose of siRNA at 0.75 mg/kg. The GST-π siRNA showed advantageous tumor inhibition within a few days. After 36 days, the GST-π siRNA showed markedly advantageous tumor inhibition, with final tumor average volumes significantly reduced by about 2-fold, as compared to control.

FIG. 3 shows tumor inhibition efficacy in vivo for a GST-π siRNA at the endpoint of FIG. 2. The GST-π siRNA showed advantageous tumor inhibition with average tumor weights reduced by more than 2-fold.

FIG. 4 shows that a GST-π siRNA of this invention greatly increased cancer cell death by apoptosis in vitro. The GST-π siRNA caused upregulation of PUMA, a biomarker for apoptosis, which is associated with loss in cell viability. In FIG. 4, the expression of PUMA was greatly increased from 2-6 days after transfection of the GST-π siRNA.

FIG. 5 shows that a GST-π siRNA of this invention provided knockdown efficacy for A549 xenograft tumors in vivo. Dose dependent knockdown of GST-π mRNA was observed in athymic nude (nu/nu) female mice (Charles River) with the siRNA targeted to GST-π. As shown in FIG. 5, at a dose of 4 mg/kg, significant reduction of about 40% in GST-π mRNA was detected 24 hours after injection.

FIG. 6 shows that a GST-π siRNA of this invention inhibited pancreatic cancer xenograft tumors in vivo. The GST-π siRNA provided gene silencing potency in vivo when administered in a liposomal formulation to pancreatic cancer xenograft tumors in athymic nude female mice, 6 to 8 weeks old. As shown in FIG. 6, a dose response was obtained with doses ranging from 0.375 mg/kg to 3 mg/kg of siRNA targeted to GST-π. The GST-π siRNA showed advantageous tumor inhibition within a few days after administration, the tumor volume being reduced by about 2-fold at the endpoint.

FIG. 7 shows that a GST-π siRNA of this invention exhibited increased serum stability. As shown in FIG. 7, the half-life ($t_{1/2}$) in serum for both the sense strand (FIG. 7, top) and antisense strand (FIG. 7, bottom) of a GST-π siRNA was about 100 minutes.

FIG. 8 shows that a GST-π siRNA of this invention exhibited enhanced stability in formulation in plasma. FIG. 8 shows incubation of a liposomal formulation of a GST-π siRNA in 50% human serum in PBS, and detection of remaining siRNA at various time points. As shown in FIG. 8, the half-life ($t_{1/2}$) in plasma of the formulation of the GST-π siRNA was significantly longer than 100 hours.

FIG. 9 shows in vitro knockdown for the guide strand of a GST-π siRNA. As shown in FIG. 9, the guide strand knockdown of the GST-π siRNA was approximately exponential, as compared to a control with scrambled sequence that exhibited no effect.

FIG. 10 shows in vitro knockdown for the passenger strand of the GST-π siRNA of FIG. 9. As shown in FIG. 10, the passenger strand off target knockdown for the GST-π siRNA was greatly reduced, with essentially no effect.

FIG. 11 shows in vitro knockdown for the guide strands of several highly active GST-π siRNAs. As shown in FIG. 11, the guide strand knockdown activities of the GST-π siRNAs were approximately exponential.

FIG. 12 shows in vitro knockdown for the passenger strand of the GST-π siRNAs of FIG. 11. As shown in FIG. 12, the passenger strand off target knockdown activities for the GST-π siRNAs were significantly reduced below about 500 pM.

FIG. 13 shows in vitro knockdown for the guide strand of a highly active GST-π siRNA. As shown in FIG. 13, the guide strand knockdown activity of the GST-π siRNA was approximately exponential.

FIG. 14 shows in vitro knockdown for the passenger strand of the GST-π siRNA of FIG. 13. As shown in FIG. 14, the passenger strand off target knockdown activity for the GST-π siRNA was significantly reduced.

FIG. 15 shows tumor inhibition efficacy in vivo for GST-π siRNAs having structure based on siRNA A9. A cancer xenograft model using A549 cells was utilized with a relatively low dose of siRNA at 0.5 mg/kg. The GST-π siRNAs showed advantageous tumor inhibition within a few days. After 36 days, the GST-π siRNAs showed markedly advantageous tumor inhibition, with final tumor average volumes significantly reduced by about 2-fold, as compared to control.

FIG. 16 shows tumor inhibition efficacy in vivo for a GST-π siRNA having structure based on siRNA B13. A cancer xenograft model using A549 cells was utilized with a relatively low dose of siRNA at 0.75 mg/kg. The GST-π siRNA showed advantageous tumor inhibition within a few days. After 36 days, the GST-π siRNA showed markedly advantageous tumor inhibition, with final tumor average volumes significantly reduced by about 2-fold, as compared to control.

DETAILED DESCRIPTION OF THE INVENTION

Figure 1:
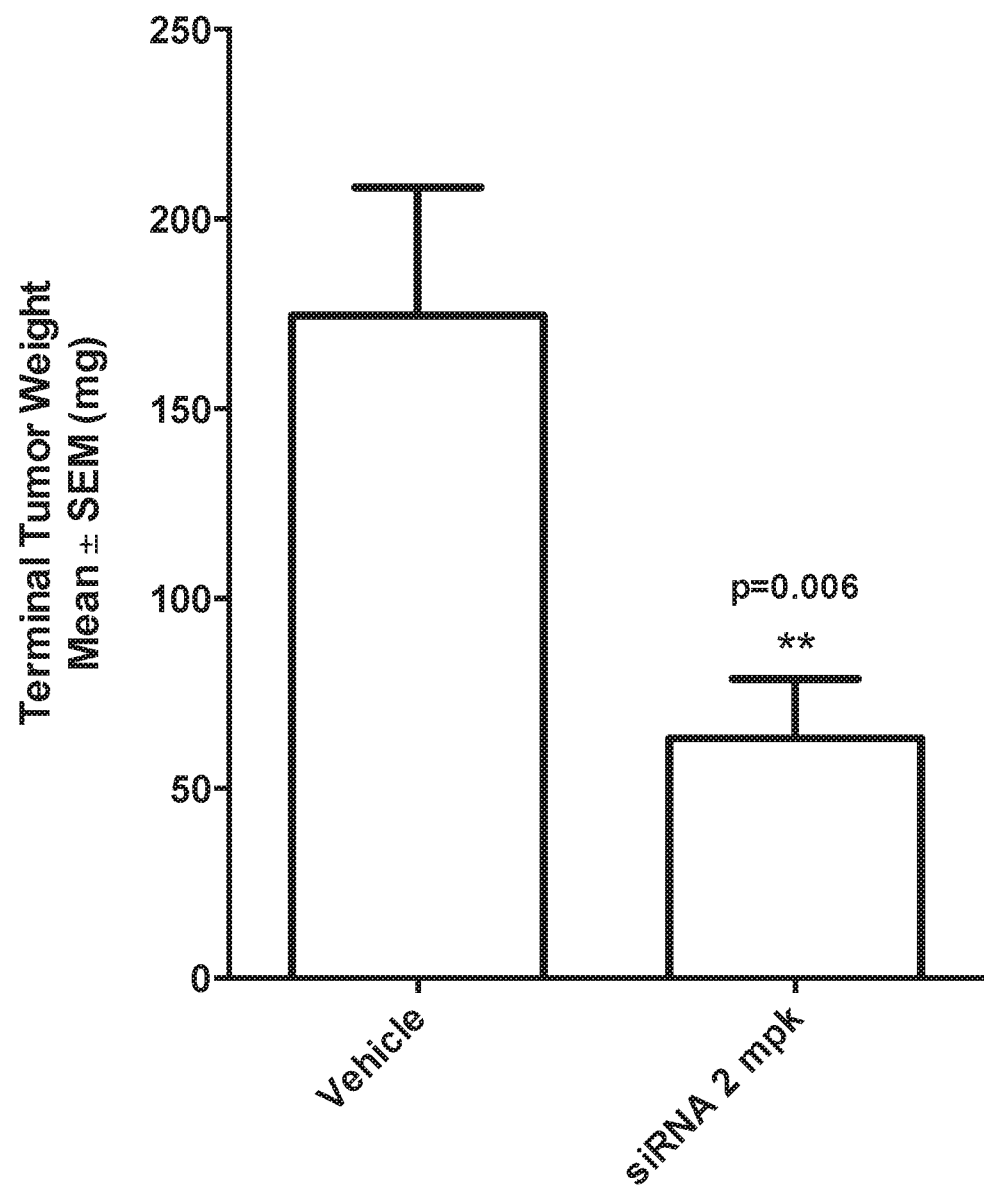
FIG. 1.

The invention provides methods for utilizing therapeutic compositions that decrease the expression of a GST-π nucleic acid molecule or polypeptide for the treatment of a neoplasia in a subject, wherein the neoplasia is associated with cells containing a KRAS mutation or displaying aberrant KRAS expression levels.

The therapeutic compositions of this invention can include inhibitory nucleic acid molecules such as siRNAs, shRNAs, and antisense RNAs.

GST-π denotes an enzyme, which is encoded by the GSTP1 gene, and catalyzes glutathione conjugation. GST-π is present in various animals, including humans, and its sequence information is known and given in NCBI database accession numbers (e.g., human: NP_000843 (NM_000852), rat: NP_036709 (NM_012577), mouse: NP_038569 (NM_013541), etc.

By "GST-π polypeptide" is meant a protein or protein variant, or fragment thereof, that is substantially identical to at least a portion of a protein encoded by the GST-π coding sequence. By "GST-π: nucleic acid molecule" is meant a polynucleotide encoding a GST-π polypeptide or variant, or fragment thereof.

Occurrence of a mutation of a gene sequence or an amino acid sequence between biological individuals may not impair the physiological function of a protein. GST-π and GSTP1 gene in this invention are not limited to a protein or nucleic acid having the same sequence as the GST-π sequences listed herein, and can include those that have a sequence that is different from the above sequence by one or more amino acids or bases, for example, one, two, three, four, five, six, seven, eight, nine, or ten amino acids or bases, but have an equivalent function to that of the known GST-π.

The sequence of Human glutathione S-transferase gene (GST-π), complete CDS, GenBank Accession No.: U12472, is shown in Table 1.

TABLE 1

| | The complete sequence of the human GSTπ gene. (SEQ ID NO: 1) | | | |
|---:|---|---|---|---|
| 1 | gtggctcacc | tgtacccagc | acttgggaag | ccgaggcgtg cagatcacct aagtcaggag |
| 61 | ttcgagacca | gcccggccaa | catggtgaaa | ccccgtctct actaaaaata caaaaatcag |
| 121 | ccagatgtgg | cacgcaccta | tatccaccta | ctcgggaggc tgaagcagaa tgcttaaccc |
| 181 | gagaggcgga | ggttgcagtg | agccgcccag | atcgcgccac tgcactccag cctgggccac |
| 241 | agcgtgagac | tactcataaa | ataaaataaa | ataaaataaa ataaaataaa ataaaataaa |
| 301 | ataataaaat | aaaataaaat | aaaataaaat | ataaaataaa ataaaataaa ataaaataaa |
| 361 | ataaaataaa | ataaaagcaa | tttcctttcc | tctaagcggc ctccacccct ctccctgcc |
| 421 | ctgtgaacgg | gggaagctcc | ggatcgcagc | aattagggaa tttccccccg cgatgtcccg |
| 481 | gcgcgccagt | tcggcgcaca | tctttcgcta | cggtcctctt cctgctgtct gtttactccc |
| 541 | taggcccctg | gacctgggaa | agagggaaag | gcttcccgcc agctgcgcgg cgactccggg |
| 601 | gactccaggg | cgcccctctg | cggcgacgcc | cgggtgcagc ggccgccggg ctggggccgg |
| 661 | cgggactccg | cgggaccctc | cagaagagcg | gccggcggct gactcagcac tggggcggag |
| 721 | gggcgggaca | cccttataag | gctcggagcg | cgagccttcg ctggagtttc gccgccgcag |
| 781 | tcttcgccac | cagtgagtac | gcggccgcgt | ccccggggat ggggctcaga gctccagcat |
| 841 | ggggccaacc | cgcagcatca | ggcccgggctc | ccggcggcct ccccacctcg agacccggga |
| 901 | cggggcctag | gggacccagg | acgtcccagt | gccgttagcg gctttcaggg ggcccggagc |
| 961 | gcctcgggga | gggatgggac | cccggggcg | ggagggcagc tcactcaccg cgccttggca |
| 1021 | tcctccccgg | gctccacaaa | ttttctttgt | tcgctgcagt gccgccctac accgtggtct |

TABLE 1-continued

The complete sequence of the human GSTπ gene. (SEQ ID NO: 1)

```
1081 atttcccagt tcgaggtagg agcatgtgtc tggcagggaa gggaggcagg ggctggggct
1141 gcagcaccca cagcccccac ccggagagat ccgaaccccc ttatccctcg tcgtgtgctt
1201 ttaccccegg cctccttcct gttccccgcc tctcccgcca tgcctgctcc ccgcccagt
1261 gttgtgtgaa atcttcggag gaacctgttt ccctgttccc tccctgcact cctgacccct
1321 ccccgggttg ctgcgaggcg gagtcggccc ggtccccaca tctcgtactt ctccctcccc
1381 gcaggccgct gcgcggccct gcgcatgctg ctggcagatc agggccagag ctggaaggag
1441 gaggtggtga ccgtggagac gtggcaggag ggctcactca aagcctcctg cgtaagtgac
1501 catgcccggg caaggggagg gggtgctggg ccttaggggg ctgtgactag gatcggggga
1561 cgccccaagc tcagtgcccc tccctgagcc atgcctcccc caacagctat acgggcagct
1621 ccccaagttc caggacggag acctcaccct gtaccagtcc aataccatcc tgcgtcacct
1681 gggccgcacc cttggtgagt cttgaacctc caagtccagg gcaggcatgg gcaagcctct
1741 gcccccggag ccctttttgtt taaatcagct gccccgcagc cctctggagt ggaggaaact
1801 gagacccact gaggttacgt agtttgccca aggtcaagcc tgggtgcctg caatccttcc
1861 cctgtgccag gctgcctccc aggtgtcagg tgagctctga gcacctgctg tgtggcagtc
1921 tctcatcctt ccacgcacat cctcttcccc tcctcccagg ctggggctca cagacagccc
1981 cctggttggc ccatcccag tgactgtgtt gatcaggcgc ccagtcacgc ggcctgctcc
2041 cctccaccca accccagggc tctatgggaa ggaccagcag gaggcagccc tggtggacat
2101 ggtgaatgac ggcgtggagg acctccgctc caaatacatc tccctcatct acaccaacta
2161 tgtgagcatc tgcaccaggg ttgggcactg ggggctgaac aaagaaaggg gcttcttgtg
2221 ccctcacccc ccttacccct caggtggctt gggctgaccc cttcttgggt cagggtgcag
2281 gggctgggtc agctctgggc cagggggggcc tgggacaaga cacaacctgc acccttattg
2341 cctgggacat caaccaccca agtaacgggt catgggggcg agtgcaagga cagagacctc
2401 cagcaactgg tggtttctgc tctcctgggg tggccagagg tggaggagga tttgtgccag
2461 tttctggatg gagccgctgg cgcttttagc tgaggaaaat atgagacaca gagcactttg
2521 ggtaccaggg accagttcag cagaggcagc gtgtgtggcg tgtgtgtgcg tgtgtgtgcg
2581 tgtgtgtgtg tacgcttgca tttgtgtcgg gtgggtaagg agatagagat ggggcggcag
2641 taggcccagg tcccgaaggc cttgaaccca ctggtttgga gtctcctaag ggcaatgggg
2701 gccattgaga agtctgaaca gggctgtgtc tgaatgtgag gtctagaagg atcctccaga
2761 gaagccagct ctaaagcttt tgcaatcatc tggtgagaga acccagcaag catggacagg
2821 cagaatggaa tagagatgag ttggcagctg aagtggacag gatttggtac tagcctggtt
2881 gtggggagca agcagaggag aatctgggac tctggtgtct ggcctgggc agacgggggt
2941 gtctcagggg ctgggaggga tgagagtagg atgatacatg gtgtgtgctg gcaggaggcg
3001 ggcaaggatg actatgtgaa ggcactgccc gggcaactga agccttttga gaccctgctg
3061 tcccagaacc agggaggcaa gaccttcatt gtgggagacc aggtgagcat ctggccccat
3121 gctgttcctt cctcgccacc ctctgcttcc agatggacac aggtgtgagc catttgttta
3181 gcaaagcaga gcagacctag gggatgggct taggccctct gccccaatt cctctccagc
3241 ctgctcccgc tggctgagtc cctagccccc ctgccctgca gatctccttc gctgactaca
3301 acctgctgga cttgctgctg atccatgagg tcctagcccc tggctgcctg gatgcgttcc
3361 ccctgctctc agcatatgtg gggcgcctca gtgcccggcc caagctcaag gccttcctgg
```

TABLE 1-continued

The complete sequence of the human GSTπ gene. (SEQ ID NO: 1)

```
3421 cctcccctga gtacgtgaac ctccccatca atggcaacgg gaaacagtga gggttggggg
3481 gactctgagc gggaggcaga gtttgccttc ctttctccag gaccaataaa agggctaaga
3541 gagctactat gagcactgtg tttcctggga cggggcttag gggttctcag cctc
```

A KRAS-associated malignant tumor or KRAS-associated cancer is defined herein as (a) a cancer cell or tumor cell containing a somatic KRAS mutation, or (b) a cancer cell or tumor cell with an abnormal expression level of KRAS including, but not limited to, amplification of the KRAS encoding DNA, or over-expression of the KRAS gene, or under-expression of the KRAS gene when compared to level found in normal, non-cancer cells.

Table 2 shows the amino acid sequence of the KRAS protein and identifies the mutations associated with cancer.

TABLE 2

Amino acid sequence of KRAS
protein and mutations associated with cancer
(SEQ ID NO: 2)

KRAS protein coding sequence, Isoform 2A
(identifier: P01116-1)

```
            10         20         30         40
    MTEYKLVVVG AGGVGKSALT IQLIQNHFVD EYDPTIEDSY 50         60         70         80
    RKQVVIDGET CLLDILDTAG QEEYSAMRDQ YMRTGEGFLC 90        100        110        120
    VFAINNTKSF EDIHHYREQI KRVKDSEDVP MVLVGNKCDL 130        140        150        160
    PSRTVDTKQA QDLARSYGIP FIETSAKTRQ RVEDAFYTLV 170        180
    REIRQYRLKK ISKEEKTPGC VKIKKCIIM
```

KRAS protein coding sequence, isoform 2A
(identifier: P01116-1)

| | |
|---|---|
| Mutations at position 12: | G → A in a colorectal cancer sample<br>G → C in lung carcinoma<br>G → D in pancreatic carcinoma, GASC and lung carcinoma<br>G → S in lung carcinoma and GASC<br>G → V in lung carcinoma, pancreatic carcinoma, colon cancer and GASC |
| Mutations at position 13: | G → D in a breast carcinoma cell line and GASC<br>G → R in pylocytic astrocytoma; amplification of the Ras pathway |
| Mutations at position 61: | Q → H in lung carcinoma<br>Q → R in a colorectal cancer |

QIAGEN's THERASCREEN KRAS TEST is a genetic test designed to detect the presence of seven mutations in the KRAS gene in colorectal cancer cells.

Therapeutic Compositions

After a subject is diagnosed as having a neoplasia, e.g., a lung cancer or a pancreatic cancer, associated with a KRAS mutation or a KRAS amplification, a method of treatment involving suppression of GST-π is selected.

In one embodiment, the inhibitory nucleic acid molecules of the invention are administered systemically in dosages from about 1 to 100 mg/kg, e.g., 1, 5, 10, 20, 25, 50, 75, or 100 mg/kg.

In further embodiments, the dosage can range from about 25 to 500 mg/m²/day.

Examples of an agent that suppresses GST-π as used herein include a drug that suppresses GST-π production and/or activity, and a drug that promotes GST-π degradation and/or inactivation. Examples of the drug that suppresses GST-π production include an RNAi molecule, a ribozyme, an antisense nucleic acid, a DNA/RNA chimera polynucleotide for DNA encoding GST-π, or a vector expressing same.

GST-pi and RNAi Molecules

One of ordinary skill in the art would understand that a reported sequence may change over time and to incorporate any changes needed in the nucleic acid molecules herein accordingly.

Embodiments of this invention can provide compositions and methods for gene silencing of GST-pi expression using small nucleic acid molecules. Examples of nucleic acid molecules include molecules active in RNA interference (RNAi molecules), short interfering RNA (siRNA), double-stranded RNA (dsRNA), micro-RNA (miRNA), and short hairpin RNA (shRNA) molecules. Such molecules are capable of mediating RNA interference against GST-pi gene expression.

The composition and methods disclosed herein can also be used in treating various kinds of malignant tumors in a subject.

The nucleic acid molecules and methods of this invention may be used to down regulate the expression of genes that encode GST-pi.

The compositions and methods of this invention can include one or more nucleic acid molecules, which, independently or in combination, can modulate or regulate the expression of GST-pi protein and/or genes encoding GST-pi proteins, proteins and/or genes encoding GST-pi associated with the maintenance and/or development of diseases, conditions or disorders associated with GST-pi, such as malignant tumor.

The compositions and methods of this invention are described with reference to exemplary sequences of GST-pi. A person of ordinary skill in the art would understand that various aspects and embodiments of the invention are directed to any related GST-pi genes, sequences, or variants, such as homolog genes and transcript variants, and polymorphisms, including single nucleotide polymorphism (SNP) associated with any GST-pi genes.

In some embodiments, the compositions and methods of this invention can provide a double-stranded short interfering nucleic acid (siRNA) molecule that downregulates the expression of a GST-pi gene, for example human GST-pi.

A RNAi molecule of this invention can be targeted to GST-pi and any homologous sequences, for example, using complementary sequences or by incorporating non-canonical base pairs, for example, mismatches and/or wobble base pairs, that can provide additional target sequences.

In instances where mismatches are identified, non-canonical base pairs, for example, mismatches and/or wobble bases can be used to generate nucleic acid molecules that target more than one gene sequence.

For example, non-canonical base pairs such as UU and CC base pairs can be used to generate nucleic acid molecules that are capable of targeting sequences for differing GST-pi targets that share sequence homology. Thus, a RNAi molecule can be targeted to a nucleotide sequence that is conserved between homologous genes, and a single RNAi molecule can be used to inhibit expression of more than one gene.

In some aspects, the compositions and methods of this invention include RNAi molecules that are active against GST-pi mRNA, where the RNAi molecule includes a sequence complementary to any mRNA encoding a GST-pi sequence.

In some embodiments, a RNAi molecule of this disclosure can have activity against GST-pi RNA, where the RNAi molecule includes a sequence complementary to an RNA having a variant GST-pi encoding sequence, for example, a mutant GST-pi gene known in the art to be associated with malignant tumor.

In further embodiments, a RNAi molecule of this invention can include a nucleotide sequence that can mediate silencing of GST-pi gene expression.

Examples of RNAi molecules of this invention targeted to GST-π mRNA are shown in Table 3.

TABLE 3

RNAi molecule sequences for GST-π

| ID | Ref Pos | SEQ ID NO SEQ ID NOS: 3 to 67 | SENSE STRAND (5'→3') | SEQ ID NO SEQ ID NOS: 68 to 132 | ANTISENSE STRAND (5'→3') |
|---|---|---|---|---|---|
| A1 | 652 | 3 | UCCCAGAACCAGGGAGGCAtt | 68 | UGCCUCCCUGGUUCUGGGAca |
| A10 | 635 | 4 | CUUUUGAGACCCUGCUGUCtt | 69 | GACAGCAGGGUCUCAAAAGgc |
| A11 | 649 | 5 | CUGUCCCAGAACCAGGGAGtt | 70 | CUCCCUGGUUCUGGGACAGca |
| A12 | 650 | 6 | UGUCCCAGAACCAGGGAGGtt | 71 | CCUCCCUGGUUCUGGGACAGc |
| A13 | 631 | 7 | AAGCCUUUUGAGACCCUGCtt | 72 | GCAGGGUCUCAAAAGGCUUca |
| A14 | 638 | 8 | UUGAGACCCUGCUGUCCCAtt | 73 | UGGGACAGCAGGGUCUCAAaa |
| A15 | 636 | 9 | UUUUGAGACCCUGCUGUCCtt | 74 | GGACAGCAGGGUCUCAAAAgg |
| A16 | 640 | 10 | GAGACCCUGCUGUCCCAGAtt | 75 | UCUGGGACAGCAGGGUCUCaa |
| A17 | 332 | 11 | GCUGGAAGGAGGAGGUGGUtt | 76 | ACCACCUCCUCCUUCCAGCtc |
| A18 | 333 | 12 | CUGGAAGGAGGAGGUGGUGtt | 77 | CACCACCUCCUCCUUCCAGct |
| A19 | 321 | 13 | UCAGGGCCAGAGCUGGAAGtt | 78 | CUUCCAGCUCUGGCCCUGAtc |
| A2 | 639 | 14 | UGAGACCCUGCUGUCCCAGtt | 79 | CUGGGACAGCAGGGUCUCAaa |
| A20 | 323 | 15 | AGGGCCAGAGCUGGAAGGAtt | 80 | UCCUUCCAGCUCUGGCCCUga |
| A21 | 331 | 16 | AGCUGGAAGGAGGAGGUGGtt | 81 | CCACCUCCUCCUUCCAGCUct |
| A22 | 641 | 17 | AGACCCUGCUGUCCCAGAAtt | 82 | UUCUGGGACAGCAGGGUCUca |
| A23 | 330 | 18 | GAGCUGGAAGGAGGAGGUGtt | 83 | CACCUCCUCCUUCCAGCUCtg |
| A25 | 647 | 19 | UGCUGUCCCAGAACCAGGGtt | 84 | CCCUGGUUCUGGGACAGCAgg |
| A26 | 653 | 20 | CCCAGAACCAGGGAGGCAAtt | 85 | UUGCCUCCCUGGUUCUGGGac |
| A3 | 654 | 21 | CCAGAACCAGGGAGGCAAGtt | 86 | CUUGCCUCCCUGGUUCUGGga |
| A4 | 637 | 22 | UUUGAGACCCUGCUGUCCCtt | 87 | GGGACAGCAGGGUCUCAAAag |
| A5 | 642 | 23 | GACCCUGCUGUCCCAGAACtt | 88 | GUUCUGGGACAGCAGGGUCtc |
| A6 | 319 | 24 | GAUCAGGGCCAGAGCUGGAtt | 89 | UCCAGCUCUGGCCCUGAUCtg |
| A7 | 632 | 25 | AGCCUUUUGAGACCCUGCUtt | 90 | AGCAGGGUCUCAAAAGGCUtc |
| A8 | 633 | 26 | GCCUUUUGAGACCCUGCUGtt | 91 | CAGCAGGGUCUCAAAAGGCtt |
| A9 | 634 | 27 | CCUUUUGAGACCCUGCUGUtt | 92 | ACAGCAGGGUCUCAAAAGGct |
| AG7 | 632 | 28 | CGCCUUUUGAGACCCUGCAtt | 93 | UGCAGGGUCUCAAAAGGCGtc |
| AK1 | 257 | 29 | CCUACACCGUGGUCUAUUUtt | 94 | AAAUAGACCACGGUGUAGGgc |

TABLE 3-continued

RNAi molecule sequences for GST-π

| ID | Ref Pos | SEQ ID NO | SENSE STRAND (5'→3') SEQ ID NOS: 3 to 67 | SEQ ID NO | ANTISENSE STRAND (5'→3') SEQ ID NOS: 68 to 132 |
|---|---|---|---|---|---|
| AK10 | 681 | 30 | UGUGGGAGACCAGAUCUCCtt | 95 | GGAGAUCUGGUCUCCCACAat |
| AK11 | 901 | 31 | GCGGGAGGCAGAGUUUGCCtt | 96 | GGCAAACUCUGCCUCCCGCtc |
| AK12 | 922 | 32 | CCUUUCUCCAGGACCAAUAtt | 97 | UAUUGGUCCUGGAGAAAGGaa |
| AK13/A24 | 643 | 33 | ACCCUGCUGUCCCAGAACCtt | 98 | GGUUCUGGGACAGCAGGGUct |
| AK2 | 267 | 34 | GGUCUAUUUCCCAGUUCGAtt | 99 | UCGAACUGGGAAAUAGACCac |
| AK3 | 512 | 35 | CCCUGGUGGACAUGGUGAAtt | 100 | UUCACCAUGUCCACCAGGGct |
| AK4 | 560 | 36 | ACAUCUCCCUCAUCUACACtt | 101 | GUGUAGAUGAGGGAGAUGUat |
| AK5 | 593 | 37 | GCAAGGAUGACUAUGUGAAtt | 102 | UUCACAUAGUCAUCCUUGCcc |
| AK6 | 698 | 38 | CCUUCGCUGACUACAACCUtt | 103 | AGGUUGUAGUCAGCGAAGGag |
| AK7 | 313 | 39 | CUGGCAGAUCAGGGCCAGAtt | 104 | UCUGGCCCUGAUCUGCCAGca |
| AK8 | 421 | 40 | GACGGAGACCUCACCCUGUtt | 105 | ACAGGGUGAGGUCUCCGUCct |
| AK9 | 590 | 41 | CGGGCAAGGAUGACUAUGUtt | 106 | ACAUAGUCAUCCUUGCCCGcc |
| AU10 | 635 | 42 | CUUUUGAGACCCUGCUGUAtt | 107 | UACAGCAGGGUCUCAAAAGgc |
| AU23 | 330 | 43 | GAGCUGGAAGGAGGAGGUAtt | 108 | UACCUCCUCCUUCCAGCUCtg |
| AU24 | 643 | 44 | ACCCUGCUGUCCCAGAACAtt | 109 | UGUUCUGGGACAGCAGGGUct |
| AU25 | 648 | 45 | UGCUGUCCCAGAACCAGGAtt | 110 | UCCUGGUUCUGGGACAGCAgg |
| AU7 | 632 | 46 | AGCCUUUUGAGACCCUGCAtt | 111 | UGCAGGGUCUCAAAAGGCUtc |
| AU9 | 634 | 47 | CCUUUUGAGACCCUGCUGAtt | 112 | UCAGCAGGGUCUCAAAAGGct |
| B1 | 629 | 48 | UGAAGCCUUUUGAGACCCUtt | 113 | AGGGUCUCAAAAGGCUUCAgt |
| B10 | 627 | 49 | ACUGAAGCCUUUUGAGACCtt | 114 | GGUCUCAAAAGGCUUCAGUtg |
| B11 | 595 | 50 | AAGGAUGACUAUGUGAAGGtt | 115 | CCUUCACAUAGUCAUCCUUgc |
| B12 | 596 | 51 | AGGAUGACUAUGUGAAGGCtt | 116 | GCCUUCACAUAGUCAUCCUtg |
| B13 | 597 | 52 | GGAUGACUAUGUGAAGGCAtt | 117 | UGCCUUCACAUAGUCAUCCtt |
| B14 | 564 | 53 | CUCCCUCAUCUACACCAACtt | 118 | GUUGGUGUAGAUGAGGGAGat |
| B2 | 630 | 54 | GAAGCCUUUUGAGACCCUGtt | 119 | CAGGGUCUCAAAAGGCUUCag |
| B3 | 563 | 55 | UCUCCCUCAUCUACACCAAtt | 120 | UUGGUGUAGAUGAGGGAGAtg |
| B4 | 567 | 56 | CCUCAUCUACACCAACUAUtt | 121 | AUAGUUGGUGUAGAUGAGGga |
| B5 | 566 | 57 | CCCUCAUCUACACCAACUAtt | 122 | UAGUUGGUGUAGAUGAGGGag |
| B6 | 625 | 58 | CAACUGAAGCCUUUUGAGAtt | 123 | UCUCAAAAGGCUUCAGUUGcc |
| B7 | 626 | 59 | AACUGAAGCCUUUUGAGACtt | 124 | GUCUCAAAAGGCUUCAGUUgc |
| B8 | 628 | 60 | CUGAAGCCUUUUGAGACCCtt | 125 | GGGUCUCAAAAGGCUUCAGtt |
| B9 | 565 | 61 | UCCCUCAUCUACACCAACUtt | 126 | AGUUGGUGUAGAUGAGGGAga |
| BG3 | 553 | 62 | GCUCCCUCAUCUACACCAAtt | 127 | UUGGUGUAGAUGAGGGAGCtg |
| BU2 | 630 | 63 | GAAGCCUUUUGAGACCCUAtt | 128 | UAGGGUCUCAAAAGGCUUCag |
| BU10 | 627 | 64 | ACUGAAGCCUUUUGAGACAtt | 129 | UGUCUCAAAAGGCUUCAGUtg |
| BU14 | 565 | 65 | CUCCCUCAUCUACACCAAAtt | 130 | UUUGGUGUAGAUGAGGGAGat |

TABLE 3-continued

RNAi molecule sequences for GST-π

| ID | Ref Pos | SEQ ID NO | SENSE STRAND (5'→3') SEQ ID NOS: 3 to 67 | SEQ ID NO | ANTISENSE STRAND (5'→3') SEQ ID NOS: 68 to 132 |
|---|---|---|---|---|---|
| BU4 | 567 | 66 | CCUCAUCUACACCAACUAAtt | 131 | UUAGUUGGUGUAGAUGAGGga |
| C1-934 | 934 | 67 | ACCAAUAAAAUUUCUAAGAtt | 132 | UCUUAGAAAUUUUAUUGGUcc |

Key for Table 3: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine respectively.

Examples of RNAi molecules of this invention targeted to GST-π mRNA are shown in Table 4.

TABLE 4

RNAi molecule sequences for GST-π

| ID | SEQ ID NO | SENSE STRAND (5'→3') SEQ ID NOS: 133 to 158 | SEQ ID NO | ANTISENSE STRAND (5'→3') SEQ ID NOS: 159 to 184 |
|---|---|---|---|---|
| BU2' | 133 | GAAGCCUUUUGAGACCCUANN | 159 | UAGGGUCUCAAAAGGCUUCNN |
| 14 | 134 | GAAGCCUUUUGAGACCCUA<u>UU</u> | 160 | UAGGGUCUCAAAAGGCUUC<u>UU</u> |
| 15 | 135 | GAAGCCUUUUGAGACCCUA<u>UU</u> | 161 | uagggucuCAAAAGGCUUC<u>UU</u> |
| 16 | 136 | GAAGCCUUUUGAGACCCUA<u>UU</u> | 162 | UagggucuCAAAAGGCUUC<u>UU</u> |
| 17 | 137 | GAAGCCUUUUGAGACCCUA<u>UU</u> | 163 | UAgggucuCAAAAGGCUUC<u>UU</u> |
| 18 | 138 | GAAGCCUUUUGAGACCCUA<u>UU</u> | 164 | UAGggucuCAAAAGGCUUC<u>UU</u> |
| 19 | 139 | GAAGCCUUUUGAGACCCUA<u>UU</u> | 165 | UAGGgucuCAAAAGGCUUC<u>UU</u> |
| 20 | 140 | GAAGCCUUUUGAGACCCUA<u>UU</u> | 166 | uAgGgUcUCAAAAGGCUUC<u>UU</u> |
| 21 | 141 | GAAGCCUUUUGAGACCCUA<u>UU</u> | 167 | UAgGgUcUCAAAAGGCUUC<u>UU</u> |
| 22 | 142 | GAAGCCUUUUGAGACCCUA<u>UU</u> | 168 | UaGgGuCuCAAAAGGCUUC<u>UU</u> |
| 23 | 143 | GAAGCCUUUUGAGACCCUA<u>UU</u> | 169 | UAGgGuCuCAAAAGGCUUC<u>UU</u> |
| 24 | 144 | GAAGCCUUUUGAGACCCUAtt | 170 | UagggucuCAAA<u>A</u><u>GG</u>C<u>UU</u>C<u>UU</u> |
| 25 | 145 | GAAGCCUUUUGAGACCCUA<u>UU</u> | 171 | <u>U</u>AGGGUCUCAAAAGGCUUC<u>UU</u> |
| 26 | 146 | GAAGCCUUUUGAGACCCUA<u>UU</u> | 172 | fUAGGGUCUCAAAAGGCUUC<u>UU</u> |
| 27 | 147 | GAAGCCUUUUGAGACCCUA<u>UU</u> | 173 | uAGGGUCUCAAAAGGCUUC<u>UU</u> |
| 28 | 148 | GAAGCCUUUUGAGACCCUA<u>UU</u> | 174 | UsAGGGUCUCAAAAGGCUUCUU |
| 29 | 149 | GAAGCCUUUUGAGACCCUfA<u>UU</u> | 175 | fUAGGGUCUfCAAAAGGCfUUC<u>UU</u> |
| 30 | 150 | GAAGCCUUUUGAGfACCCUfA<u>UU</u> | 176 | fUAGGGUCUfCAfAfAAGGCfUUC<u>UU</u> |
| 31 | 151 | GAAGCCUUUUGAGACCCUA<u>UU</u> | 177 | <u>U</u>AGGGUCU<u>C</u>AAAAGGC<u>U</u>UC<u>UU</u> |
| 31' | 152 | GAAGCCUUUUGAGACCCUA<u>UU</u> | 178 | fUAGGGUCU<u>C</u>AAAAGGC<u>UU</u>C<u>UU</u> |
| 32 | 153 | <u>GAA</u>GCCUUUUGAGACCCUA<u>UU</u> | 179 | UAGGGUCUCAAAAGGCUUC<u>UU</u> |
| 39 | 154 | <u>GAA</u>GC<u>CUU</u>UUGAGACCCUA<u>UU</u> | 180 | UAGgGuCuCAAAAGGCUUC<u>UU</u> |
| 45 | 155 | <u>GAA</u>GC<u>CUU</u>UUGAGACCCUA<u>UU</u> | 181 | UAGgGuC<u>u</u>C<u>A</u>AAAGGCU<u>U</u>C<u>UU</u> |
| 46 | 156 | <u>GAA</u>GC<u>CUU</u>UUGAGACCCUA<u>UU</u> | 182 | UAGgGuC<u>u</u>C<u>AAA</u>AGGCUUC<u>UU</u> |

TABLE 4-continued

RNAi molecule sequences for GST-π

| ID | SEQ ID NO | SENSE STRAND (5'→3') SEQ ID NOS: 133 to 158 | SEQ ID NO | ANTISENSE STRAND (5'→3') SEQ ID NOS: 159 to 184 |
|---|---|---|---|---|
| 47 | 157 | GA<u>AG</u>CC<u>U</u>U<u>UU</u>GAGACCC<u>UAUU</u> | 183 | <u>UA</u>GgGuCu<u>CAAA</u>AGGC<u>UUCUU</u> |
| 48 | 158 | GA<u>AG</u>CC<u>U</u>U<u>UU</u>GAGACCC<u>UAUU</u> | 184 | f<u>UA</u>GgGuCu<u>CAAA</u>AGGC<u>UUCUU</u> |

Key for Table 4: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., <u>U</u>. The lower case letter f refers to 2'-deoxy-2'-fluoro substitution, e.g. fU is 2'-deoxy-2'-fluoro-U. N is A, C, G, U, <u>U</u>, a, c, g, u, t, or a modified, inverted, or chemically modified nucleotide.

Examples of RNAi molecules of this invention targeted to GST-π mRNA are shown in Table 5.

TABLE 5

RNAi molecule sequences for GST-π

| ID | SEQ ID NO | SENSE STRAND (5'→3') SEQ ID NOS: 185 to 196 | SEQ ID NO | ANTISENSE STRAND (5'→3') SEQ ID NOS: 197 to 208 |
|---|---|---|---|---|
| A9' | 185 | CCUUUUGAGAC CCUGCUGUNN | 197 | ACAGCAGGGUC UCAAAAGGNN |
| 1 | 186 | CCUUUUGAGAC CCUGCUG<u>UUU</u> | 198 | ACAGCAGGGUC UCAAAAGG<u>UU</u> |
| 2 | 187 | CCUUUUGAGAC CCUGCUG<u>UUU</u> | 199 | acagcaggGUC UCAAAAGG<u>UU</u> |
| 3 | 188 | CCUUUUGAGAC CCUGCUG<u>UUU</u> | 200 | AcagcaggGUC UCAAAAGG<u>UU</u> |
| 4 | 189 | CCUUUUGAGAC CCUGCUG<u>UUU</u> | 201 | ACagcaggGUC UCAAAAGG<u>UU</u> |
| 5 | 190 | CCUUUUGAGAC CCUGCUG<u>UUU</u> | 202 | ACAgcaggGUC UCAAAAGG<u>UU</u> |
| 6 | 191 | CCUUUUGAGAC CCUGCUG<u>UUU</u> | 203 | ACAGcaggGUC UCAAAAGG<u>UU</u> |
| 7 | 192 | CCUUUUGAGAC CCUGCUG<u>UUU</u> | 204 | aCaGcAgGGUC UCAAAAGG<u>UU</u> |
| 8 | 193 | CCUUUUGAGAC CCUGCUG<u>UUU</u> | 205 | AcaGcAgGGUC UCAAAAGG<u>UU</u> |
| 9 | 194 | CCUUUUGAGAC CCUGCUG<u>UUU</u> | 206 | AcAgCaGgGGUC UCAAAAGG<u>UU</u> |
| 10 | 195 | CCUUUUGAGAC CCUGCUG<u>UUU</u> | 207 | ACAgCaGgGUC UCAAAAGG<u>UU</u> |
| 11 | 196 | <u>CCUUUUGAGAC CCUGCUGUUU</u> | 208 | Acagcagg<u>GUC UCAAAAGGUU</u> |

Key for Table 5: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., <u>U</u>. The lower case letter f refers to 2'-deoxy-2'-fluoro substitution, e.g. fU is 2'-deoxy-2'-fluoro-U. N is A, C, G, U, <u>U</u>, a, c, g, u, t, or a modified, inverted, or chemically modified nucleotide.

Examples of RNAi molecules of this invention targeted to GST-π mRNA are shown in Table 6.

TABLE 6

RNAi molecule sequences for GST-π

| ID | SEQ ID NO | SENSE STRAND (5'→3') SEQ ID NOS: 209 to 223 | SEQ ID NO | ANTISENSE STRAND (5'→3') SEQ ID NOS: 224 to 238 |
|---|---|---|---|---|
| B13' | 209 | GGAUGACUAUGU GAAGGCANN | 224 | UGCCUUCACAU AGUCAUCCNN |
| 4 | 210 | GGAUGACUAUGU GAAGGCA<u>UU</u> | 225 | UGCCUUCACAU AGUCAUCC<u>UU</u> |
| 5 | 211 | UgccuucaCAU GAAGGCA<u>UU</u> | 226 | AGUCAUCC<u>UU</u> |
| 6 | 212 | GGAUGACUAUGU GAAGGCA<u>UU</u> | 227 | UgccuucaCAU AGUCAUCC<u>UU</u> |
| 7 | 213 | GGAUGACUAUGU GAAGGCA<u>UU</u> | 228 | UGccuucaCAU AGUCAUCC<u>UU</u> |
| 8 | 214 | GGAUGACUAUGU GAAGGCA<u>UU</u> | 229 | UGCcuucaCAU AGUCAUCC<u>UU</u> |
| 9 | 215 | GGAUGACUAUGU GAAGGCA<u>UU</u> | 230 | UGCCuucaCAU AGUCAUCC<u>UU</u> |
| 10 | 216 | GGAUGACUAUGU GAAGGCA<u>UU</u> | 231 | UGCCUUCACAU AGUCAUCC<u>UU</u> |
| 11 | 217 | GGAUGACUAUGU GAAGGCA<u>UU</u> | 232 | UGcCuUcACAU AGUCAUCC<u>UU</u> |
| 12 | 218 | GGAUGACUAUGU GAAGGCA<u>UU</u> | 233 | UgCcUuCaCAU AGUCAUCC<u>UU</u> |
| 13 | 219 | GGAUGACUAUGU GAAGGCA<u>UU</u> | 234 | UGCcUuCaCAU AGUCAUCC<u>UU</u> |
| 14 | 220 | <u>GGAUGAC</u>UAUGU GAAGGCA<u>UU</u> | 235 | UgccuucaCAU AG<u>U</u>C<u>AU</u>CC<u>UU</u> |
| 15 | 221 | GGAUGACUAUfG UfGAAGGCA<u>UU</u> | 236 | UGCfCUUCACA UAGUCAUCC<u>UU</u> |
| 17 | 222 | <u>GG</u>AUGACUAUGU GAAGGCA<u>UU</u> | 237 | UGCCUUCA<u>C</u>AU A<u>GU</u>C<u>AU</u>CC<u>UU</u> |
| 18 | 223 | <u>GG</u>AUGACUAUGU GAAGGCA<u>UU</u> | 238 | UGCCUUCAC<u>A</u>U A<u>GU</u>C<u>AU</u>CC<u>UU</u> |

Key for Table 6: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., <u>U</u>. The lower case letter f refers to 2'-deoxy-2'-fluoro substitution, e.g. fU is 2'-deoxy-2'-fluoro-U. N is A, C, G, U, U, a, c, g, u, t, or a modified, inverted, or chemically modified nucleotide.

Examples of RNAi molecules of this invention targeted to GST-π mRNA are shown in Table 7.

TABLE 7

RNAi molecule sequences for GST-π

| ID | SEQ ID NO | SENSE STRAND (5'→3') SEQ ID NOS: 239 to 250 | SEQ ID NO | ANTISENSE STRAND (5'→3') SEQ ID NOS: 251 to 262 |
|---|---|---|---|---|
| B2' | 239 | GAAGCCUUUUG AGACCCUGNN | 251 | CAGGGUCUCAA AAGGCUUCNN |
| 1 | 240 | GAAGCCUUUUG AGACCCUGUU | 252 | CAGGGUCUCAA AAGGCUUCUU |
| 2 | 241 | GAAGCCUUUUG AGACCCUGUU | 253 | cagggucuCAA AAGGCUUCUU |
| 3 | 242 | GAAGCCUUUUG AGACCCUGUU | 254 | CagggucuCAA AAGGCUUCUU |
| 4 | 243 | GAAGCCUUUUG AGACCCUGUU | 255 | CAgggucuCAA AAGGCUUCUU |
| 5 | 244 | GAAGCCUUUUG AGACCCUGUU | 256 | CAGggucuCAA AAGGCUUCUU |
| 6 | 245 | GAAGCCUUUUG AGACCCUGUU | 257 | CAGGgucuCAA AAGGCUUCUU |
| 7 | 246 | GAAGCCUUUUG AGACCCUGUU | 258 | cAgGgUcUCAA AAGGCUUCUU |
| 8 | 247 | GAAGCCUUUUG AGACCCUGUU | 259 | CAgGgUcUCAA AAGGCUUCUU |
| 9 | 248 | GAAGCCUUUUG AGACCCUGUU | 260 | CaGgGuCuCAA AAGGCUUCUU |
| 10 | 249 | GAAGCCUUUUG AGACCCUGUU | 261 | CAGgGuCuCAA AAGGCUUCUU |
| 11 | 250 | GAAGCCUUUUG AGACCCUGUU | 262 | CagggucuCAA AAGGCUUCUU |

Key for Table 7: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., U. The lower case letter f refers to 2'-deoxy-2'-fluoro substitution, e.g. fU is 2'-deoxy-2'-fluoro-U. N is A, C, G, U, U, a, c, g, u, t, or a modified, inverted, or chemically modified nucleotide.

Examples of RNAi molecules of this invention targeted to GST-π mRNA are shown in Table 8.

TABLE 8

RNAi molecule sequences for GST-π

| ID | SEQ ID NO | SENSE STRAND (5'→3') SEQ ID NOS: 263 to 274 | SEQ ID NO | ANTISENSE STRAND (5'→3') SEQ ID NOS: 275 to 286 |
|---|---|---|---|---|
| B4' | 263 | CCUCAUCUACA CCAACUAUNN | 275 | AUAGUUGGUGU AGAUGAGGNN |
| 1 | 264 | CCUCAUCUACA CCAACUAUUU | 276 | AUAGUUGGUGU AGAUGAGGUU |
| 2 | 265 | CCUCAUCUACA CCAACUAUUU | 277 | auaguuggUGU AGAUGAGGUU |
| 3 | 266 | CCUCAUCUACA CCAACUAUUU | 278 | AuaguuggUGU AGAUGAGGUU |
| 4 | 267 | CCUCAUCUACA CCAACUAUUU | 279 | AUaguuggUGU AGAUGAGGUU |
| 5 | 268 | CCUCAUCUACA CCAACUAUUU | 280 | AUAguuggUGU AGAUGAGGUU |
| 6 | 269 | CCUCAUCUACA CCAACUAUUU | 281 | AUAGuuggUGU AGAUGAGGUU |
| 7 | 270 | CCUCAUCUACA CCAACUAUUU | 282 | aUaGuUgGUGU AGAUGAGGUU |
| 8 | 271 | CCUCAUCUACA CCAACUAUUU | 283 | AUaGuUgGUGU AGAUGAGGUU |
| 9 | 272 | CCUCAUCUACA CCAACUAUUU | 284 | AuAgUuGgUGU AGAUGAGGUU |
| 10 | 273 | CCUCAUCUACA CCAACUAUUU | 285 | AUAgUuGgUGU AGAUGAGGUU |
| 11 | 274 | CCUCAUCUACA CCAACUAUUU | 286 | AuaguuggUGU AGAUGAGGUU |

Key for Table 8: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., U. The lower case letter f refers to 2'-deoxy-2'-fluoro substitution, e.g. fU is 2'-deoxy-2'-fluoro-U. N is A, C, G, U, U, a, c, g, u, t, or a modified, inverted, or chemically modified nucleotide.

As used herein, the RNAi molecule denotes any molecule that causes RNA interference, including, but not limited to, a duplex RNA such as siRNA (small interfering RNA), miRNA (micro RNA), shRNA (short hairpin RNA), ddRNA (DNA-directed RNA), piRNA (Piwi-interacting RNA), or rasiRNA (repeat associated siRNA) and modified forms thereof. These RNAi molecules may be commercially available or may be designed and prepared based on known sequence information, etc. The antisense nucleic acid includes RNA, DNA, PNA, or a complex thereof. As used herein, the DNA/RNA chimera polynucleotide includes, but is not limited to, a double-strand polynucleotide composed of DNA and RNA that inhibits the expression of a target gene.

In one embodiment, the agents of this invention contain siRNA as a therapeutic agent. An siRNA molecule can have a length from about 10-50 or more nucleotides. An siRNA molecule can have a length from about 15-45 nucleotides. An siRNA molecule can have a length from about 19-40 nucleotides. An siRNA molecule can have a length of from 19-23 nucleotides. An siRNA molecule of this invention can mediate RNAi against a target mRNA. Commercially available design tools and kits, such as those available from Ambion, Inc. (Austin, Tex.), and the Whitehead Institute of Biomedical Research at MIT (Cambridge, Mass.) allow for the design and production of siRNA.

Methods for Modulating GST-pi and Treating Malignant Tumor

Embodiments of this invention can provide RNAi molecules that can be used to down regulate or inhibit the expression of GST-pi and/or GST-pi proteins.

In some embodiments, a RNAi molecule of this invention can be used to down regulate or inhibit the expression of GST-pi and/or GST-pi proteins arising from GST-pi haplotype polymorphisms that may be associated with a disease or condition such as malignant tumor.

Monitoring of GST-pi protein or mRNA levels can be used to characterize gene silencing, and to determine the efficacy of compounds and compositions of this invention.

The RNAi molecules of this disclosure can be used individually, or in combination with other siRNAs for modulating the expression of one or more genes.

The RNAi molecules of this disclosure can be used individually, or in combination, or in conjunction with other known drugs for preventing or treating diseases, or ameliorating symptoms of conditions or disorders associated with GST-pi, including malignant tumor.

The RNAi molecules of this invention can be used to modulate or inhibit the expression of GST-pi in a sequence-specific manner.

The RNAi molecules of this disclosure can include a guide strand for which a series of contiguous nucleotides are at least partially complementary to a GST-pi mRNA.

In certain aspects, malignant tumor may be treated by RNA interference using a RNAi molecule of this invention.

Treatment of malignant tumor may be characterized in suitable cell-based models, as well as ex vivo or in vivo animal models.

Treatment of malignant tumor may be characterized by determining the level of GST-pi mRNA or the level of GST-pi protein in cells of affected tissue.

Treatment of malignant tumor may be characterized by non-invasive medical scanning of an affected organ or tissue.

Embodiments of this invention may include methods for preventing, treating, or ameliorating the symptoms of a GST-pi associated disease or condition in a subject in need thereof.

In some embodiments, methods for preventing, treating, or ameliorating the symptoms of malignant tumor in a subject can include administering to the subject a RNAi molecule of this invention to modulate the expression of a GST-pi gene in the subject or organism.

In some embodiments, this invention contemplates methods for down regulating the expression of a GST-pi gene in a cell or organism, by contacting the cell or organism with a RNAi molecule of this invention.

GST-π inhibitory nucleic acid molecules can be nucleotide oligomers that may be employed as single-stranded or double-stranded nucleic acid molecule to decrease GST-π expression. In one approach, the GST-π inhibitory nucleic acid molecule is a double-stranded RNA used for RNA interference (RNAi)-mediated knockdown of GST-π gene expression. In one embodiment, a double-stranded RNA (dsRNA) molecule is made that includes from eight to twenty-five (e.g., 8, 10, 12, 15, 16, 17, 18, 19, 20, 21, 22, 23, 24, 25) consecutive nucleotides of a nucleotide oligomer of the invention. The dsRNA can be two complementary strands of RNA that have duplexed, or a single RNA strand that has self-duplexed (small hairpin (sh)RNA).

In some embodiments, dsRNAs are about 21 or 22 base pairs, but may be shorter or longer, up to about 29 nucleotides. Double stranded RNA can be made using standard techniques, e.g., chemical synthesis or in vitro transcription. Kits are available, for example, from Ambion (Austin, Tex.) and Epicentre (Madison, Wis.).

Methods for expressing dsRNA in mammalian cells are described in Brummelkamp et al. Science 296:550-553, 2002; Paddison et al. Genes & Devel. 16:948-958, 2002; Paul et al. Nature Biotechnol. 20:505-508, 2002; Sui et al., Proc. Natl. Acad. Sci. USA 99:5515-5520, 2002; Yu et al. Proc. Natl. Acad. Sci. USA 99:6047-6052, 2002; Miyagishi et al., Nature Biotechnol. 20:497-500, 2002; and Lee et al., Nature Biotechnol. 20:500-505 2002, each of which is hereby incorporated by reference.

An inhibitory nucleic acid molecule that "corresponds" to a GST-π gene comprises at least a fragment of the double-stranded gene, such that each strand of the double-stranded inhibitory nucleic acid molecule is capable of binding to the complementary strand of the target GST-π gene. The inhibitory nucleic acid molecule need not have perfect correspondence to the reference GST-π sequence.

In one embodiment, a siRNA has at least about 85%, 90%, 95%, 96%, 97%, 98%, or even 99% sequence identity with the target nucleic acid. For example, a 19 base pair duplex having 1-2 base pair mismatch is considered useful in the methods of the invention. In other embodiments, the nucleotide sequence of the inhibitory nucleic acid molecule exhibits 1, 2, 3, 4, 5 or more mismatches.

The inhibitory nucleic acid molecules provided by the invention are not limited to siRNAs, but include any nucleic acid molecule sufficient to decrease the expression of a GST-π nucleic acid molecule or polypeptide. Each of the DNA sequences provided herein may be used, for example, in the discovery and development of therapeutic antisense nucleic acid molecule to decrease the expression of GST-π. The invention further provides catalytic RNA molecules or ribozymes. Such catalytic RNA molecules can be used to inhibit expression of an GST-π nucleic acid molecule in vivo. The inclusion of ribozyme sequences within an antisense RNA confers RNA-cleaving activity upon the molecule, thereby increasing the activity of the constructs. The design and use of target RNA-specific ribozymes is described in Haseloff et al., Nature 334:585-591. 1988, and US 2003/0003469 A1, each of which is incorporated by reference.

In various embodiments of this invention, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., Biochemistry, 28:4929, 1989, and Hampel et al., Nucleic Acids Research, 18: 299, 1990. Those skilled in the art will recognize that what is needed in an enzymatic nucleic acid molecule is a specific substrate binding site that is complementary to one or more of the target gene RNA regions, and that it have nucleotide sequences within or surrounding that substrate binding site which impart an RNA cleaving activity to the molecule.

Table 9 shows the mRNA coding sequence of GST-π.

TABLE 9

Glutathione S-transferase-π1 mRNA coding sequence, NCBI Reference Sequence: NM_000852.3, GeneID: 2950, Hugo gene Nomenclature Committee: HGNC: 4638, Human Protein Reference Database: HPRD: 00614 (SEQ ID NO: 287)

```
  1    tgggaaagag ggaaaggctt ccccggccag ctgcgcggcg actccgggga ctccagggcg
 61    ccsctctgcg gccgacgccc ggggtgcagc ggccgccggg gctggggccg gcgggagtcc
121    gcgggaccct ccagaagagc ggccggcgcc gtgactcagc actggggcgc agcggagcgg
181    gaccacccct ataaggctcc gaggccgcga ggccttcgct gcagtttccc cgccgcagtc
241    ttcgccacca tgccgcccta caccgtggtc tatttcccag ttcgaggccg ctgcgcggcc
301    ctgcgcatgc tgctggcaga tcagggccag agctggaagg aggaggtggt gaccgtggag
361    acgtggcagg agggctcact caaagcctcc tgcctatacg ggcagctccc caagttccag
421    gacggagacc tcaccctgta ccagtccaat accatcctgc gtcacctggg ccgcaccctt
481    gggctctatg ggaaggacca gcaggagcca gccctggtgg acatggtgaa tgacggcgtg
541    gaggacctcc gctgcaaata catctccctc atctacacca actatgaggc gggcaaggat
601    gactatgtga aggcactgcc cgggcaactg aagccttttg agaccctgct gtcccagaac
661    cagggaggca agaccttcat tgtgggagac cagatctcct tcgctgacta caacctgctg
721    gacttgctgc tgatccatga ggtcctagcc cctggctgcc tggatgcgtt ccccctgctc
781    tcagcatatg tggggcgcct cagtgcccgg cccaagctca aggccttcct ggcctcccct
841    gagtacgtga acctccccat caatggcaac gggaaacagt cagggttggc gggactctga
901    gcgggaggca gagtttgcct tcctttctcc aggaccaata aaatttctaa gagagctaaa
961    aaaaaaaaaa aaaaaaaaaa aaaaaa
```

The drug that suppresses GST-π production or activity can be an RNAi molecule, a ribozyme, an antisense nucleic acid, a DNA/RNA chimera polynucleotide for DNA encoding GST-π, or a vector expressing same, in terms of high specificity and a low possibility of side effects.

Suppression of GST-π may be determined by the expression or activity of GST-π in cells being suppressed compared with a case in which a GST-π suppressing agent is not utilized. Expression of GST-π may be evaluated by any known technique; examples thereof include an immunoprecipitation method utilizing an anti-GST-π antibody, EIA, ELISA, IRA, IRMA, a western blot method, an immunohistochemical method, an immunocytochemical method, a flow cytometry method, various hybridization methods utilizing a nucleic acid that specifically hybridizes with a nucleic acid encoding GST-π or a unique fragment thereof, or a transcription product (e.g., mRNA) or splicing product of said nucleic acid, a northern blot method, a Southern blot method, and various PCR methods.

The activity of GST-π may be evaluated by analyzing a known activity of GST-π including binding to a protein such as, for example, Raf-1 (in particular phosphorylated Raf-1) or EGFR (in particular phosphorylated EGFR) by means of any known method such as for example an immunoprecipitation method, a western blot method, amass analysis method, a pull-down method, or a surface plasmon resonance (SPR) method.

Whether or not GST-π is being expressed in certain cells may be determined by detecting expression of GST-π in cells. Expression of GST-π may be detected by any technique known in the art.

Examples of the mutated KRAS include, but are not limited to, those having a mutation that causes constant activation of KRAS, such as a mutation that inhibits endogenous GTPase or a mutation that increases the guanine nucleotide exchange rate. Specific examples of such mutation include, but are not limited to, for example, mutation in amino acids 12, 13 and/or 61 in human KRAS (inhibiting endogenous GTPase) and mutation in amino acids 116 and/or 119 in human KRAS (increasing guanine nucleotide exchange rate) (Bos, Cancer Res. 1989; 49 (17): 4682-9, Levi et al., Cancer Res. 1991; 51 (13): 3497-502).

In some embodiments of the present invention, the mutated KRAS can be a KRAS having a mutation in at least one of amino acids 12, 13, 61, 116, and 119 of human KRAS. In one embodiment of the present invention, the mutated KRAS has a mutation at amino acid 12 of human KRAS. In some embodiments, the mutated KRAS may be one that induces overexpression of GST-π. Cells having mutated KRAS may exhibit overexpression of GST-π.

Detection of mutated KRAS may be carried out using any known technique, e.g., selective hybridization by means of a nucleic acid probe specific to a known mutation sequence, an enzyme mismatch cleavage method, sequencing (Bos, Cancer Res. 1989; 49 (17): 4682-9), and a PCR-RFLP method (Miyanishi et al., Gastroenterology. 2001; 121 (4): 865-74).).

Detection of GST-π expression may be carried out using any known technique. Whether or not GST-π is being overexpressed may be evaluated by for example comparing the degree of expression of GST-π in cells having mutated KRAS with the degree of expression of GST-π in the same type of cells having normal KRAS. In this situation, GST-π is being overexpressed if the degree of expression of GST-π in cells having mutated KRAS exceeds the degree of expression of GST-π in the same type of cells having normal KRAS.

In one aspect, the invention features a vector encoding an inhibitory nucleic acid molecule of any of the above aspects. In a particular embodiment, the vector is a retroviral, adenoviral, adeno-associated viral, or lentiviral vector. In another embodiment, the vector contains a promoter suitable for expression in a mammalian cell.

The amount of active RNA interference inducing ingredient formulated in the composition of the present invention may be an amount that does not cause an adverse effect exceeding the benefit of administration. Such an amount may be determined by an in vitro test using cultured cells, or a test in a model animal such as a mouse, a rat, a dog, or a pig, etc., and such test methods are well known to a person skilled in the art.

The amount of active ingredient formulated can vary according to the manner in which the agent or composition is administered. For example, when a plurality of units of the composition is used for one administration, the amount of active ingredient to be formulated in one unit of the composition may be determined by dividing the amount of active ingredient necessary for one administration by said plurality of units.

This invention also relates to a process for producing an agent or composition for suppressing GST-π, and the use of a drug that suppresses GST-π in the production of an agent or composition for reducing or shrinking malignant tumors.

RNA Interference

RNA interference (RNAi) refers to sequence-specific post-transcriptional gene silencing in animals mediated by short interfering RNAs (siRNAs). See, e.g., Zamore et al., Cell, 2000, Vol. 101, pp. 25-33; Fire et al., Nature, 1998, Vol. 391, pp. 806811; Sharp, Genes & Development, 1999, Vol. 13, pp. 139-141.

An RNAi response in cells can be triggered by a double stranded RNA (dsRNA), although the mechanism is not yet fully understood. Certain dsRNAs in cells can undergo the action of Dicer enzyme, a ribonuclease III enzyme. See, e.g., Zamore et al., Cell, 2000, Vol. 101, pp. 25-33; Hammond et al., Nature, 2000, Vol. 404, pp. 293-296. Dicer can process the dsRNA into shorter pieces of dsRNA, which are siRNAs.

In general, siRNAs can be from about 21 to about 23 nucleotides in length and include a base pair duplex region about 19 nucleotides in length.

RNAi involves an endonuclease complex known as the RNA induced silencing complex (RISC). An siRNA has an antisense or guide strand which enters the RISC complex and mediates cleavage of a single stranded RNA target having a sequence complementary to the antisense strand of the siRNA duplex. The other strand of the siRNA is the passenger strand. Cleavage of the target RNA takes place in the middle of the region complementary to the antisense strand of the siRNA duplex See, e.g., Elbashir et al., Genes & Development, 2001, Vol. 15, pp. 188-200.

As used herein, the term "sense strand" refers to a nucleotide sequence of a siRNA molecule that is partially or fully complementary to at least a portion of a corresponding antisense strand of the siRNA molecule. The sense strand of a siRNA molecule can include a nucleic acid sequence having homology with a target nucleic acid sequence.

As used herein, the term "antisense strand" refers to a nucleotide sequence of a siRNA molecule that is partially or fully complementary to at least a portion of a target nucleic acid sequence. The antisense strand of a siRNA molecule can include a nucleic acid sequence that is complementary to at least a portion of a corresponding sense strand of the siRNA molecule.

RNAi molecules can down regulate or knock down gene expression by mediating RNA interference in a sequence-specific manner. See, e.g., Zamore et al., Cell, 2000, Vol. 101, pp. 25-33; Elbashir et al., Nature, 2001, Vol. 411, pp. 494-498; Kreutzer et al., WO2000/044895; Zernicka-Goetz et al., WO2001/36646; Fire et al., WO1999/032619; Plaetinck et al., WO2000/01846; Mello et al., WO2001/029058.

As used herein, the terms "inhibit," "down-regulate," or "reduce" with respect to gene expression means that the expression of the gene, or the level of mRNA molecules encoding one or more proteins, or the activity of one or more of the encoded proteins is reduced below that observed in the absence of a RNAi molecule or siRNA of this invention. For example, the level of expression, level of mRNA, or level of encoded protein activity may be reduced by at least 1%, or at least 10%, or at least 20%, or at least 50%, or at least 90%, or more from that observed in the absence of a RNAi molecule or siRNA of this invention.

RNAi molecules can also be used to knock down viral gene expression, and therefore affect viral replication.

RNAi molecules can be made from separate polynucleotide strands: a sense strand or passenger strand, and an antisense strand or guide strand. The guide and passenger strands are at least partially complementary. The guide strand and passenger strand can form a duplex region having from about 15 to about 49 base pairs.

In some embodiments, the duplex region of a siRNA can have 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 base pairs.

In certain embodiments, a RNAi molecule can be active in a RISC complex, with a length of duplex region active for RISC.

In additional embodiments, a RNAi molecule can be active as a Dicer substrate, to be converted to a RNAi molecule that can be active in a RISC complex.

In some aspects, a RNAi molecule can have complementary guide and passenger sequence portions at opposing ends of a long molecule, so that the molecule can form a duplex region with the complementary sequence portions, and the strands are linked at one end of the duplex region by either nucleotide or non-nucleotide linkers. For example, a hairpin arrangement, or a stem and loop arrangement. The linker interactions with the strands can be covalent bonds or non-covalent interactions.

A RNAi molecule of this disclosure may include a nucleotide, non-nucleotide, or mixed nucleotide/non-nucleotide linker that joins the sense region of the nucleic acid to the antisense region of the nucleic acid. A nucleotide linker can be a linker of ≥2 nucleotides in length, for example about 3, 4, 5, 6, 7, 8, 9, or 10 nucleotides in length. The nucleotide linker can be a nucleic acid aptamer. By "aptamer" or "nucleic acid aptamer" as used herein refers to a nucleic acid molecule that binds specifically to a target molecule wherein the nucleic acid molecule has sequence that includes a sequence recognized by the target molecule in its natural setting. Alternately, an aptamer can be a nucleic acid molecule that binds to a target molecule, where the target molecule does not naturally bind to a nucleic acid. For example, the aptamer can be used to bind to a ligand-binding domain of a protein, thereby preventing interaction of the naturally occurring ligand with the protein. See, e.g., Gold et al., Annu Rev Biochem, 1995, Vol. 64, pp. 763-797;

Brody et al., J. Biotechnol., 2000, Vol. 74, pp. 5-13; Hermann et al., Science, 2000, Vol. 287, pp. 820-825.

Examples of a non-nucleotide linker include an abasic nucleotide, polyether, polyamine, polyamide, peptide, carbohydrate, lipid, polyhydrocarbon, or other polymeric compounds, for example polyethylene glycols such as those having from 2 to 100 ethylene glycol units. Some examples are described in Seela et al., Nucleic Acids Research, 1987, Vol. 15, pp. 3113-3129; Cload et al., J. Am. Chem. Soc., 1991, Vol. 113, pp. 6324-6326; Jaeschke et al., Tetrahedron Lett., 1993, Vol. 34, pp. 301; Arnold et al., WO1989/002439; Usman et al., WO1995/006731; Dudycz et al., WO1995/011910, and Ferentz et al., J. Am. Chem. Soc., 1991, Vol. 113, pp. 4000-4002.

A RNAi molecule can have one or more overhangs from the duplex region. The overhangs, which are non-base-paired, single strand regions, can be from one to eight nucleotides in length, or longer. An overhang can be a 3'-end overhang, wherein the 3'-end of a strand has a single strand region of from one to eight nucleotides. An overhang can be a 5'-end overhang, wherein the 5'-end of a strand has a single strand region of from one to eight nucleotides.

The overhangs of a RNAi molecule can have the same length, or can be different lengths.

A RNAi molecule can have one or more blunt ends, in which the duplex region ends with no overhang, and the strands are base paired to the end of the duplex region.

A RNAi molecule of this disclosure can have one or more blunt ends, or can have one or more overhangs, or can have a combination of a blunt end and an overhang end.

A 5'-end of a strand of a RNAi molecule may be in a blunt end, or can be in an overhang. A 3'-end of a strand of a RNAi molecule may be in a blunt end, or can be in an overhang.

A 5'-end of a strand of a RNAi molecule may be in a blunt end, while the 3'-end is in an overhang. A 3'-end of a strand of a RNAi molecule may be in a blunt end, while the 5'-end is in an overhang.

In some embodiments, both ends of a RNAi molecule are blunt ends.

In additional embodiments, both ends of a RNAi molecule have an overhang.

The overhangs at the 5'- and 3'-ends may be of different lengths.

In certain embodiments, a RNAi molecule may have a blunt end where the 5'-end of the antisense strand and the 3'-end of the sense strand do not have any overhanging nucleotides.

In further embodiments, a RNAi molecule may have a blunt end where the 3'-end of the antisense strand and the 5'-end of the sense strand do not have any overhanging nucleotides.

A RNAi molecule may have mismatches in base pairing in the duplex region.

Any nucleotide in an overhang of a RNAi molecule can be a deoxyribonucleotide, or a ribonucleotide.

One or more deoxyribonucleotides may be at the 5'-end, where the 3'-end of the other strand of the RNAi molecule may not have an overhang, or may not have a deoxyribonucleotide overhang.

One or more deoxyribonucleotides may be at the 3'-end, where the 5'-end of the other strand of the RNAi molecule may not have an overhang, or may not have a deoxyribonucleotide overhang.

In some embodiments, one or more, or all of the overhang nucleotides of a RNAi molecule may be 2'-deoxyribonucleotides.

Dicer Substrate RNAi Molecules

In some aspects, a RNAi molecule can be of a length suitable as a Dicer substrate, which can be processed to produce a RISC active RNAi molecule. See, e.g., Rossi et al., US2005/0244858.

A Dicer substrate dsRNA can be of a length sufficient such that it is processed by Dicer to produce an active RNAi molecule, and may further include one or more of the following properties: (i) the Dicer substrate dsRNA can be asymmetric, for example, having a 3' overhang on the antisense strand, and (ii) the Dicer substrate dsRNA can have a modified 3' end on the sense strand to direct orientation of Dicer binding and processing of the dsRNA to an active RNAi molecule.

Methods of Use of RNAi Molecules

The nucleic acid molecules and RNAi molecules of this invention may be delivered to a cell or tissue by direct application of the molecules, or with the molecules combined with a carrier or a diluent.

The nucleic acid molecules and RNAi molecules of this invention can be delivered or administered to a cell, tissue, organ, or subject by direct application of the molecules with a carrier or diluent, or any other delivery vehicle that acts to assist, promote or facilitate entry into a cell, for example, viral sequences, viral material, or lipid or liposome formulations.

The nucleic acid molecules and RNAi molecules of this invention can be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection.

Delivery systems may include, for example, aqueous and nonaqueous gels, creams, emulsions, microemulsions, liposomes, ointments, aqueous and nonaqueous solutions, lotions, aerosols, hydrocarbon bases and powders, and can contain excipients such as solubilizers and permeation enhancers.

A GST-π inhibitory nucleic acid molecule of this invention may be administered within a pharmaceutically-acceptable diluents, carrier, or excipient, in unit dosage form. Conventional pharmaceutical practice may be employed to provide suitable formulations or compositions to administer the compounds to patients suffering from a disease that is caused by excessive cell proliferation. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Compositions and methods of this disclosure can include an expression vector that includes a nucleic acid sequence encoding at least one RNAi molecule of this invention in a manner that allows expression of the nucleic acid molecule.

The nucleic acid molecules and RNAi molecules of this invention can be expressed from transcription units inserted into DNA or RNA vectors. Recombinant vectors can be DNA plasmids or viral vectors. Viral vectors can be used that provide for transient expression of nucleic acid molecules.

For example, the vector may contain sequences encoding both strands of a RNAi molecule of a duplex, or a single nucleic acid molecule that is self-complementary and thus forms a RNAi molecule. An expression vector may include a nucleic acid sequence encoding two or more nucleic acid molecules.

A nucleic acid molecule may be expressed within cells from eukaryotic promoters. Those skilled in the art realize that any nucleic acid can be expressed in eukaryotic cells from the appropriate DNA/RNA vector.

In some aspects, a viral construct can be used to introduce an expression construct into a cell, for transcription of a dsRNA construct encoded by the expression construct.

Lipid formulations can be administered to animals by intravenous, intramuscular, or intraperitoneal injection, or orally or by inhalation or other methods as are known in the art.

Pharmaceutically acceptable formulations for administering oligonucleotides are known and can be used.

In one embodiment of the above method, the inhibitory nucleic acid molecule is administered at a dosage of about 5 to 500 mg/m$^2$/day, e.g., 5, 25, 50, 100, 125, 150, 175, 200, 225, 250, 275, or 300 mg/m$^2$/day.

Methods known in the art for making formulations are found, for example, in "Remington: The Science and Practice of Pharmacy" Ed. A. R. Gennaro, Lippincourt Williams & Wilkins, Philadelphia, Pa., 2000.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for GST-π inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts (e.g., amounts which prevent, eliminate, or reduce a pathological condition) to provide therapy for a neoplastic disease or condition. The preferred dosage of a nucleotide oligomer of the invention can depend on such variables as the type and extent of the disorder, the overall health status of the particular patient, the formulation of the compound excipients, and its route of administration.

All of the above methods for reducing malignant tumors may be either an in vitro method or an in vivo method. Dosage may be determined by an in vitro test using cultured cells, etc., as is known in the art. An effective amount may be an amount that reduces tumor size in KRAS associated tumors by at least 10%, at least 20%, or at least 30%, or at least 40%, or at least 50%, or at least 60%, or at least 70%, or at least 80%, or at least 90%, up to 100% of the tumor size.

A pharmaceutical composition of this invention can be effective in treating a KRAS associated disease. Examples of the diseases include a disease due to abnormal cell proliferation, a disease due to KRAS mutation, and a disease due to GST-a overexpression.

Examples of the disease due to abnormal cell proliferation include malignant tumors, hyperplasia, keloid, Cushing's syndrome, primary aldosteronism, erythroplakia, polycythemia vera, leukoplakia, hyperplastic scar, lichen planus, and lentiginosis.

Examples of the disease due to KRAS mutation include malignant tumor (also called a cancer or a malignant neoplasm).

Examples of the disease due to GST-π overexpression include malignant tumor.

Examples of cancer include sarcomas such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma, and osteosarcoma, carcinomas such as brain tumor, head and neck carcinoma, breast carcinoma, lung carcinoma, esophageal carcinoma, gastric carcinoma, duodenal carcinoma, colon carcinoma, rectal carcinoma, liver carcinoma, pancreatic carcinoma, gall bladder carcinoma, bile duct carcinoma, renal carcinoma, ureteral carcinoma, bladder carcinoma, prostate carcinoma, testicular carcinoma, uterine carcinoma, ovarian carcinoma, skin carcinoma, leukemia, and malignant lymphoma.

Cancer includes epithelial malignancy and non-epithelial malignancy. A cancer can be present at any site of the body, for example, the brain, head and neck, chest, limbs, lung, heart, thymus, esophagus, stomach, small intestine (duodenum, jejunum, ileum), large intestine (colon, cecum, appendix, rectum), liver, pancreas, gallbladder, kidney, urinary duct, bladder, prostate, testes, uterus, ovary, skin, striated muscle, smooth muscle, synovial membrane, cartilage, bone, thyroid, adrenal gland, peritoneum, mesentery, bone marrow, blood, vascular system, lymphatic system such as lymph node, lymphatic fluid, etc.

In one embodiment of the present invention, the cancer includes cancer cells having the mutated KRAS defined above. In another embodiment, the cancer includes cancer cells that exhibit hormone- or growth factor-independent proliferation. In further embodiments, a cancer includes cancer cells exhibiting GST-π overexpression.

EXAMPLES

Example 1 siRNAs of this invention targeted to GST-π were found to be active for gene silencing in vitro. The dose-dependent activities of GST-π siRNAs for gene knockdown were found to exhibit an IC50 below about 250 picomolar (pM), and as low as 1 pM.

In vitro transfection was performed in an A549 cell line to determine siRNA knockdown efficacy. Dose dependent knockdown for GST-π mRNA was observed with siRNAs of Table 3, as shown in Table 10.

TABLE 10

Dose dependent knockdown for GST-π mRNA in an A549 cell line

| siRNA structure | IC50 (pM) |
| --- | --- |
| A9 (SEQ ID NOs: 27 and 92) | 24 |
| B2 (SEQ ID NOs: 54 and 119) | 121 |
| B3 (SEQ ID NOs: 55 and 120) | 235 |
| B4 (SEQ ID NOs: 56 and 121) | 229 |
| B13 (SEQ ID NOs: 52 and 117) | 17 |
| BU2 (SEQ ID NOs: 63 and 128) | 31 |

As shown in Table 10, the activities of GST-π siRNAs of Table 3 were in the range 17-235 pM, which is suitable for many uses, including as a drug agent to be used in vivo.

Example 2

The structure of GST-π siRNAs of this invention having deoxynucleotides located in the seed region of the antisense strand of the siRNA provided unexpectedly and advantageously increased gene knockdown activity in vitro.

In vitro transfection was performed in an A549 cell line to determine knockdown efficacy for GST-π siRNAs based on structure BU2' (SEQ ID NOs: 133 and 159). Dose dependent knockdown of GST-π mRNA was observed with GST-π siRNAs based on structure BU2' as shown in Table 11.

TABLE 11

Dose dependent knockdown of GST-π mRNA in an A549 cell line for GST-π siRNAs based on structure BU2'

| GST-π siRNA structure | IC50 (pM) |
| --- | --- |
| BU2 with no deoxynucleotides in the duplex region (SEQ ID NOs: 63 and 128) | 31 |
| BU2 with deoxynucleotides in positions 3, 5, and 7 of the seed region antisense strand (SEQ ID NOs: 141 and 167) | 5 |
| BU2 with deoxynucleotides in positions 4, 6, and 8 of the seed region antisense strand (SEQ ID NOs: 143 and 169) | 8 |
| BU2 with deoxynucleotides in positions 4, 6, and 8 of the seed region antisense strand (SEQ ID NOs: 158 and 184) | 5 |

As shown in Table 11, the activities of GST-π siRNAs based on structure BU2' having three deoxynucleotides in the seed region of the antisense strand were surprisingly and unexpectedly increased by up to 6-fold, as compared to a GST-π siRNA without deoxynucleotides in the duplex region.

These data show that GST-π siRNAs having a structure with three deoxynucleotides located at positions 3, 5 and 7, or at positions 4, 6 and 8 in the seed region of the antisense strand provided surprisingly increased gene knockdown activity as compared to a GST-a siRNA without deoxynucleotides in the duplex region.

The activities shown in Table 11 for GST-π siRNAs having three deoxynucleotides in the seed region of the antisense strand were in the range 5 to 8 pM, which is exceptionally suitable for many uses, including as a drug agent to be used in vivo.

Example 3

The structure of GST-π siRNAs of this invention having deoxynucleotides located in the seed region of the antisense strand of the siRNA provided unexpectedly and advantageously increased gene knockdown activity in vitro.

In vitro transfection was performed in an A549 cell line to determine knockdown efficacy for GST-π siRNAs based on structure A9' (SEQ ID NOs: 185 and 197). Dose dependent knockdown of GST-π mRNA was observed with the GST-a siRNAs based on structure A9', as shown in Table 12.

TABLE 12

Dose dependent knockdown of GST-π mRNA in an A549 cell line for GST-π siRNAs based on structure structure A9'

| GST-π siRNA structure | IC50 (pM) |
| --- | --- |
| A9 with no deoxynucleotides in the duplex region (SEQ ID NOs: 27 and 92) | 24 |
| A9 with deoxynucleotides in positions 4, 6, and 8 of the seed region antisense strand (SEQ ID NOs: 195 and 207) | 1 |
| A9 with deoxynucleotides in positions 1, 3, 5, and 7 of the seed region antisense strand (SEQ ID NOs: 192 and 204) | 5 |
| A9 with deoxynucleotides in positions 3-8 of the seed region antisense strand (SEQ ID NOs: 189 and 201) | 6 |
| A9 with deoxynucleotides in positions 5-8 of the seed region antisense strand (SEQ ID NOs: 191 and 203) | 7 |
| A9 with deoxynucleotides in positions 3, 5, and 7 of the seed region antisense strand (SEQ ID NOs: 193 and 205) | 15 |

As shown in Table 12, the activities of GST-π siRNAs based on structure A9' having three to six deoxynucleotides in the seed region of the antisense strand were surprisingly increased by up to 24-fold, as compared to a GST-π siRNA without deoxynucleotides in the duplex region.

These data show that GST-π siRNAs having a structure with three to six deoxynucleotides located at positions 4, 6 and 8, or at positions 1, 3, 5 and 7, or at positions 3-8, or at positions 5-8, or at positions 3, 5 and 7 in the seed region of the antisense strand provided unexpectedly increased gene knockdown activity as compared to a GST-π siRNA without deoxynucleotides in the duplex region.

The activity shown in Table 12 for GST-π siRNAs having three to six deoxynucleotides in the seed region of the antisense strand was in the range 1 to 15 pM, which is exceptionally suitable for many uses, including as a drug agent to be used in vivo.

Example 4

The structure of GST-a siRNAs having deoxynucleotides located in the seed region of the antisense strand of the siRNA provided unexpectedly and advantageously increased gene knockdown activity in vitro.

In vitro transfection was performed in an A549 cell line to determine knockdown efficacy for GST-π siRNAs based on structure B13' (SEQ ID NOs:209 and 224). Dose dependent knockdown of GST-π mRNA was observed with the GST-π siRNAs based on structure B13', as shown in Table 13.

TABLE 13

Dose dependent knockdown of GST-π mRNA in an A549 cell line for GST-π siRNAs based on structure B13'

| GST-π siRNA structure | IC50 (pM) |
| --- | --- |
| B13 with no deoxynucleotides in the duplex region (SEQ ID NOs: 52 and 117) | 17 |
| B13 with deoxynucleotides in positions 4, 6, and 8 of the seed region antisense strand (SEQ ID NOs: 219 and 234) | 11 |

As shown in Table 13, the activity of a GST-π siRNA based on structure B13' having three deoxynucleotides in the seed region of the antisense strand was unexpectedly increased, as compared to a GST-π siRNA without deoxynucleotides in the duplex region.

These data show that GST-π siRNAs having a structure with three deoxynucleotides located at positions 4, 6 and 8 in the seed region of the antisense strand provided unexpectedly increased gene knockdown activity as compared to a GST-π siRNA without deoxynucleotides in the duplex region.

The activity shown in Table 13 for GST-π siRNAs having three deoxynucleotides in the seed region of the antisense strand was in the picomolar range at 11 pM, which is exceptionally suitable for many uses, including as a drug agent to be used in vivo.

Example 5

The structure of GST-π siRNAs having deoxynucleotides located in the seed region of the antisense strand of the siRNA provided unexpectedly and advantageously increased gene knockdown activity in vitro.

In vitro transfection was performed in an A549 cell line to determine knockdown efficacy for GST-π siRNAs based on structure B4' (SEQ ID NOs:263 and 275). Dose dependent knockdown of GST-π mRNA was observed with the GST-π siRNAs based on structure B4', as shown in Table 14.

TABLE 14

Dose dependent knockdown of GST-π mRNA in an A549 cell line for GST-π siRNAs based on structure B4'

| GST-π siRNA structure | IC50 (pM) |
| --- | --- |
| B4 with no deoxynucleotides in the duplex region (SEQ ID NOs: 56 and 121) | 229 |
| B4 with deoxynucleotides in positions 3-8 of the seed region antisense strand (SEQ ID NOs: 267 and 279) | 113 |

As shown in Table 14, the activities of GST-π siRNAs based on structure B4' having six deoxynucleotides in the seed region of the antisense strand were unexpectedly increased by more than two-fold, as compared to a GST-π siRNA without deoxynucleotides in the duplex region.

These data show that GST-π siRNAs having a structure with six deoxynucleotides located at positions 3-8 in the seed region of the antisense strand provided surprisingly increased gene knockdown activity as compared to a GST-π siRNA without deoxynucleotides in the duplex region.

The activity shown in Table 14 for a GST-π siRNA having six deoxynucleotides in the seed region of the antisense strand was in the picomolar range at 113 pM, which is exceptionally suitable for many uses, including as a drug agent to be used in vivo.

Example 6

The structure of GST-π siRNAs having deoxynucleotides located in the seed region of the antisense strand of the siRNA provided unexpectedly and advantageously increased gene knockdown activity in vitro.

In vitro transfection was performed in an A549 cell line to determine knockdown efficacy for GST-π siRNAs based on structure B2' (SEQ ID NOs:239 and 251). Dose dependent knockdown of GST-π mRNA was observed with the GST-π siRNAs based on structure B2', as shown in Table 15.

TABLE 15

Dose dependent knockdown of GST-π mRNA in an A549 cell line for GST-π siRNAs based on structure B2'

| GST-π siRNA structure | IC50 (pM) |
| --- | --- |
| B2 with no deoxynucleotides in the duplex regioin (SEQ ID NOs: 54 and 119) | 121 |
| B2 with deoxynucleotides in positions 5-8 of the seed region antisense strand (SEQ ID NOs: 245 and 257) | 30 |
| B2 with deoxynucleotides in positions 1, 3, 5, and 7 of the seed region antisense strand (SEQ ID NOs: 246 and 258) | 50 |
| B2 with deoxynucleotides in positions 3, 5, and 7 of the seed region antisense strand (SEQ ID NOs: 246 and 259) | 100 |

As shown in Table 15, the activities of GST-π siRNAs based on structure B2' having three to four deoxynucleotides in the seed region of the antisense strand were surprisingly increased by up to 4-fold, as compared to a GST-π siRNA without deoxynucleotides in the duplex region.

These data show that GST-π siRNAs having a structure with three to four deoxynucleotides located at positions 5-8, or at positions 1, 3, 5 and 7, or at positions 3, 5 and 7 in the seed region of the antisense strand provided unexpectedly increased gene knockdown activity as compared to a GST-π siRNA without deoxynucleotides in the duplex region.

The activities shown in Table 15 for GST-π siRNAs having three to four deoxynucleotides in the seed region of the antisense strand were in the range 30-100 pM, which is exceptionally suitable for many uses, including as a drug agent to be used in vivo.

Example 7

The structure of GST-π siRNAs containing one or more 2'-deoxy-2'-fluoro substituted nucleotides provided unexpectedly increased gene knockdown activity in vitro.

In vitro transfection was performed in an A549 cell line to determine knockdown efficacy for GST-π siRNAs based on structure BU2' (SEQ ID NOs: 133 and 159). Dose dependent knockdown of GST-π mRNA was observed with the GST-π siRNAs based on structure BU2', as shown in Table 16.

TABLE 16

Dose dependent knockdown of GST-π mRNA in an A549 cell line for GST-π siRNAs based on structure BU2'

| GST-π siRNA structure | IC50 (pM) |
| --- | --- |
| BU2 with no 2'-F deoxynucleotides (SEQ ID NOs: 63 and 128) | 31 |
| BU2 with seven 2'-F deoxynucleotides, one in position 1 at the 3'end of the antisense strand (SEQ ID NOs: 150 and 176) | 3 |
| BU2 with four 2'-F deoxynucleotides, one in position 1 at the 3'end of the antisense strand (SEQ ID NOs: 149 and 175) | 11 |
| BU2 with one 2'-F deoxynucleotide in position 1 at the 3'end of the antisense strand (SEQ ID NOs: 146 and 172) | 13 |

As shown in Table 16, the activities of GST-π siRNAs based on structure BU2' having one or more 2'-F deoxynucleotides were surprisingly increased by up to 10-fold, as compared to a GST-π siRNA without 2'-F deoxynucleotides.

These data show that GST-π siRNAs having a structure with one or more 2'-F deoxynucleotides provided unexpectedly increased gene knockdown activity as compared to a GST-a siRNA without a 2'-F deoxynucleotide.

The activities shown in Table 16 for GST-π siRNAs having one or more 2'-F deoxynucleotides were in the range 3 to 13 pM, which is exceptionally suitable for many uses, including as a drug agent to be used in vivo.

Example 8

The structure of GST-π siRNAs containing one or more 2'-deoxy-2'-fluoro substituted nucleotides provided unexpectedly increased gene knockdown activity in vitro.

In vitro transfection was performed in an A549 cell line to determine knockdown efficacy for GST-π siRNAs based on structure B13' (SEQ ID NOs:209 and 224). Dose dependent knockdown of GST-π mRNA was observed with the GST-π siRNAs based on structure B13', as shown in Table 17.

TABLE 17

Dose dependent knockdown of GST-π mRNA in an A549 cell line for GST-π siRNAs based on structure B13'

| GST-π siRNA structure | IC50 (pM) |
|---|---|
| B13 with no 2'-F deoxynucleotides (SEQ ID NOs: 52 and 117) | 17 |
| B13 with three 2'-F deoxynucleotides located in non-overhang positions (SEQ ID NOs: 221 and 236) | 6 |

As shown in Table 17, the activity of a GST-t siRNA based on structure B13' having three 2'-F deoxynucleotides located in non-overhang positions was surprisingly increased by about 3-fold, as compared to a GST-π siRNA without 2'-F deoxynucleotides.

These data show that GST-π siRNAs having a structure with one or more 2'-F deoxynucleotides provided unexpectedly increased gene knockdown activity as compared to a GST-π siRNA without a 2'-F deoxynucleotide.

The activity shown in Table 17 for GST-π siRNAs having one or more 2'-F deoxynucleotides was in the picomolar range at 6 pM, which is exceptionally suitable for many uses, including as a drug agent to be used in vivo.

Example 9

Orthotopic A549 lung cancer mouse model. The GST-π siRNAs of this invention can exhibit profound reduction of orthotopic lung cancer tumors in vivo. In this example, a GST-π siRNA provided gene knockdown potency in vivo when administered in a liposomal formulation to the orthotopic lung cancer tumors in athymic nude mice.

In general, an orthotopic tumor model can exhibit direct clinical relevance for drug efficacy and potency, as well as improved predictive ability. In the orthotopic tumor model, tumor cells are implanted directly into the same kind of organ from which the cells originated.

The anti-tumor efficacy of the siRNA formulation against human lung cancer A549 was evaluated by comparing the final primary tumor weights measured at necropsy for the treatment group and the vehicle control group.

FIG. 1 shows orthotopic lung cancer tumor inhibition in vivo for a GST-π siRNA based on structure BU2 (SEQ ID NOs:63 and 128). An orthotopic A549 lung cancer mouse model was utilized with a relatively low dose at 2 mg/kg of the siRNA targeted to GST-π.

The GST-π siRNA showed significant and unexpectedly advantageous lung tumor inhibition efficacy in this six-week study. As shown in FIG. 1, after 43 days, the GST-π siRNA showed markedly advantageous tumor inhibition efficacy, with final tumor average weights significantly reduced by 2.8-fold as compared to control.

For this study, male NCr nu/nu mice, 5-6 weeks old, were used. The experimental animals were maintained in a HEPA filtered environment during the experimental period. The siRNA formulations were stored at 4° C. before use, and warmed to room temperature 10 minutes prior to injection in mouse.

For this A549 human lung cancer orthotopic model, on the day of surgical orthotopic implantation (SOI), the stock tumors were harvested from the subcutaneous site of animals bearing A549 tumor xenograft and placed in RPMI-1640 medium. Necrotic tissues were removed and viable tissues were cut into 1.5-2 mm$^3$ pieces. The animals were anesthetized with isoflurane inhalation and the surgical area was sterilized with iodine and alcohol. A transverse incision approximately 1.5 cm long was made in the left chest wall of the mouse using a pair of surgical scissors. An intercostal incision was made between the third and the fourth rib and the left lung was exposed. One A549 tumor fragment was transplanted to the surface of the lung with an 8-0 surgical suture (nylon). The chest wall was closed with a 6-0 surgical suture (silk). The lung was re-inflated by intrathoracic puncture using a 3 cc syringe with a 25 G×1½ needle to draw out the remaining air in the chest cavity. The chest wall was closed with a 6-0 surgical silk suture. All procedures of the operation described above were performed with a 7× magnification microscope under HEPA filtered laminar flow hoods.

Three days after tumor implantation, the model tumor-bearing mice were randomly divided into groups of ten mice per group. For the group of interest, treatment of the ten mice was initiated three days after tumor implantation.

For the group of interest, the formulation was (Ionizable lipid:cholesterol:DOPE:DOPC:DPPE-PEG-2K:DSPE-PEG-2K), a liposomal composition. The liposomes encapsulated the GST-π siRNA.

For the study endpoint, the experimental mice were sacrificed forty-two days after treatment initiation. Primary tumors were excised and weighed on an electronic balance for subsequent analysis.

For an estimation of compound toxicity, the mean body weight of the mice in the treated and control groups was maintained within the normal range during the entire experimental period. Other symptoms of toxicity were not observed in the mice.

Example 10

The GST-π siRNAs of this invention exhibited profound reduction of cancer xenograft tumors in vivo. The GST-π siRNAs provided gene knockdown potency in vivo when administered in a liposomal formulation to the cancer xenograft tumors.

Figure 2:
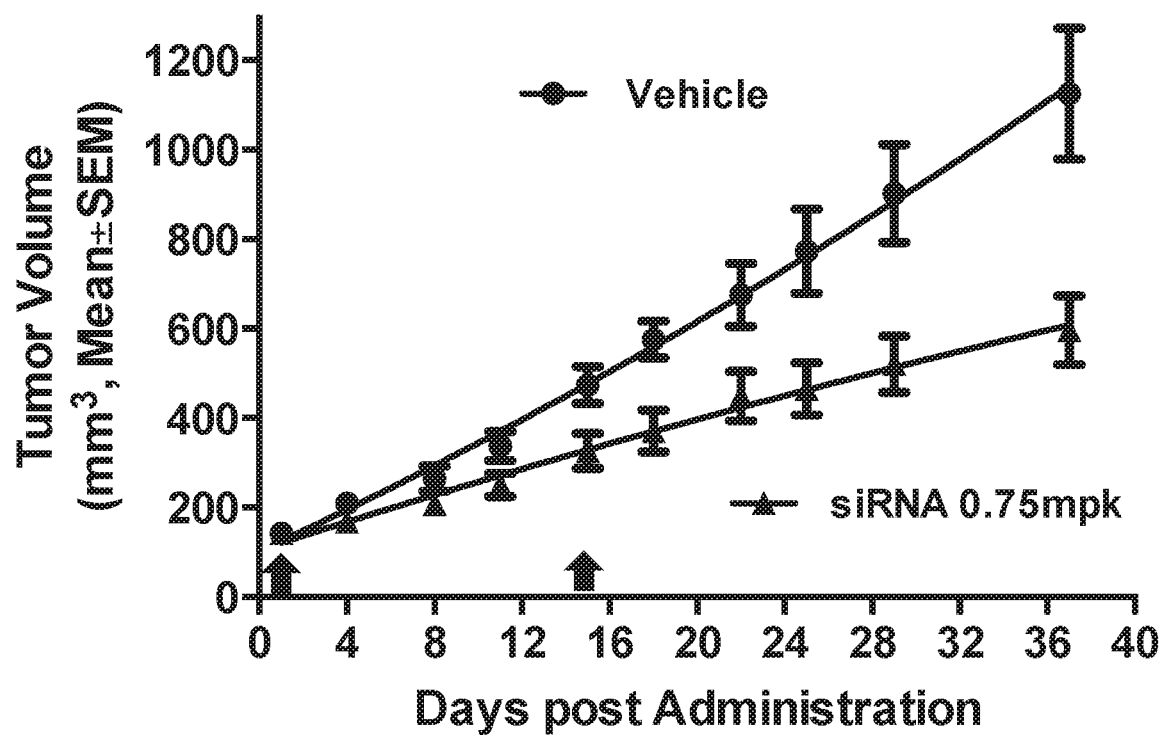
FIG. 2.

FIG. 2 shows tumor inhibition efficacy for a GST-π siRNA (SEQ ID Nos: 158 and 184). A cancer xenograft model was utilized with a relatively low dose at 0.75 mg/kg of siRNA targeted to GST-π.

The GST-π siRNA showed significant and unexpectedly advantageous tumor inhibition efficacy within a few days after administration. After 36 days, the GST-π siRNA showed markedly advantageous tumor inhibition efficacy, with tumor volume reduced by 2-fold as compared to control.

Figure 3:
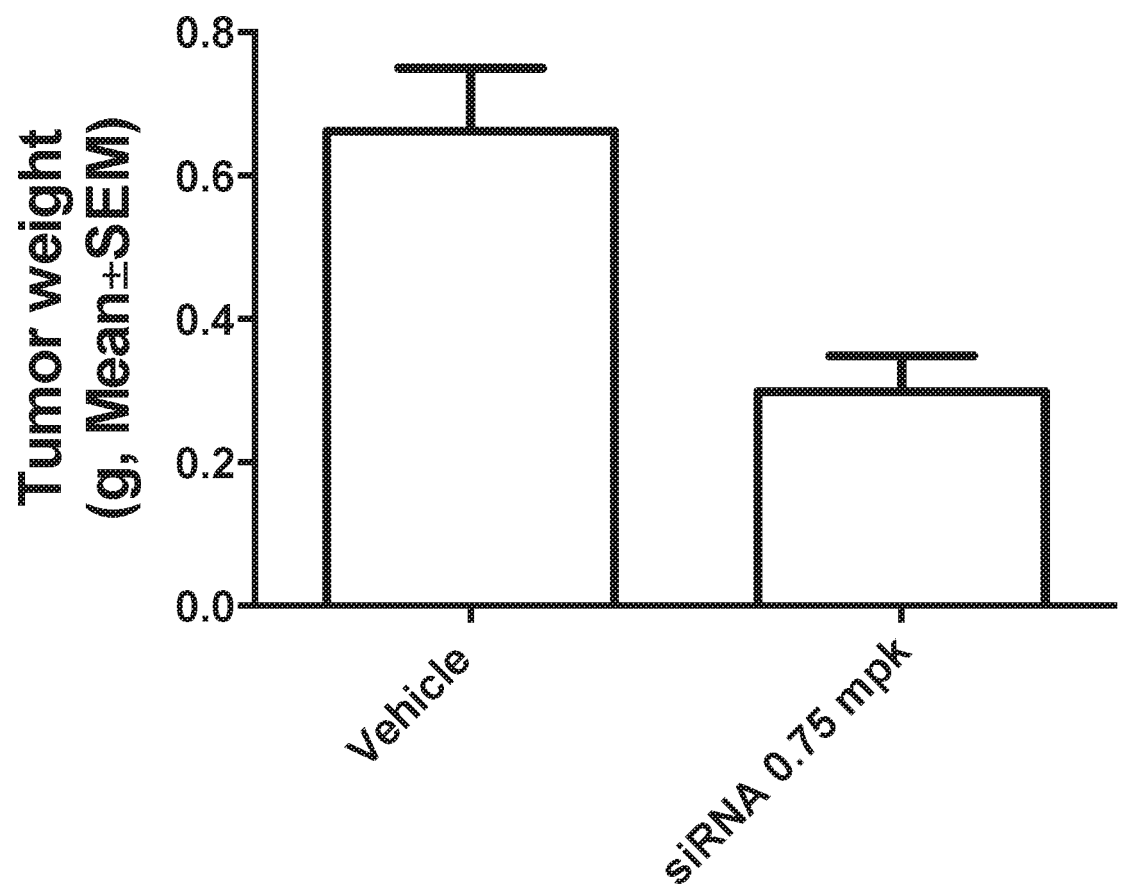
FIG. 3.

As shown in FIG. 3, the GST-π siRNA demonstrated significant and unexpectedly advantageous tumor inhibition efficacy at the endpoint day. In particular, tumor weight was reduced by more than 2-fold.

The GST-π siRNA was administered in two injections (day 1 and 15) of a liposomal formulation having the composition (Ionizable lipid:Cholesterol:DOPE:DOPC: DPPE-PEG-2K) (25:30:20:20:5).

For the cancer xenograft model, an A549 cell line was obtained from ATCC. The cells were maintained in culture medium supplemented with 10% Fetal Bovine Serum and 100 U/ml penicillin and 100 µg/ml streptomycin. Cells were split 48 hrs before inoculation so that cells were in log phase growth when harvested. Cells were lightly trypsinized with trypsin-EDTA and harvested from tissue culture. The number of viable cells was counted and determined in a hemocytometer in the presence of trypan blue (only viable cells are counted). The cells were resuspended to a concentration of $5 \times 10^7$/ml in media without serum. Then the cell suspension was mixed well with ice thawed BD matrigel at 1:1 ratio for injection.

Mice were Charles River Laboratory Athymic Nude (nu/nu) Female Mice, immuno-compromised, 6-8 weeks old, 7-8 mice per group.

For tumor model preparation, each mouse was inoculated subcutaneously in the right flank with 0.1 ml an inoculum of $2.5 \times 10^6$ of A549 cells using a 25 G needle and syringe, one inoculum per mouse. Mice were not anesthetized for inoculation.

For tumor volume measurements and randomization, tumor size was measured to the nearest 0.1 mm. Tumor volumes were calculated using the formula: Tumor volume=length×width$^2$/2. Once the established tumors reached approximately 120-175 mm$^3$, average tumor volume was about 150 mm$^3$, the mice were assigned into the various vehicle control and treatment groups such that the mean tumor volumes in the treated groups were within 10% of the mean tumor volume in the vehicle control group, ideally, the CV % of tumor volume was less than 25%. On the same day, test articles and control vehicle were administered according to the dosing regimen. Tumor volumes were monitored three times for week 1, twice for the rest of weeks, including the day of study termination.

For dosage administration, on the dosing day, the test articles were taken out from −80° C. freezer and thawed on ice. Before applied to syringes, the bottle containing formulation was reverted by hands for a few times. All test articles were dosed at 0.75 mg/kg by IV, q2w×2, at 10 ml/kg.

For body weight, mice were weighed to the nearest 0.1 g. Body weights were monitored and recorded daily within 7 days post dosing for first dose. Body weights were monitored and recorded twice for weeks, for the rest of weeks, including the day of study termination.

For tumors collection, on 28 days post first dosing, tumor volume was measured, and tumor was dissected for weight measurement, and stored for PD biomarker study. Tumor weight was recorded.

Example 11

The GST-π siRNAs of this invention demonstrated increased cancer cell death by apoptosis of cancer cells in vitro. The GST-π siRNAs provided GST-π knockdown, which resulted in upregulation of PUMA, a biomarker for apoptosis and associated with loss in cell viability.

GST-a siRNA SEQ ID NOs:158 and 184, which contained a combination of deoxynucleotides in the seed region, a 2'-F substituted deoxynucleotide, and 2'-OMe substituted ribonucleotides, provided unexpectedly increased apoptosis of cancer cells.

Figure 4:
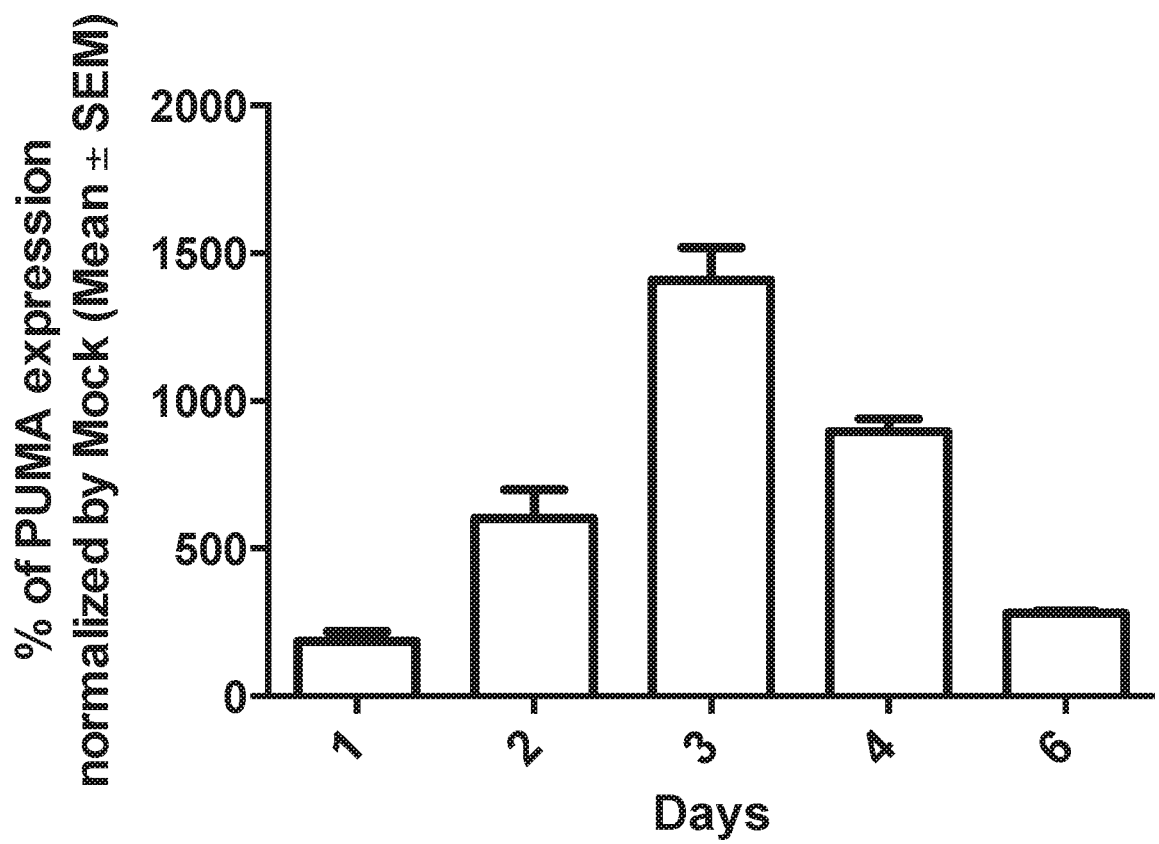
FIG. 4.

The level of expression of PUMA for GST-π siRNA SEQ ID NOs: 158 and 184 was measured as shown in FIG. 4. In FIG. 4, the expression of PUMA was greatly increased from 2-4 days after transfection of the GST-π siRNA.

These data show that the structure of GST-π siRNAs containing a combination of deoxynucleotides in the seed region, a 2'-F substituted deoxynucleotide, and 2'-OMe substituted ribonucleotides provided unexpectedly increased apoptosis of cancer cells.

The protocol for the PUMA biomarker was as follows. One day before transfection, cells were plated in a 96-well plate at $2 \times 10^3$ cells per well with 100 µl of DMEM (HyClone Cat. #SH30243.01) containing 10% FBS and cultured in a 37° C. incubator containing a humidified atmosphere of 5% CO2 in air. Next day, before transfection the medium was replaced with 90 µl of Opti-MEM I Reduced Serum Medium (Life Technologies Cat. #31985-070) containing 2% FBS. Then, 0.2 µl of Lipofectamine RNAiMAX (Life Technologies Cat. #13778-100) were mixed with 4.8 µl of Opti-MEM I for 5 minutes at room temperature. 1 µl of the GST-π siRNA (stock conc. 1 µM) was mixed with 4 µl of Opti-MEM I and combined with the RNAiMAX solution and then mixed gently. The mixture was incubated for 10 minutes at room temperature to allow the RNA-RNAiMAX complexes to form. 10 µl of RNA-RNAiMAX complexes were added per well, to final concentration of the siRNA 10 nM. The cells were incubated for 2 hours and medium changed to fresh Opti-MEM I Reduced Serum Medium containing 2% FBS. For 1, 2, 3, 4, and 6 days post transfection, the cells were washed with ice-cold PBS once and then lysed with 50 µl of Cell-to-Ct Lysis Buffer (Life Technologies Cat. #4391851 C) for 5-30 minutes at room temperature. 5 µl of Stop Solution was added and incubated for 2 minutes at room temperature. PUMA (BBC3, Cat #Hs00248075, Life Technologies) mRNA levels were measured by qPCR with TAQMAN.

Example 12

The GST-π siRNAs of this invention can exhibit profound reduction of cancer xenograft tumors in vivo. The GST-π siRNAs can provide gene knockdown potency in vivo when administered in a liposomal formulation to the cancer xenograft tumors.

Figure 5:
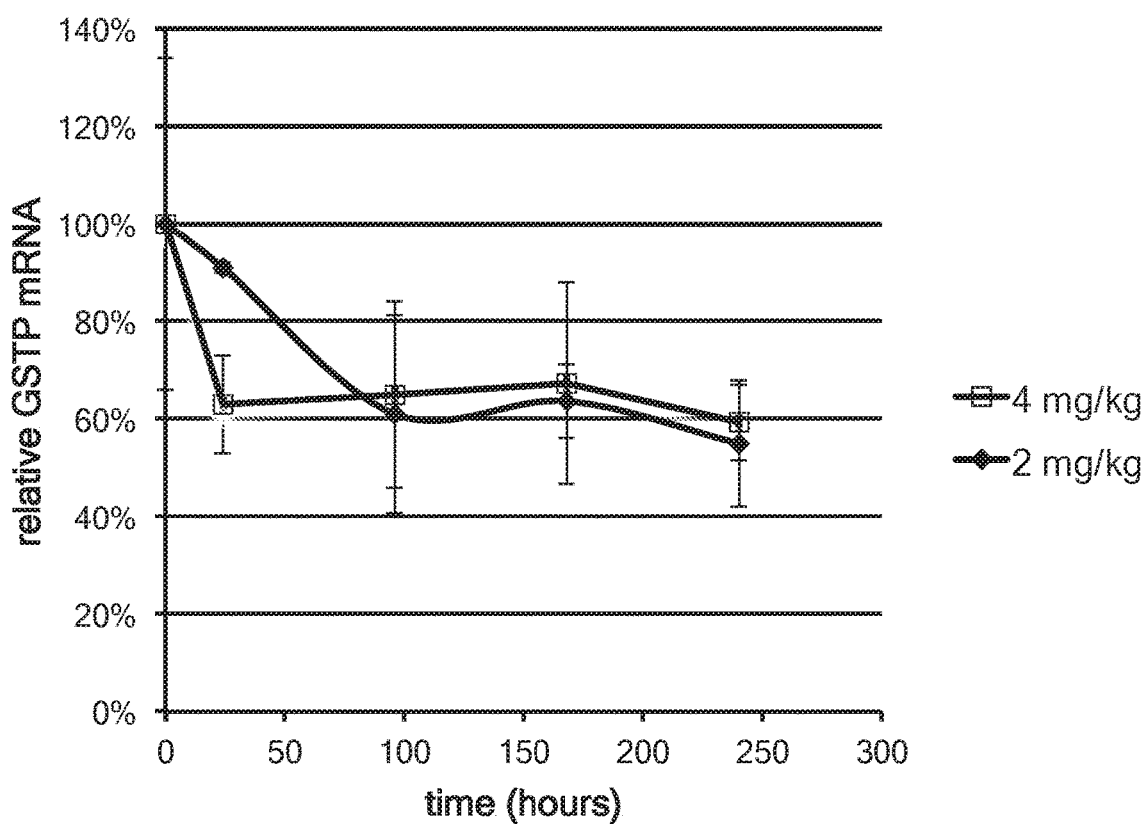
FIG. 5.

FIG. 5 shows tumor inhibition efficacy for a GST-π siRNA (SEQ ID NOs:63 and 128). Dose dependent knockdown of GST-π mRNA was observed in vivo with the siRNA targeted to GST-π. A cancer xenograft model was utilized with a relatively low dose at 0.75 mg/kg of siRNA targeted to GST-π.

The GST-π siRNA showed significant and unexpectedly advantageous tumor inhibition efficacy within a few days after administration. As shown in FIG. 5, treatment with a GST-π siRNA resulted in significant reduction of GST-π mRNA expression 4 days after injection in a lipid formulation. At the higher dose of 4 mg/kg, significant reduction of about 40/o was detected 24 hours after injection.

The GST-π siRNA was administered in a single injection of 10 mL/kg of a liposomal formulation having the composition (Ionizable lipid:Cholesterol:DOPE:DOPC:DPPE-PEG-2K) (25:30:20:20:5).

For the cancer xenograft model, an A549 cell line was obtained from ATCC. The cells were maintained in RPMI-1640 supplemented with 100% Fetal Bovine Serum and 100

U/ml penicillin and 100 μg/ml streptomycin. Cells were split 48 hrs before inoculation so that cells were in log phase growth when harvested. Cells were lightly trypsinized with trypsin-EDTA and harvested from tissue culture. The number of viable cells was counted and determined in a hemocytometer in the presence of trypan blue (only viable cells are counted). The cells were resuspended to a concentration of 4×10$^7$/ml in RPMI media without serum. Then the cell suspension was mixed well with ice thawed BD matrigel at 1:1 ratio for injection.

Mice were Charles River Laboratory Athymic Nude (nu/nu) Female Mice, immuno-compromised, 6-8 weeks old, 3 mice per group.

For tumor model preparation, each mouse was inoculated subcutaneously in the right flank with 0.1 ml an inoculum of 2×10$^6$ of A549 cells using a 25 G needle and syringe, one inoculum per mouse. Mice were not anesthetized for inoculation.

For tumor volume measurements and randomization, tumor size was measured to the nearest 0.1 mm. Tumor volumes were calculated using the formula: Tumor volume=length×width$^2$/2. Tumor volumes were monitored twice a week. Once the established tumors reached approximately 350-600 mm$^3$, the mice were assigned into groups with varied time points. On the same day, test articles were administered according to the dosing regimen.

For dosage administration, on the day when the established tumors reached approximately 350-600 mm$^3$, the test articles were taken out from 4° C. fridge. Before being applied to syringes, the bottle containing formulation was reverted by hand for a few times to make a homogeneous solution.

For body weight, mice were weighed to the nearest 0.1 g. Body weights were monitored and recorded twice for weeks, for the rest of weeks, including the day of study termination.

For tumors collection, animals were sacrificed by overdosed CO$_2$ and tumors were dissected at 0, 24, 48, 72, 96(optional), and 168 hours following the dosing. Tumors were first wet weighted, and then separated into three parts for KD, distribution and biomarker analysis. The samples were snap frozen in liquid nitrogen and stored at −80° C. until ready to be processed.

Example 13

The GST-π siRNAs of this invention inhibited pancreatic cancer xenograft tumors in vivo. The GST-π siRNAs provided gene knockdown potency in vivo when administered in a liposomal formulation to the pancreatic cancer xenograft tumors.

In this xenograft model, each mouse was inoculated subcutaneously in the right flank with 0.1 ml an inoculum of 2.5×10$^6$ of PANC-1 cells. Athymic nude female mice, 6 to 8 weeks, Charles River, were used. Tumor size was measured to the nearest 0.1 mm. Once the established tumors reached approximately 150-250 mm$^3$ (average tumor volume at about 200 mm$^3$), the mice were assigned into the various vehicle control and treatment groups such that the mean tumor volumes in the treated groups were within 10% of the mean tumor volume in the vehicle control group. On the same day, test articles and control vehicle were administered according to the dosing regimen. Tumor volumes were monitored three times for week 1, twice for the rest of weeks, including the day of study termination.

Figure 6:
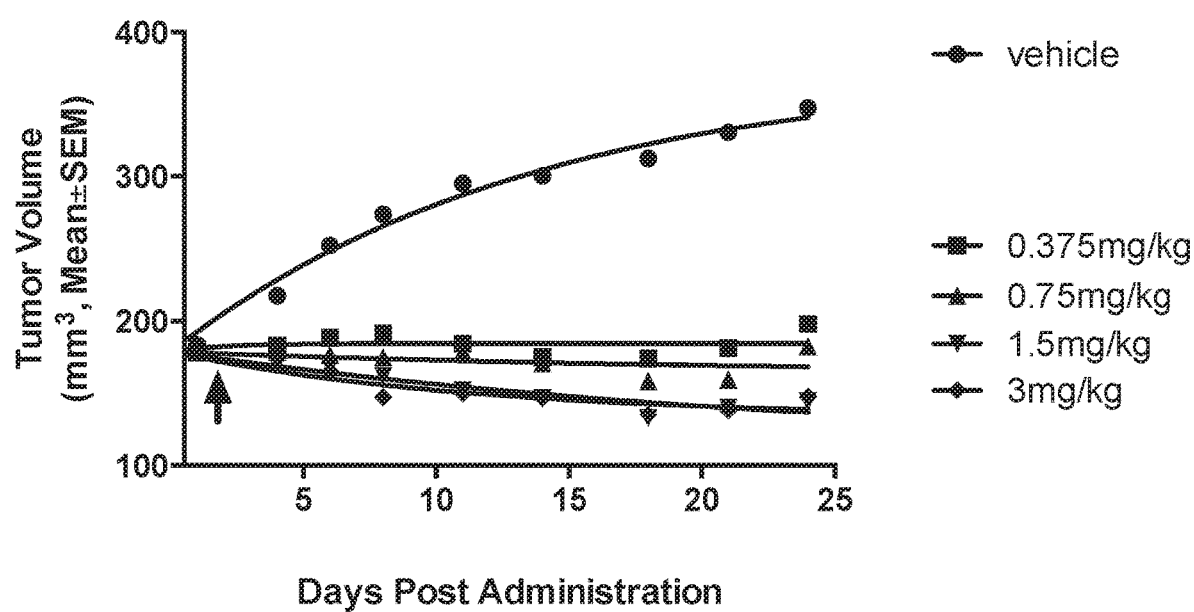
FIG. 6.

FIG. 6 shows tumor inhibition efficacy for a GST-R siRNA (SEQ ID Nos:63 and 128). As shown in FIG. 6, a dose response was obtained with doses ranging from 0.375 mg/kg to 3 mg/kg of siRNA targeted to GST-π. The GST-π siRNA showed significant and unexpectedly advantageous tumor inhibition efficacy within a few days after administration. Thus, the GST-π siRNA demonstrated significant and unexpectedly advantageous tumor inhibition efficacy at the endpoint.

The GST-π siRNAs were administered in a liposomal formulation having the composition (Ionizable lipid:cholesterol:DOPE:DOPC:DPPE-PEG-2K) (25:30:20:20:5).

Example 14

The GST-π siRNAs of this invention exhibited increased serum stability.

Figure 7:
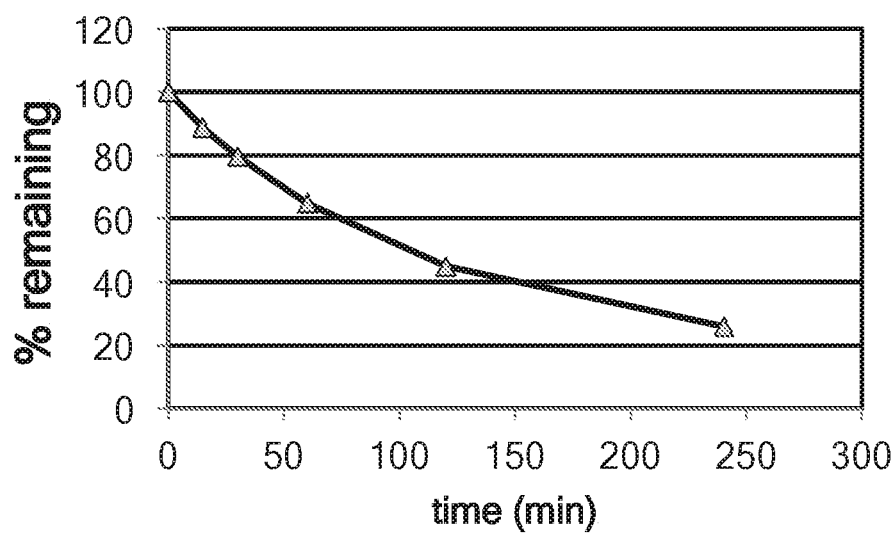
FIG. 7.
Figure 7:
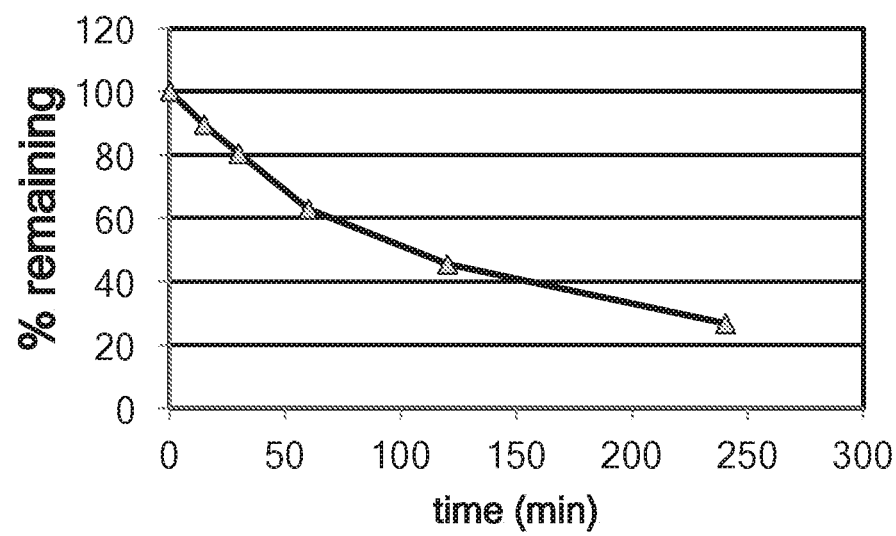

FIG. 7 shows incubation in human serum and detection of remaining siRNA at various time points by HPLS/LCMS. As shown in FIG. 7, the half-life (t$_{1/2}$) in serum for both the sense strand (FIG. 7, top) and antisense strand (FIG. 7, bottom) of a GST-π siRNA (SEQ ID Nos:63 and 128) was about 100 minutes.

Example 15

The GST-π siRNAs of this invention exhibited enhanced stability in formulation in plasma.

Figure 8:
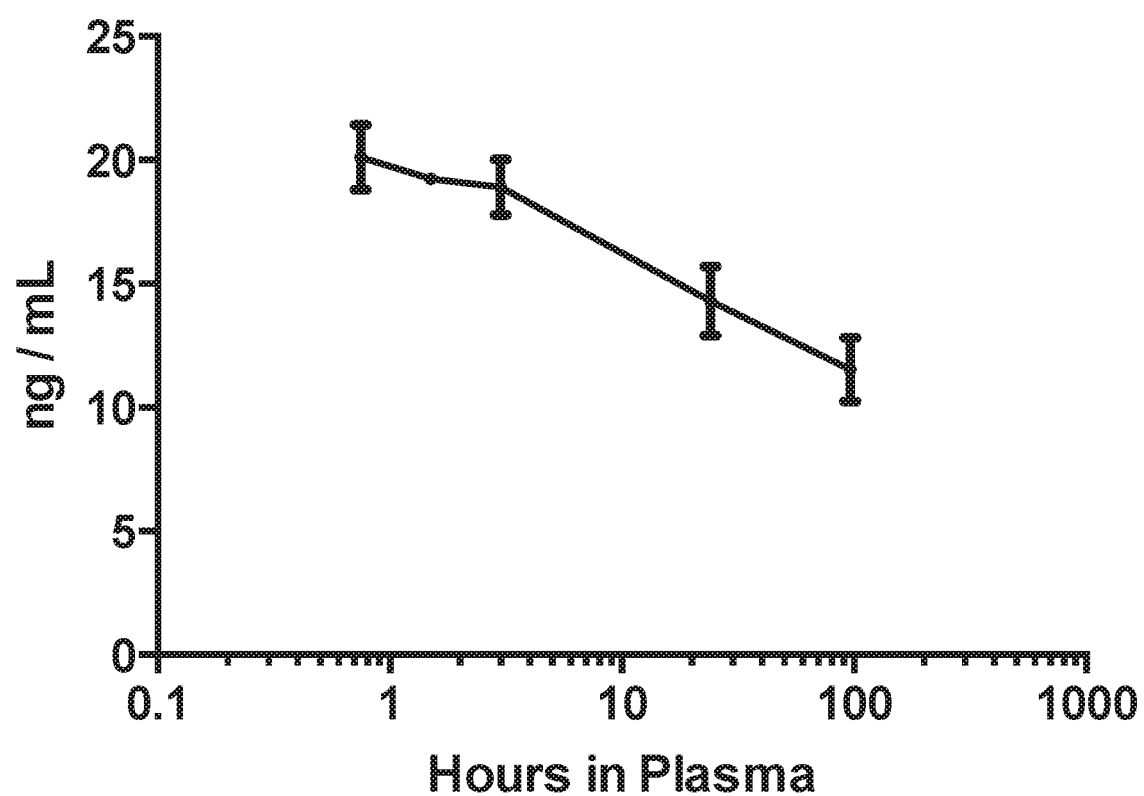
FIG. 8.

FIG. 8 shows incubation of formulation in plasma and detection of remaining siRNA at various time points. As shown in FIG. 8, the half-life (t$_{1/2}$) in plasma of a formulation of GST-π siRNA (SEQ ID Nos:63 and 128) was significantly longer than 100 hours.

The GST-π siRNA was prepared in a liposomal formulation having the composition (Ionizing lipid:cholesterol:DOPE:DOPC:DPPE-PEG-2K) (25:30:20:20:5). The z-average size for the liposomal nanparticles was 40.0 nm, and the siRNA was 91% encapsulated.

The formulation was incubated in 50% human serum in PBS for 40 min, 1.5 h, 3 h, 24 h, and 96 h. The amount of the GST-π siRNA was determined by an ELISA-based assay.

Example 16

The GST-π siRNAs of this invention exhibited reduced off target effects by the passenger strand.

Figure 9:
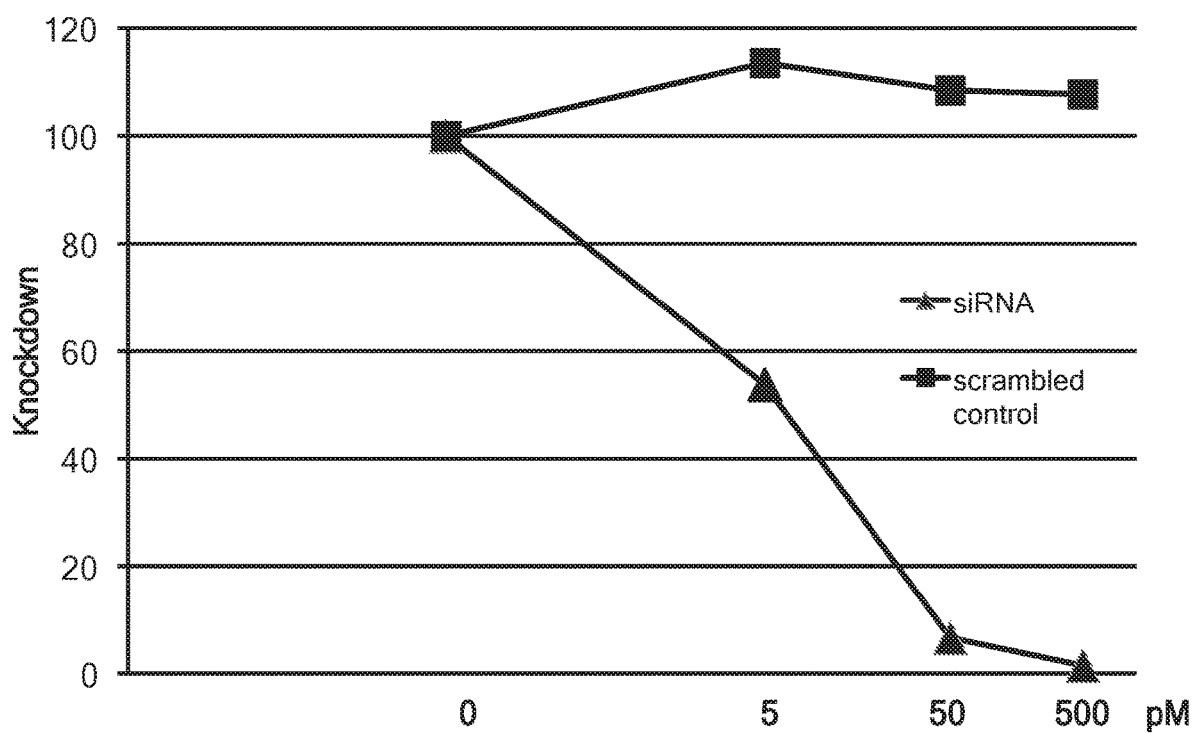
FIG. 9.
Figure 10:
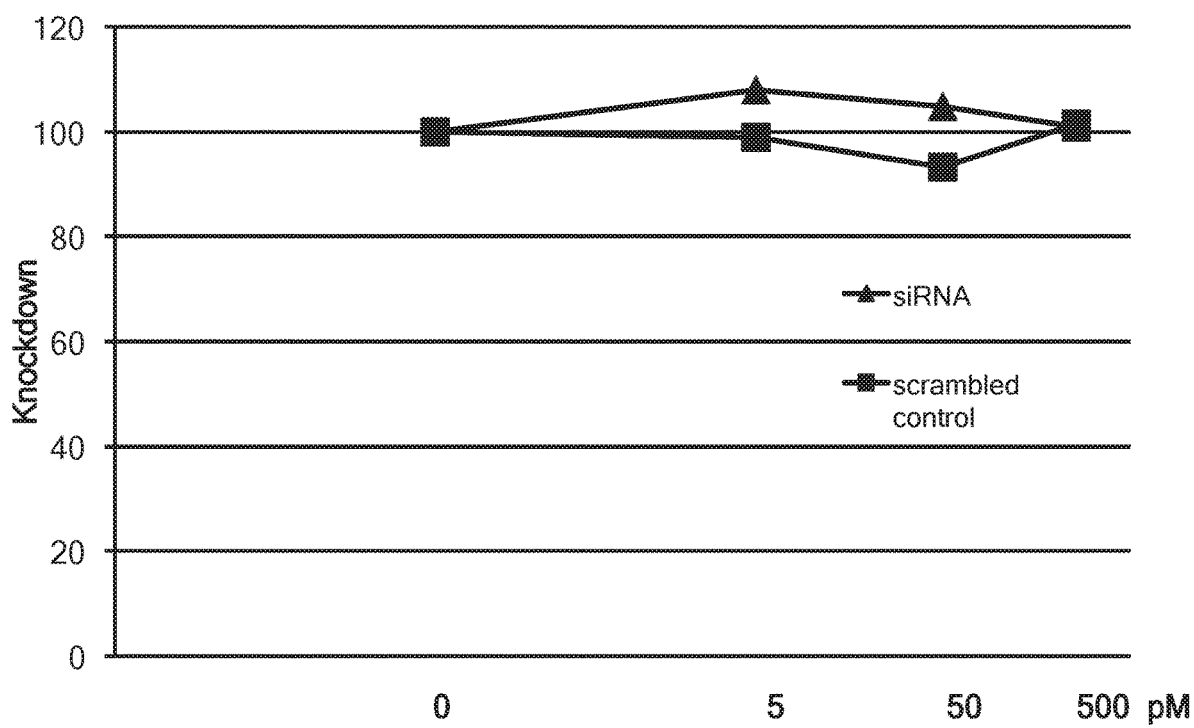
FIG. 10.

For the GST-π siRNA (SEQ ID Nos:158 and 184), FIG. 9 shows that in vitro knockdown for the guide strand was approximately exponential, as compared to a control with scrambled sequence that exhibited no effect. The IC50 of this siRNA was measured at 5 pM. FIG. 10 shows in vitro knockdown for the passenger strand of the same GST-π siRNA. As shown in FIG. 10, the passenger strand off target knockdown for the GST-π siRNA was greatly reduced, by more than 100-fold.

Figure 11:
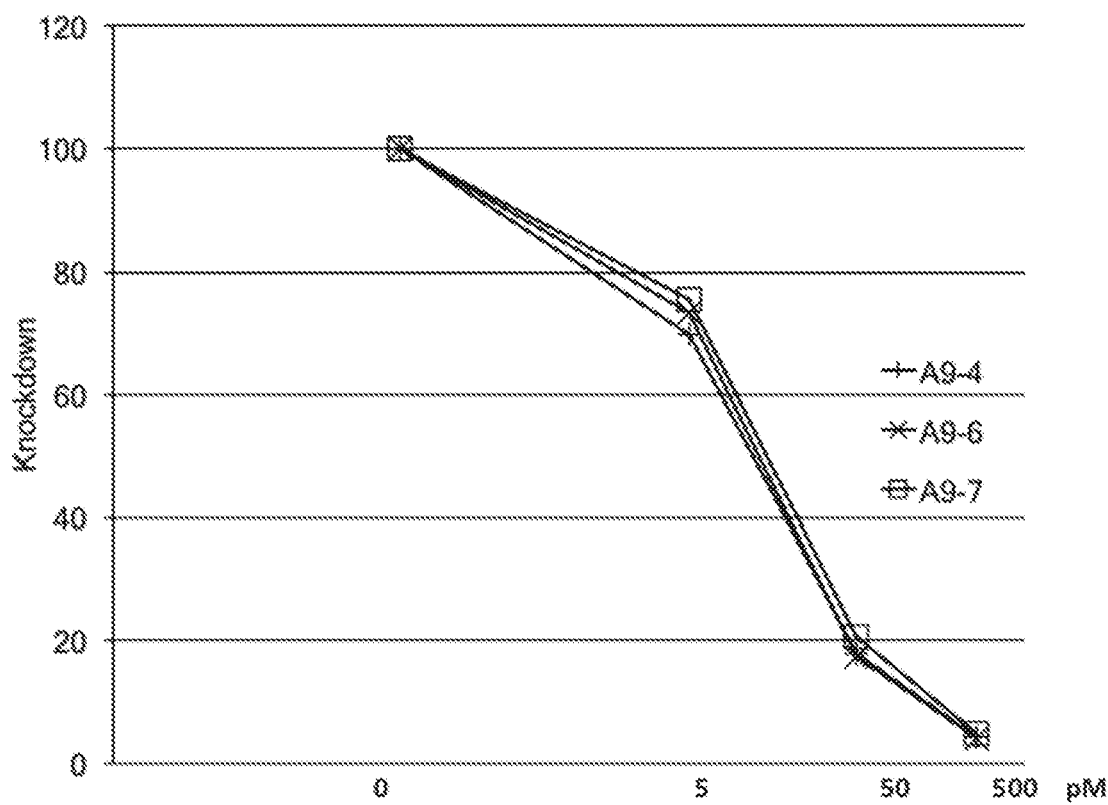
FIG. 11.
Figure 12:
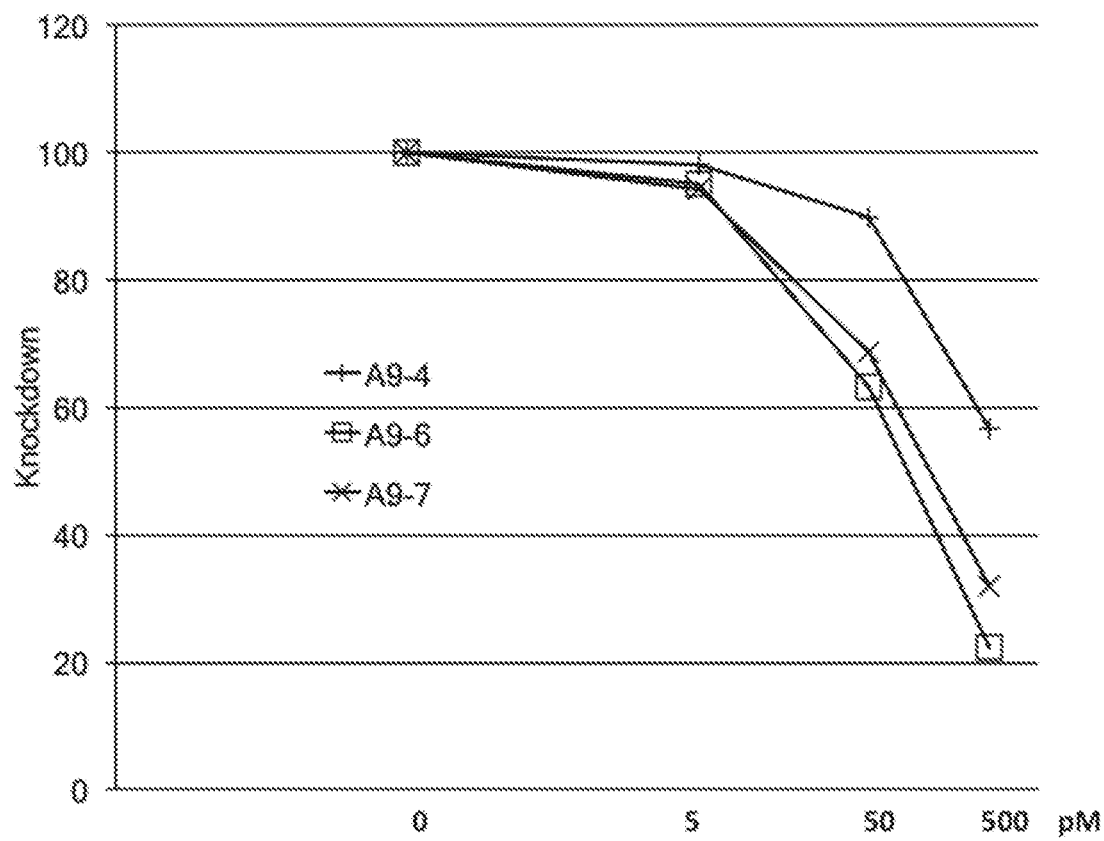
FIG. 12.

For the GST-π siRNAs (SEQ ID Nos:189 and 201), (SEQ ID Nos:191 and 203), and (SEQ ID Nos:192 and 204), FIG. 11 shows that the in vitro knockdowns for the guide strands were approximately exponential. The IC50s of these siRNAs were measured at 6, 7, and 5 pM, respectively. As shown in FIG. 12, the in vitro knockdowns for the passenger strands of these GST-π siRNAs were significantly reduced by at least 10-fold. All of these GST-π siRNAs had deoxynucleotides in the seed region of the duplex region, with no other modifications in the duplex region.

Figure 13:
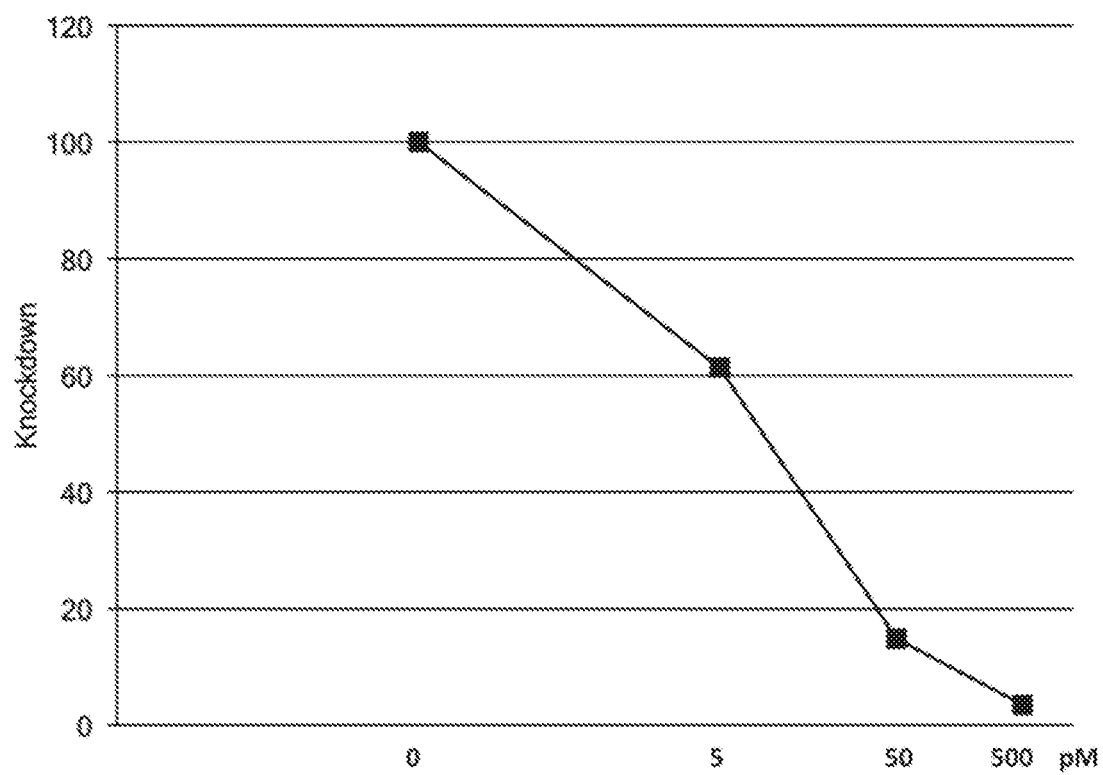
FIG. 13.
Figure 14:
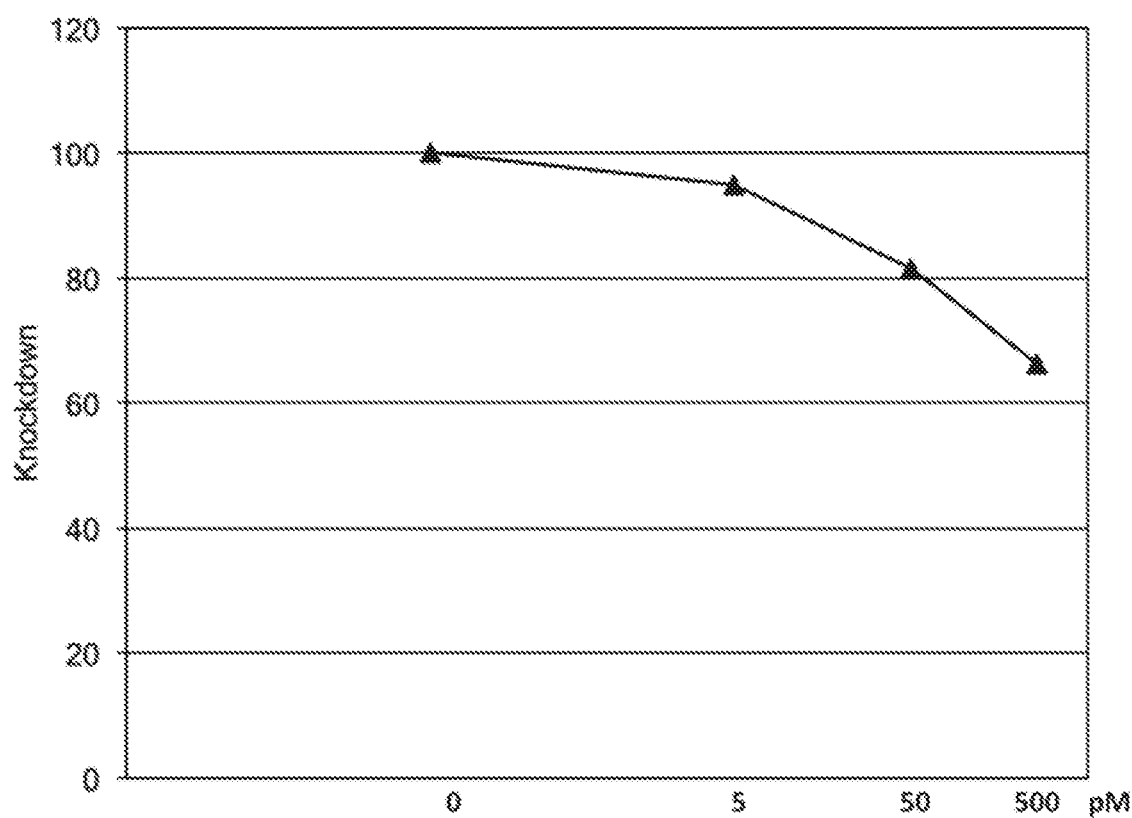
FIG. 14.

For the GST-π siRNAs (SEQ ID Nos:219 and 234), FIG. 13 shows that the in vitro knockdown for the guide strand of this highly active GST-π siRNA was approximately exponential. The IC50 of this siRNA was measured at 11 pM. As shown in FIG. 14, the in vitro knockdown for the passenger strand of this GST-a siRNA was significantly reduced by more than 100-fold. This GST-π siRNA had deoxynucleotides in the seed region of the duplex region, with no other modifications in the duplex region.

Off-target effects were determined using the expression reporter plasmid psiCHECK-2, which encodes the *Renilla* luciferase gene. (Dual-Luciferase Reporter Assay System, Promega, Cat #:E1960). The siRNA concentration was typically 50 pM. Protocol: Day 1, HeLa cell seeded at 5 to 7.5×103/100 ul/well. Day 2, co-transfection with cell confluence about 80%. Day 3, cells harvested for luciferase activity measurement. Luciferase activity was measured using Promega's Luciferase Assay System (E4550), according to manufacturer's protocol.

The psiCHECK-2 vector enabled monitoring of changes in expression of a target gene fused to the reporter gene of *Renilla* luciferase. The siRNA constructs were cloned into the multiple cloning region, and the vector was cotransfected with the siRNA into HeLa cells. If a specific siRNA binds to the target mRNA and initiates the RNAi process, the fused *Renilla* luciferase: construct mRNA will be cleaved and subsequently degraded, decreasing the *Renilla* luciferase signal.

For example, the plasmid inserts for siRNAs with the BU2' structure were as follows:

```
PsiCHECK-2 (F) plasmid insert:
                                    SEQ ID NO.: 288
ctcgag gggcaacTGAAGCCTTTTGAGACCCTGcTgTcccag gcggccgc PsiCHECK-2 (R) plasmid insert:
                                    SEQ ID NO.: 289
ctcgag cTgggacagCAGGGTCTCAAAAGGCTTCagTTgccc gcggccgc
```

Example 17

The GST-π siRNAs of this invention exhibited advantageously reduced miRNA-like off target effects, which are seed-dependent unintended off-target gene silencing.

For the GST-π siRNAs (SEQ ID Nos:158 and 184), (SEQ ID Nos:189 and 201), (SEQ ID Nos:191 and 203), (SEQ ID Nos:192 and 204), and (SEQ ID Nos:219 and 234), off target activity mimicking miRNA was found to be essentially negligible. The seed-dependent unintended off-target gene silencing for these GST-a siRNAs was at least 10-fold to 100-fold less than the on-target activity of the guide strand.

For testing miRNA-related off target effects, one to four repeats of seed-matched target sequences complementary to the entire seed-containing region, positions 1-8 of the 5' end of the antisense strand, but not to the remaining non-seed region, positions 9-21, were introduced into the region corresponding to the 3'UTR of the luciferase mRNA, to determine the efficiency of the seed-dependent unintended off-target effects. Plasmid inserts were used to mimic a miRNA with complete matching in the seed region and mismatches (bulges) in the non-seed region.

For example, the plasmid inserts for siRNAs with the BU2' structure were as follows:

```
PsiCHECK-2 (Fmi1) plasmid insert:
                                    SEQ ID NO.: 290
ctcgag gggcaacTCTACGCAAAACAGACCCTGcTgTcccag gcggccgc
```

```
-continued
PsiCHECK-2 (Fmi2) plasmid insert:
                                    SEQ ID NO.: 291
ctcgag gggcaacTCTACGCAAAACAGACCCTGcT CTACGCAAAACAGACCCTGcT gTcccag gcggccgc PsiCHECK-2 (Fmi3) plasmid insert:
                                    SEQ ID NO.: 292
ctcgag gggcaacTCTACGCAAAACAGACCCTGcT CTACGCAAAACAGACCCTGcT CTACGCAAAACAGACCCTGcT gTcccag gcggccgc PsiCHECK-2 (Fmi4) plasmid insert:
                                    SEQ ID NO.: 293
ctcgag gggcaacTCTACGCAAAACAGACCCTGcT CTACGCAAAACAGACCCTGcT CTACGCAAAACAGACCCTGcT CTACGCAAAACAGACCCTGcT gTcccag gcggccgc
```

Example 18

Examples of RNAi molecules of this invention targeted to GST-π mRNA are shown in Table 18.

TABLE 18

| RNAi molecule sequences for GST-π | | | | |
|---|---|---|---|---|
| | | SENSE STRAND | | ANTISENSE STRAND |
| SEQ ID (A9) | SEQ ID NO | (5'→3') SEQ ID NOS: 294 to 297 | SEQ ID NO | (5'→3') SEQ ID NOS: 298 to 301 |
| 21 | 294 | CCUUUUGAGAC CCUGCUGUUU | 298 | ACAgCaGgGUC UCAAAAGGUU |
| 22 | 295 | CCUUUUGAGAC CCUGCUGUUU | 299 | ACAgCaGgGUC UCAAAAGGUU |
| 23 | 296 | CCUUUUGAGAC CCUGCUGUUU | 300 | ACAgCaGgGUC UCAAAAGGUU |
| 24 | 297 | CCUUUUGAGAC CCUGCUGUUU | 301 | ACAgCaGgGUC UCAAAAGGUU |

Key for Table 18: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., U.

The structure of GST-π siRNAs of Table 18 provided unexpectedly increased gene knockdown activity in vitro. In vitro transfection was performed in an A549 cell line to determine knockdown efficacy for GST-π siRNAs of Table 18, which are based on structure A9. Dose dependent knockdown of GST-π mRNA was observed with the GST-π siRNAs of Table 18, as shown in Table 19.

TABLE 19

Dose dependent knockdown of GST-π mRNA in an A549 cell line for GST-π siRNAs based on structure B13'

| GST-π siRNA structure | IC50 (pM) |
|---|---|
| A9 (SEQ ID NOs: 294 and 298) | 4 |
| A9 (SEQ ID NOs: 295 and 299) | 28 |
| A9 (SEQ ID NOs: 296 and 300) | 12 |
| A9 (SEQ ID NOs: 297 and 301) | 7 |

Figure 15:
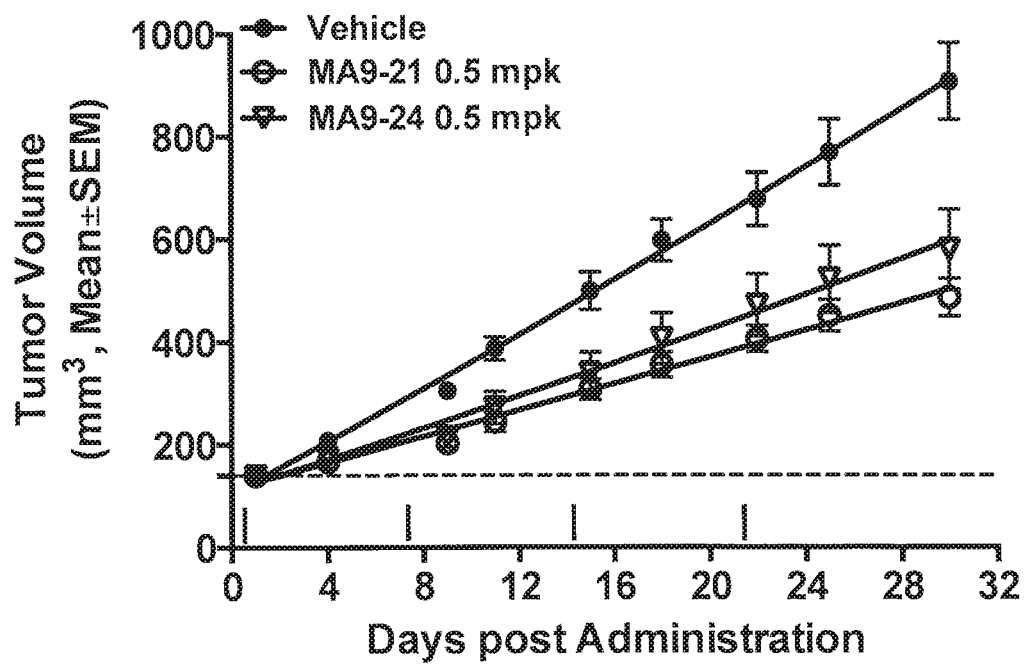
FIG. 15.

The structure of GST-π siRNAs of Table 18 provided unexpectedly increased tumor inhibition efficacy in vivo. FIG. 15 shows tumor inhibition efficacy in vivo for GST-a siRNAs having structure based on siRNA A9: (SEQ ID NOs:294 and 298) and (SEQ ID NOs:297 and 301). A cancer xenograft model using A549 cells was utilized with a relatively low dose of siRNA at 0.5 mg/kg. The GST-π siRNAs showed advantageous tumor inhibition within a few days. After 36 days, the GST-π siRNAs showed markedly advantageous tumor inhibition, with final tumor average volumes significantly reduced by about 2-fold, as compared to control.

Example 19

Examples of RNAi molecules of this invention targeted to GST-π mRNA are shown in Table 20.

TABLE 20

RNAi molecule sequences for GST-π

| ID (B13) | SEQ ID NO | SENSE STRAND (5'→3') SEQ ID NOS: 302 to 303 | SEQ ID NO | ANTISENSE STRAND (5'→3') SEQ ID NOS: 304 to 305 |
|---|---|---|---|---|
| 21 | 302 | GGAUGACUAU<u>G</u><br>U<u>G</u>AAGGCAU<u>U</u> | 304 | UGCcUuCaCAU<br>AGUCAUCC<u>UU</u> |
| 22 | 303 | GGAUGACUAU<u>G</u><br>UGAAGG<u>C</u>AU<u>U</u> | 305 | UGCcUuCaCAU<br>AGUCAUCC<u>UU</u> |

Key for Table 20: Upper case A, G, C and U refer to ribo-A, ribo-G, ribo-C and ribo-U, respectively. The lower case letters a, u, g, c, t refer to 2'-deoxy-A, 2'-deoxy-U, 2'-deoxy-G, 2'-deoxy-C, and deoxythymidine (dT=T=t) respectively. Underlining refers to 2'-OMe-substituted, e.g., <u>U</u>.

The structure of GST-π siRNAs of Table 18 provided unexpectedly increased gene knockdown activity in vitro. In vitro transfection was performed in an A549 cell line to determine knockdown efficacy for GST-π siRNAs of Table 20, which are based on structure B13. Dose dependent knockdown of GST-π mRNA was observed with the GST-π siRNAs of Table 20, as shown in Table 21.

TABLE 21

Dose dependent knockdown of GST-π mRNA in an A549 cell line for GST-π siRNAs based on structure B13'

| GST-π siRNA structure | IC50 (pM) |
|---|---|
| B13 (SEQ ID NOs: 302 and 304) | 6 |
| B13 (SEQ ID NOs: 303 and 305) | 5 |

Figure 16:
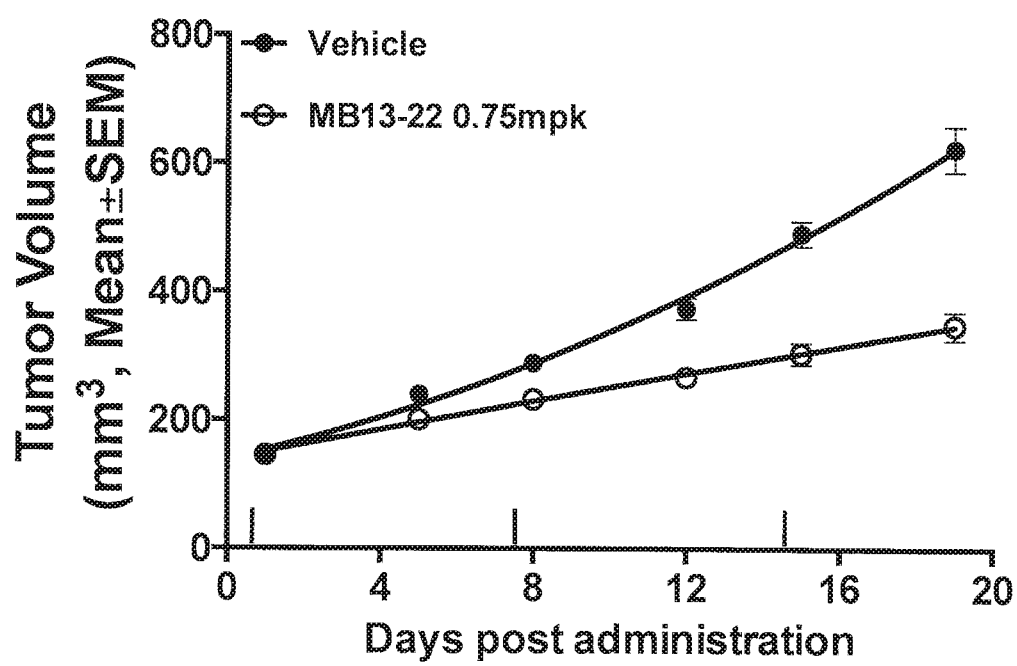
FIG. 16.

The structure of GST-π siRNAs of Table 20 provided unexpectedly increased tumor inhibition efficacy in vivo. FIG. 16 shows tumor inhibition efficacy in vivo for a GST-π siRNA having structure based on siRNA B13: (SEQ ID NOs:303 and 305). A cancer xenograft model using A549 cells was utilized with a relatively low dose of siRNA at 0.75 mg/kg in a formulation with HEPES buffer. The GST-π siRNA showed advantageous tumor inhibition within a few days. After 36 days, the GST-π siRNA showed markedly advantageous tumor inhibition, with final tumor average volumes significantly reduced by about 2-fold, as compared to control.

Additional Definitions

The terms used in this specification generally have their ordinary meanings in the art, within the context of the invention, and in the specific context where each term is used, and no special significance is to be placed upon whether or not a term is elaborated upon, or discussed herein. The descriptions of examples in this disclosure are illustrative only, and in no way limit the scope and meaning of the invention.

Unless otherwise defined, all technical and scientific terms used herein have the same meaning as commonly understood by one of ordinary skill in the art to which this invention pertains. The following references can provide a general definition of certain terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991).

A "neoplasia" can refer to any disease that is caused by, or results in inappropriately high levels of cell division, inappropriately low levels of apoptosis, or both. For example, cancer is an example of a neoplasia. Examples of cancers include leukemias, e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia, polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioepdotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and still more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "inhibitory nucleic acid" is meant a single or double-stranded RNA, siRNA (short interfering RNA), shRNA (short hairpin RNA), or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises or corresponds to at least a portion of a target nucleic acid molecule, or an ortholog thereof, or comprises at least a portion of the complementary strand of a target nucleic acid molecule.

By "antisense nucleic acid", it is meant a non-enzymatic nucleic acid molecule that binds to target RNA by means of RNA-RNA or RNA-DNA interactions and alters the activity of the target RNA (for a review, see Stein et al. 1993; Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk N A et al., 1999; Delihas N et al., 1997; Aboul-Fadl T, 2005.)

The term "siRNA" refers to small interfering RNA; a siRNA is a double stranded RNA that "corresponds" to or matches a reference or target gene sequence. This matching need not be perfect so long as each strand of the siRNA is capable of binding to at least a portion of the target sequence. siRNAs can be used to inhibit gene expression, see for example Bass, 2001, Nature, 411, 428 429; Elbashir et al., 2001, Nature, 411, 494 498; and Zamore et al., Cell 101:25-33 (2000).

The embodiments described herein are not limiting and one skilled in the art can readily appreciate that specific combinations of the modifications described herein can be tested without undue experimentation toward identifying nucleic acid molecules with improved RNAi activity.

All publications, patents and literature specifically mentioned herein are incorporated by reference in their entirety for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention. It will be readily apparent to one skilled in the art that varying substitutions and modifications can be made to the description disclosed herein without departing from the scope and spirit of the description, and that those embodiments are within the scope of this description and the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably, and shall be read expansively and without limitation.

Recitation of ranges of values herein are merely intended to serve as a shorthand method of referring individually to each separate value falling within the range, unless otherwise indicated herein, and each separate value is incorporated into the specification as if it were individually recited herein. For Markush groups, those skilled in the art will recognize that this description includes the individual members, as well as subgroups of the members of the Markush group.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A method for preventing, treating or ameliorating one or more symptoms of a malignant tumor associated with KRAS mutation in a mammal in need thereof, the method consisting of:
   identifying a tumor cell in the mammal, the tumor cell comprising at least one of: (i) a mutation of a KRAS gene, and (ii) an aberrant expression level of KRAS protein compared to a non-tumor cell of the same tissue; and
   administering to the mammal a therapeutically effective amount of a composition comprising one or more RNAi molecules that are active in reducing expression of GST-π, wherein the composition comprises only one active ingredient and the active ingredient is the RNAi molecules,
   wherein the tumor cell comprises an increased level of expression of wild type KRAS protein compared to that in a non-tumor cell of the same tissue, and
   wherein the malignant tumor is a carcinoma selected from the group consisting of lung adenocarcinoma, mucinous adenoma, ductal carcinoma of the pancreas, colorectal carcinoma, breast cancer, and fibrosarcoma.

2. The method of claim 1, wherein the mammal is a human and the GST-π is a human GST-π.

3. The method of claim 1, wherein the RNAi molecule is a siRNA or shRNA.

4. The method of claim 1, wherein the RNAi molecules comprise a duplex region comprising a nucleotide sequence corresponding to a target sequence of SEQ ID NO:287.

5. The method of claim 1, wherein the RNAi molecule decreases expression of GST-π in the mammal.

6. The method of claim 1, wherein the administration decreases expression of GST-π in the tumor cell by at least 5% for at least 5 days.

7. The method of claim 1, wherein the administration decreases the volume of the malignant tumor in the mammal by at least 5%, or at least 10%, or at least 20%, or at least 30%, or at least 40%, or at least 50%.

8. The method of claim 1, wherein the method reduces one or more symptoms of the malignant tumor, or delays or terminates the progression of the malignant tumor.

9. The method of claim 1, wherein the administration reduces growth of malignant tumor cells in the subject.

10. The method of claim 1, wherein the administration reduces growth for at least 2%, or at least 5%, or at least 10%, or at least 15%, or at least 20% of the malignant tumor cells in the subject.

11. The method of claim 1, wherein the tumor cell over-expresses wild-type GST-π RNA or protein compared to non-tumor cells of the same tissue.

12. The method of claim 1, wherein the tumor cell comprises a mutation in a KRAS protein at one or more of residues 12, 13 and 61.

13. The method of claim 1, wherein the tumor cell comprises a mutation in a KRAS protein and the tumor is a cancer selected from lung cancer, colon cancer, and pancreatic cancer.

14. The method of claim 1, wherein the malignant tumor is located in an anatomical region selected from the group of lung, colon, pancreas, gallbladder, liver, breast, and any combination thereof.

15. The method of claim 1, wherein the administration is performed from 1 to 12 times per day.

16. The method of claim 1, wherein the administration is performed for a duration of 1, 2, 3, 4, 5, 6 or 7 days.

17. The method of claim 1, wherein the administration is performed for a duration of 1, 2, 3, 4, 5, 6, 8, 10 or 12 weeks.

18. The method of claim 1, wherein the administration is a dose of from 0.01 to 2 mg/kg of the RNAi molecules at least once per day for a period up to twelve weeks.

19. The method of claim 1, wherein the administration provides a mean AUC(0-last) of from 1 to 1000 ug*min/mL and a mean $C_{max}$ of from 0.1 to 50 ug/mL for the GST-π RNAi molecule.

20. The method of claim 1, wherein the administration is intravenous injection, intradermal injection, subcutaneous injection, intramuscular injection, intraperitoneal injection, oral, topical, infusion, or inhalation.

* * * * *

UNITED STATES PATENT AND TRADEMARK OFFICE
CERTIFICATE OF CORRECTION

PATENT NO. : 11,352,628 B2
APPLICATION NO. : 16/540973
DATED : June 7, 2022
INVENTOR(S) : Kenjirou Minomi It is certified that error appears in the above-identified patent and that said Letters Patent is hereby corrected as shown below:

On the Title Page

Page 2, Column 1 (Other Publications) Line 9, delete "{GST)" and insert -- {GST} --.

Page 2, Column 1 (Other Publications) Line 31, delete "[online]." and insert -- [online]. --.

Page 2, Column 1 (Other Publications) Line 31, delete "2016)." and insert -- 2016]. --.

Page 2, Column 2 (Other Publications) Line 7, delete "2016)." and insert -- 2016}. --.

Page 2, Column 2 (Other Publications) Line 10, delete "{Sequenom)" and insert -- {Sequenom} --.

Page 2, Column 2 (Other Publications) Line 13, delete "G0761423," and insert -- GO761423, --.

Page 2, Column 2 (Other Publications) Line 16, delete "G0761423>." and insert -- GO761423>. --.

Page 2, Column 2 (Other Publications) Line 17, delete "G0786145," and insert -- GO786145, --.

Page 2, Column 2 (Other Publications) Line 18, delete "5-,.mRNA" and insert -- 5-, mRNA --.

Page 2, Column 2 (Other Publications) Line 18, delete "[online]." and insert -- [online]. --.

Page 2, Column 2 (Other Publications) Line 20, delete "G0786145>." and insert -- GO786145>. --.

Page 2, Column 2 (Other Publications) Line 30, delete "resonse," and insert -- response, --.

Page 2, Column 2 (Other Publications) Line 47, delete "U S A.," and insert -- U. S. A., --.

Page 2, Column 2 (Other Publications) Line 64, delete "{GSTP1 )" and insert -- {GSTP1} --.

Signed and Sealed this
Twentieth Day of June, 2023

Katherine Kelly Vidal
*Director of the United States Patent and Trademark Office*

CERTIFICATE OF CORRECTION (continued)
U.S. Pat. No. 11,352,628 B2

Page 2, Column 2 (Other Publications) Line 65, delete "J_" and insert -- J. --.

Page 3, Column 1 (Other Publications) Line 9, delete "Jlutathione" and insert -- Glutathione --.

Page 3, Column 1 (Other Publications) Line 22, delete "{GSTP1)" and insert -- {GSTP1} --.

Page 3, Column 1 (Other Publications) Line 32, delete "Japanes;" and insert -- Japanese; --.

Page 3, Column 2 (Other Publications) Line 2, delete "porr" and insert -- poor --.

Page 3, Column 2 (Other Publications) Line 30, delete "ER" and insert -- EP --.

In the Specification

Column 8, Line 15 (approx.), delete "etc." and insert -- etc.) --.

Column 8, Line 19, delete ""GST-π:" and insert -- "GST-π --.

Column 8 (Table 1), Line 1, delete "cf" and insert -- of --.

Column 8 (Table 1), Line 1, delete "GSTπ" and insert -- GST-π --.

Column 8 (Table 1), Line 10, delete "tctttcgcta" and insert -- tctttcgctg --.

Column 9-10 (Table 1-continued), Line 1, delete "GSTπ" and insert -- GST-π --.

Column 9-10 (Table 1-continued), Line 14, delete "caatccttcc" and insert -- caatccttgc --.

Column 9-10 (Table 1-continued), Line 19, delete "acctccgctc" and insert -- acctccgctg --.

Column 9-10 (Table 1-continued), Line 30, delete "catggacagg" and insert -- gatggacagg --.

Column 11-12 (Table 1-continued), Line 1, delete "GSTπ" and insert -- GST-π --.

Column 11, Line 53 (approx.), delete "pylocytic" and insert -- pilocytic --.

Column 25-26 (Table 9), Line 6, delete "actggggcgc" and insert -- actggggcgg --.

Column 25-26 (Table 9), Line 6, delete "agcggagcgg" and insert -- agcggggcgg --.

Column 25-26 (Table 9), Line 7, delete "gcagtttccc" and insert -- ggagtttcgc --.

Column 25-26 (Table 9), Line 12, delete "gcaggagcca" and insert -- gcaggaggca --.

Column 26, Line 61, delete "74).)." and insert -- 74). --.

CERTIFICATE OF CORRECTION (continued)
U.S. Pat. No. 11,352,628 B2

Column 30, Line 52, delete "intracistemal," and insert -- intracisternal, --.

Column 31, Line 27, delete "Lippincourt" and insert -- Lippincott --.

Column 31, Line 32, delete "napthalenes." and insert -- naphthalenes. --.

Column 31, Line 67, delete "GST-a" and insert -- GST-$\pi$ --.

Column 33, Line 47, delete "GST-a" and insert -- GST-$\pi$ --.

Column 33, Line 66, delete "GST-a" and insert -- GST-$\pi$ --.

Column 34, Line 4 (approx.), delete "structure structure" and insert -- structure --.

Column 34, Line 41 (approx.), delete "GST-a" and insert -- GST-$\pi$ --.

Column 36, Line 6 (approx.), delete "regioin" and insert -- region --.

Column 36, Line 67, delete "GST-a" and insert -- GST-$\pi$ --.

Column 37, Line 28, delete "GST-t" and insert -- GST-$\pi$ --.

Column 39, Line 66, delete "GST-a" and insert -- GST-$\pi$ --.

Column 40, Line 60, delete "40/o" and insert -- 40% --.

Column 40, Line 67, delete "100%" and insert -- 10% --.

Column 41, Line 65, delete "GST-R" and insert -- GST-$\pi$ --.

Column 42, Line 34, delete "nanparticles" and insert -- nanoparticles --.

Column 43, Line 2, delete "GST-a" and insert -- GST-$\pi$ --.

Column 43, Line 47, delete "GST-a" and insert -- GST-$\pi$ --.

Column 45, Line 3, delete "GST-a" and insert -- GST-$\pi$ --.

Column 46, Line 37-38, delete "lymphangioepdotheliosarcoma," and insert -- lymphangioendotheliosarcoma, --.

Column 46, Line 45, delete "nile" and insert -- bile --.

Column 46, Line 46, delete "Wilm's" and insert -- Wilms --.

Column 46, Line 51, delete "oligodenroglioma," and insert -- oligodendroglioma, --.

Column 47, Line 49 (approx.), delete "2005.)" and insert -- 2005. --.

SEQUENCE LISTING

<160> NUMBER OF SEQ ID NOS: 305

<210> SEQ ID NO 1
<211> LENGTH: 3594
<212> TYPE: DNA
<213> ORGANISM: Homo sapiens

<400> SEQUENCE: 1

```
gtggctcacc tgtacccagc acttgggaag ccgaggcgtg cagatcacct aagtcaggag      60
ttcgagacca gcccggccaa catggtgaaa ccccgtctct actaaaaata caaaaatcag     120
```

```
ccagatgtgg cacgcaccta tatccaccta ctcgggaggc tgaagcagaa tgcttaaccc    180
gagaggcgga ggttgcagtg agccgcccag atcgcgccac tgcactccag cctgggccac    240
agcgtgagac tactcataaa ataaaataaa ataaaataaa ataaaataaa ataaaataaa    300
ataataaaat aaaataaaat aaaataaaat ataaaataaa ataaaataaa ataaaataaa    360
ataaaataaa ataaaagcaa tttccttttcc tctaagcggc ctccacccct ctccctgcc    420 ctgtgaacgg gggaagctcc ggatcgcagc aattagggaa tttcccccg cgatgtcccg     480 gcgcgccagt tcggcgcaca tctttcgctg cggtcctctt cctgctgtct gtttactccc    540
taggcccctg gacctgggaa agagggaaag gcttcccgcc agctgcgcgg cgactccggg    600
gactccaggg cgcccctctg cggcgacgcc cgggtgcagc ggccgccggg ctggggccgg    660
cgggactccg cgggaccctc cagaagagcg gccggcggct gactcagcac tggggcggag    720
gggcgggaca cccttataag gctcggagcg cgagccttcg ctggagtttc gccgccgcag    780
tcttcgccac cagtgagtac gcggccgcgt ccccggggat ggggctcaga gctccagcat    840
ggggccaacc cgcagcatca ggccgggctc ccggcggcct ccccacctcg agacccggga    900
cggggcctag ggacccagg acgtcccagt gccgttagcg gctttcaggg ggcccggagc    960
gcctcgggga gggatgggac cccggggcg ggagggcagc tcactcaccg cgccttggca   1020
tcctccccgg gctccacaaa ttttctttgt tcgctgcagt gccgccctac accgtggtct   1080
atttcccagt tcgaggtagg agcatgtgtc tggcagggaa gggaggcagg ggctgggct    1140 gcagcaccca cagcccccac ccggagagat ccgaaccccc ttatccctcg tcgtgtgctt   1200 ttaccccgg cctccttcct gttccccgcc ctcccgcca tgcctgctcc ccgcccagt      1260 gttgtgtgaa atcttcggag gaacctgttt ccctgttccc tcctgcact cctgacccct    1320 ccccgggttg ctgcgaggcg gagtcggccc ggtccccaca tctcgtactt ctccctcccc   1380
gcaggccgct gcgcggccct gcgcatgctg ctggcagatc agggccagag ctggaaggag   1440
gaggtggtga ccgtggagac gtggcaggag ggctcactca aagcctcctg cgtaagtgac   1500
catgcccggg caaggggagg gggtgctggg ccttaggggg ctgtgactag gatcgggga    1560 cgccccaagc tcagtgcccc tccctgagcc atgcctcccc caacagctat acgggcagct   1620
ccccaagttc caggacggag acctcaccct gtaccagtcc aataccatcc tgcgtcacct   1680
gggccgcacc cttggtgagt cttgaacctc caagtccagg gcaggcatgg gcaagcctct   1740
gcccccggag cccttttgtt taaatcagct gccccgcagc cctctggagt ggaggaaact   1800
gagacccact gaggttacgt agtttgccca aggtcaagcc tggtgcctg caatccttgc    1860 cctgtgccag gctgcctccc aggtgtcagg tgagctctga gcacctgctg tgtggcagtc   1920
tctcatcctt ccacgcacat cctcttcccc tcctcccagg ctggggctca cagacagccc   1980
cctggttggc ccatccccag tgactgtgtt gatcaggcgc ccagtcacgc ggcctgctcc   2040
cctccaccca accccagggc tctatgggaa ggaccagcag gaggcagccc tggtggacat   2100
ggtgaatgac ggcgtggagg acctccgctg caaatacatc tccctcatct acaccaacta   2160
tgtgagcatc tgcaccaggg ttgggcactg ggggctgaac aaagaaaggg gcttcttgtg   2220
ccctcacccc ccttacccct caggtggctt ggctgaccc cttcttgggt cagggtgcag    2280
gggctgggtc agctctgggc caggggggcc tgggacaaga cacaacctgc acccttattg   2340
cctgggacat caaccaccca agtaacgggt catggggcg agtgcaagga cagagacctc   2400
cagcaactgt tggtttctgc tctcctgggg tggccagagg tggaggagga tttgtgccag   2460
tttctggatg gagccgctgg cgcttttagc tgaggaaaat atgagacaca gagcactttg   2520
```

-continued

```
ggtaccaggg accagttcag cagaggcagc gtgtgtggcg tgtgtgtgcg tgtgtgtgcg    2580
tgtgtgtgtg tacgcttgca tttgtgtcgg gtgggtaagg agatagagat ggggcggcag    2640
taggcccagg tcccgaaggc cttgaaccca ctggtttgga gtctcctaag ggcaatgggg    2700
gccattgaga agtctgaaca gggctgtgtc tgaatgtgag gtctagaagg atcctccaga    2760
gaagccagct ctaaagcttt tgcaatcatc tggtgagaga acccagcaag gatggacagg    2820
cagaatggaa tagagatgag ttggcagctg aagtggacag gatttggtac tagcctggtt    2880
gtggggagca agcagaggag aatctgggac tctggtgtct ggcctggggc agacggggt     2940 gtctcagggc tgggaggga tgagagtagg atgatacatg gtgtgtgctg gcaggaggcg     3000
ggcaaggatg actatgtgaa ggcactgccc gggcaactga agccttttga ccctgctg      3060 tcccagaacc agggaggcaa gaccttcatt gtgggagacc aggtgagcat ctggccccat    3120
gctgttcctt cctcgccacc ctctgcttcc agatggacac aggtgtgagc catttgttta    3180
gcaaagcaga gcagacctag gggatgggct taggccctct gcccccaatt cctctccagc    3240
ctgctcccgc tggctgagtc cctagccccc ctgccctgca gatctccttc gctgactaca    3300
acctgctgga cttgctgctg atccatgagg tcctagcccc tggctgcctg gatgcgttcc    3360
ccctgctctc agcatatgtg gggcgcctca gtgcccggcc caagctcaag gccttcctgg    3420
cctcccctga gtacgtgaac ctcccccatca atggcaacgg gaaacagtga gggttggggg   3480
gactctgagc gggaggcaga gtttgccttc ctttctccag gaccaataaa agggctaaga    3540
gagctactat gagcactgtg tttcctggga cggggcttag gggttctcag cctc         3594
```

<210> SEQ ID NO 2
<211> LENGTH: 189
<212> TYPE: PRT
<213> ORGANISM: Homo sapiens

<400> SEQUENCE: 2

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
ucccagaacc agggaggcat t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
cuuuugagac ccugcuguct t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
cugucccaga accagggagt t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
ugucccagaa ccagggaggt t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
aagccuuuug agacccugct t						21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
uugagacccu gcugucccat t						21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
uuuugagacc cugcugucct t						21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
gagacccugc ugucccagat t						21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
gcuggaagga ggagguggut t						21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 12
cuggaaggag gagguggugt t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
ucagggccag agcuggaagt t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
ugagacccug cugucccagt t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
agggccagag cuggaaggat t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
agcuggaagg aggagguggt t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 17
agacccugcu gucccagaat t        21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
gagcuggaag gaggaggugt t        21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
ugcuguccca gaaccagggt t        21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
cccagaacca gggaggcaat t        21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
ccagaaccag ggaggcaagt t        21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 22
uuugagaccc ugcugucccu t                                                21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
gacccugcug ucccagaact t                                                21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
gaucagggcc agagcuggau t                                                21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
agccuuuuga gacccugcut t                                                21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
gccuuuugag acccugcugt t                                                21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 27
ccuuuugaga cccugcugut t                                                  21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
cgccuuuuga gacccugcat t                                                  21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
ccuacaccgu ggucuauuut t                                                  21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
ugugggagac cagaucucct t                                                  21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
gcgggaggca gaguuugcct t                                                  21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 32 ccuucucca ggaccaauat t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
acccugcugu cccagaacct t                                             21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
ggucuauuuc ccaguucgat t                                             21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
cccuggugga cauggugaat t                                             21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
acaucucccu caucuacact t                                             21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
              oligonucleotide
<220> FEATURE:
<223> OTHER INFORMATION: Description of Combined DNA/RNA Molecule:
      Synthetic oligonucleotide

<400> SEQUENCE: 37
gcaaggauga cuaugugaat t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
ccuucgcuga cuacaaccut t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
cuggcagauc agggccagat t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
gacggagacc ucacccugut t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
cgggcaagga ugacuaugut t                                              21

<210> SEQ ID NO 42
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
cuuuugagac ccugcuguat t                                                    21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
gagcuggaag gaggagguat t                                                    21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
acccugcugu cccagaacat t                                                    21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
ugcuguccca gaaccaggat t                                                    21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
agccuuuuga gacccugcat t                                                    21

<210> SEQ ID NO 47
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
ccuuuugaga cccugcugat t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
ugaagccuuu ugagacccut t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
acugaagccu uuugagacct t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-deoxy-nucleotide

<400> SEQUENCE: 50
aaggaugacu augugaaggt t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-deoxy-nucleotide
```

```
<400> SEQUENCE: 51
aggaugacua ugugaaggct t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-deoxy-nucleotide

<400> SEQUENCE: 52
ggaugacuau gugaaggcat t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
cucccucauc uacaccaact t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
gaagccuuuu gagaccccugt t                                             21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
ucucccucau cuacaccaat t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 56
ccucaucuac accaacuaut t                                             21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
cccucaucua caccaacuat t                                             21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
caacugaagc cuuuugagat t                                             21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
aacugaagcc uuugagact t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
cugaagccuu uugagaccct t                                             21

<210> SEQ ID NO 61
<211> LENGTH: 21
<212> TYPE: DNA
<213> ORGANISM: Artificial Sequence
<220> FEATURE:

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
ucccucaucu acaccaacut t                                               21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
gcucccucau cuacaccaat t                                               21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 63
gaagccuuuu gagacccuat t                                               21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
acugaagccu uuugagacat t                                               21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
cucccucauc uacaccaaat t                                               21

<210> SEQ ID NO 66
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
ccucaucuac accaacuaat t                                                21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
accaauaaaa uuucuaagat t                                                21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
ugccucccug guucugggac a                                                21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
gacagcaggg ucucaaaagg c                                                21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
cucccugguu cuggacagc a                                                 21

<210> SEQ ID NO 71
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
ccucccuggu ucugggacag c                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
gcagggucuc aaaaggcuuc a                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
ugggacagca gggucucaaa a                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
ggacagcagg gucucaaaag g                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
ucugggacag cagggucuca a                                              21

<210> SEQ ID NO 76
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
accaccuccu ccuuccagct c                                              21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
caccaccucc uccuuccagc t                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
cuuccagcuc uggcccugat c                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
cugggacagc agggucucaa a                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
uccuuccagc ucuggcccug a                                              21

<210> SEQ ID NO 81
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
ccaccuccuc cuuccagcuc t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
uucugggaca gcagggucuc a                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
caccuccucc uuccagcuct g                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
cccugguucu gggacagcag g                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
uugccucccu gguucuggga c                                              21
```

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 86
cuugccuccc ugguucuggg a                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 87
gggacagcag ggucucaaaa g                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 88
guucugggac agcaggguct c                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 89
uccagcucug gcccugauct g                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 90
agcagggucu caaaaggcut c                                              21

```
<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 91
cagcaggguc ucaaaaggct t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
acagcagggu cucaaaaggc t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
ugcagggucu caaaaggcgt c                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94
aaauagacca cgguguaggg c                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
ggagaucugg ucucccacaa t                                              21
```

```
<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
ggcaaacucu gccucccgct c                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
uauugguccu ggagaaagga a                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
gguucuggga cagcaggguc t                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
ucgaacuggg aaauagacca c                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
```
uucaccaugu ccaccagggc t                                        21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
guguagauga gggagaugua t                                        21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
uucacauagu cauccuugcc c                                        21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
agguuguagu cagcgaagga g                                        21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
ucuggcccug aucugccagc a                                        21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
acagggugag gucuccgucc t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
acauagucau ccuugcccgc c                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
uacagcaggg ucucaaaagg c                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
uaccuccucc uuccagcuct g                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
uguucuggga cagcaggguc t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
uccugguucu gggacagcag g                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
ugcagggucu caaaaggcut c                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
ucagcagggu cucaaaaggc t                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
agggucucaa aaggcuucag t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
ggucucaaaa ggcuucagut g                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<220> FEATURE:
<221> NAME/KEY: modified_base
<222> LOCATION: (20)..(21)
<223> OTHER INFORMATION: 2'-deoxy-nucleotide

<400> SEQUENCE: 115
ccuucacaua gucauccuug c                                                    21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-deoxy-nucleotide

<400> SEQUENCE: 116
gccuucacau agucauccut g                                                    21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-deoxy-nucleotide

<400> SEQUENCE: 117
ugccuucaca uagucaucct t                                                    21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
guugguguag augagggaga t                                                    21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
```
cagggucuca aaaggcuuca g					21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
uugguguaga ugagggagat g					21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
auaguuggug uagaugaggg a					21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
uaguuggugu agaugaggga g					21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
ucucaaaagg cuucaguugc c					21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124

```
gucucaaaag gcuucaguug c                                              21
```

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125

```
gggucucaaa aggcuucagt t                                              21
```

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126

```
aguuggugua gaugagggag a                                              21
```

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127

```
uugguguaga ugagggagct g                                              21
```

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128

```
uagggucuca aaaggcuuca g                                              21
```

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 129
ugucucaaaa ggcuucagut g                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
uuugguguag augagggaga t                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
uuaguuggug uagaugaggg a                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
ucuuagaaau uuuauugguc c                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 133
gaagccuuuu gagacccuan n                                              21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic

```
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 134
gaagccuuuu gagacccuau u                                              21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 135
gaagccuuuu gagacccuau u                                              21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 136
gaagccuuuu gagacccuau u                                              21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 137
gaagccuuuu gagacccuau u                                              21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 138
gaagccuuuu gagacccuau u                                              21
```

```
<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 139
gaagccuuuu gagacccuau u                                              21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 140
gaagccuuuu gagacccuau u                                              21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 141
gaagccuuuu gagacccuau u                                              21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 142
gaagccuuuu gagacccuau u                                              21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide
```

-continued

```
<400> SEQUENCE: 143
gaagccuuuu gagacccuau u                                          21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
gaagccuuuu gagaccuat t                                           21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 145
gaagccuuuu gagacccuau u                                          21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 146
gaagccuuuu gagacccuau u                                          21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 147
gaagccuuuu gagacccuau u                                          21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 148
gaagccuuuu gagacccuau u                                              21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(19)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 149
gaagccuuuu gagacccuau u                                              21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: 2'-deoxy-2'-fluoro-nucleotide
<220> FEATURE:
<221> NAME/KEY: modified_base
<222> LOCATION: (19)..(19)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 150
gaagccuuuu gagacccuau u                                              21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: 2'-OMe-nucleotide

<400> SEQUENCE: 151
gaagccuuuu gagacccuau u                                              21

<210> SEQ ID NO 152
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: 2'-OMe-nucleotide

<400> SEQUENCE: 152
gaagccuuuu gagacccuau u                                              21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 153
gaagccuuuu gagacccuau u                                              21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 154
gaagccuuuu gagacccuau u                                              21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base

```
<222> LOCATION: (20)..(21)
<223> OTHER INFORMATION: 2'-OMe-nucleotide

<400> SEQUENCE: 155
gaagccuuuu gagacccuau u                                              21

<210> SEQ ID NO 156
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 156
gaagccuuuu gagacccuau u                                              21

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(21)
<223> OTHER INFORMATION: 2'-OMe-nucleotide

<400> SEQUENCE: 157
gaagccuuuu gagacccuau u                                              21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (1)..(3)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (18)..(21)
<223> OTHER INFORMATION: 2'-OMe-nucleotide

<400> SEQUENCE: 158
gaagccuuuu gagacccuau u                                              21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 159
uagggucuca aaaggcuucn n                                              21

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 160
uagggucuca aaaggcuucu u                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
```

```
<220> FEATURE:
<221> NAME/KEY: modified_base
<222> LOCATION: (20)..(21)
<223> OTHER INFORMATION: 2'-OMe-nucleotide

<400> SEQUENCE: 161
uagggucuca aaaggcuucu u                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 162
uagggucuca aaaggcuucu u                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 163
uagggucuca aaaggcuucu u                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
```

```
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 164
uagggucuca aaaggcuucu u                                              21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 165
uagggucuca aaaggcuucu u                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 166
uagggucuca aaaggcuucu u                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

```
<222> LOCATION: (20)..(21)
<223> OTHER INFORMATION: 2'-OMe-nucleotide

<400> SEQUENCE: 167
uagggucuca aaaggcuucu u                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 168
uagggucuca aaaggcuucu u                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 169
uagggucuca aaaggcuucu u                                              21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
```

```
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 170
uagggucuca aaaggcuucu u                                              21

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 171
uagggucuca aaaggcuucu u                                              21

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 172
uagggucuca aaaggcuucu u                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

```
<222> LOCATION: (1)..(1)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 173
uagggucuca aaaggcuucu u                                           21

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Phosphorothioate linkage
<220> FEATURE:
<221> NAME/KEY: modified_base
<222> LOCATION: (20)..(21)
<223> OTHER INFORMATION: 2'-OMe-nucleotide

<400> SEQUENCE: 174
uagggucuca aaaggcuucu u                                           21

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (9)..(9)
<223> OTHER INFORMATION: 2'-deoxy-2'-fluoro-nucleotide
<220> FEATURE:
<221> NAME/KEY: modified_base
<222> LOCATION: (17)..(17)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 175
uagggucuca aaaggcuucu u                                           21

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (9)..(9)
<223> OTHER INFORMATION: 2'-deoxy-2'-fluoro-nucleotide
<220> FEATURE:
<221> NAME/KEY: modified_base
```

```
<222> LOCATION: (11)..(12)
<223> OTHER INFORMATION: 2'-deoxy-2'-fluoro-nucleotide
<220> FEATURE:
<221> NAME/KEY: modified_base
<222> LOCATION: (17)..(17)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 176
uagggucuca aaaggcuucu u                                              21

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 177
uagggucuca aaaggcuucu u                                              21

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 178
uagggucuca aaaggcuucu u                                              21

<210> SEQ ID NO 179
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 179
uagggucuca aaaggcuucu u                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 180
uagggucuca aaaggcuucu u                                              21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide
```

```
<400> SEQUENCE: 181
uagggucuca aaaggcuucu u                                           21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 182
uagggucuca aaaggcuucu u                                           21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
```

```
<220> FEATURE:
<221> NAME/KEY: modified_base
<222> LOCATION: (17)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 183
uagggucuca aaaggcuucu u                                              21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-2'-fluoro-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(12)
<223> OTHER INFORMATION: 2'-OMe-nucleotide
<220> FEATURE:
<221> NAME/KEY: modified_base
<222> LOCATION: (17)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 184
uagggucuca aaaggcuucu u                                              21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 185
ccuuuugaga cccugcugun n                                              21

<210> SEQ ID NO 186
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 186
ccuuuugaga cccugcuguu u                                                    21

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 187
ccuuuugaga cccugcuguu u                                                    21

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 188
ccuuuugaga cccugcuguu u                                                    21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 189
ccuuuugaga cccugcuguu u                                                    21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide
```

```
<400> SEQUENCE: 190
ccuuuugaga cccugcuguu u                                              21

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 191
ccuuuugaga cccugcuguu u                                              21

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 192
ccuuuugaga cccugcuguu u                                              21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 193
ccuuuugaga cccugcuguu u                                              21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 194
ccuuuugaga cccugcuguu u                                              21

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 195
ccuuuugaga cccugcuguu u                                              21

<210> SEQ ID NO 196
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 196
ccuuuugaga cccugcuguu u                                              21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 197
acagcagggu cucaaaaggn n                                              21

<210> SEQ ID NO 198
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide
```

<400> SEQUENCE: 198
acagcagggu cucaaaaggu u                                              21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 199
acagcagggu cucaaaaggu u                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 200
acagcagggu cucaaaaggu u                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 201
acagcagggu cucaaaaggu u                                              21

<210> SEQ ID NO 202

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 202
acagcagggu cucaaaaggu u                                             21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 203
acagcagggu cucaaaaggu u                                             21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (3)..(3)
<223> OTHER INFORMATION: 2'-deoxy-nucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (7)..(7)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 204
```
acagcagggu cucaaaaggu u                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (3)..(3)
<223> OTHER INFORMATION: 2'-deoxy-nucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (7)..(7)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 205
acagcagggu cucaaaaggu u                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (4)..(4)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 206
acagcagggu cucaaaaggu u                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 207
acagcagggu cucaaaaggu u                                         21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(8)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 208
acagcagggu cucaaaaggu u                                         21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 209
ggaugacuau gugaaggcan n                                         21
```

<210> SEQ ID NO 210
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 210
ggaugacuau gugaaggcau u                                               21

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 211
ggaugacuau gugaaggcau u                                               21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 212
ggaugacuau gugaaggcau u                                               21

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 213
ggaugacuau gugaaggcau u                                               21

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base -continued

```
<222> LOCATION: (20)..(21)
<223> OTHER INFORMATION: 2'-OMe-nucleotide

<400> SEQUENCE: 214
ggaugacuau gugaaggcau u                                               21

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 215
ggaugacuau gugaaggcau u                                               21

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 216
ggaugacuau gugaaggcau u                                               21

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 217
ggaugacuau gugaaggcau u                                               21

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 218
ggaugacuau gugaaggcau u                                               21

<210> SEQ ID NO 219
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 219
ggaugacuau gugaaggcau u                                            21

<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 220
ggaugacuau gugaaggcau u                                            21

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-deoxy-2'-fluoro-nucleotide
<220> FEATURE:
<221> NAME/KEY: modified_base
<222> LOCATION: (13)..(13)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 221
ggaugacuau gugaaggcau u                                            21

<210> SEQ ID NO 222
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (1)..(2)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 222
ggaugacuau gugaaggcau u                                              21

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 223
ggaugacuau gugaaggcau u                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 224
ugccuucaca uagucauccn n                                              21

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 225
ugccuucaca uagucauccu u                                              21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 226
ugccuucaca uagucauccu u                                                    21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 227
ugccuucaca uagucauccu u                                                    21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 228
ugccuucaca uagucauccu u                                                    21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 229
ugccuucaca uagucauccu u                                              21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 230
ugccuucaca uagucauccu u                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(1)
<223> OTHER INFORMATION: 2'-deoxy-nucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 231
ugccuucaca uagucauccu u                                              21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
```

```
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 232
ugccuucaca uagucauccu u                                              21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 233
ugccuucaca uagucauccu u                                              21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 234
ugccuucaca uagucauccu u                                              21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
```

```
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 235
ugccuucaca uagucauccu u                                              21

<210> SEQ ID NO 236
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 2'-deoxy-2'-fluoro-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 236
ugccuucaca uagucauccu u                                              21

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (13)..(13)
<223> OTHER INFORMATION: 2'-OMe-nucleotide
<220> FEATURE:
<221> NAME/KEY: modified_base
<222> LOCATION: (15)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (19)..(21)
<223> OTHER INFORMATION: 2'-OMe-nucleotide

<400> SEQUENCE: 237
ugccuucaca uagucauccu u                                              21

<210> SEQ ID NO 238
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (13)..(13)
<223> OTHER INFORMATION: 2'-OMe-nucleotide
<220> FEATURE:
<221> NAME/KEY: modified_base
<222> LOCATION: (15)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (19)..(21)
<223> OTHER INFORMATION: 2'-OMe-nucleotide

<400> SEQUENCE: 238
ugccuucaca uagucauccu u                                              21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 239
gaagccuuuu gagacccugn n                                              21

<210> SEQ ID NO 240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 240
gaagccuuuu gagacccugu u                                              21

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 241
```
gaagccuuuu gagacccugu u                                          21

<210> SEQ ID NO 242
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 242
gaagccuuuu gagacccugu u                                          21

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 243
gaagccuuuu gagacccugu u                                          21

<210> SEQ ID NO 244
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 244
gaagccuuuu gagacccugu u                                          21

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 245
gaagccuuuu gagacccugu u                                          21

<210> SEQ ID NO 246
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: modified_base
<222> LOCATION: (20)..(21)
<223> OTHER INFORMATION: 2'-OMe-nucleotide

<400> SEQUENCE: 246
gaagccuuuu gagacccugu u                                            21

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 247
gaagccuuuu gagacccugu u                                            21

<210> SEQ ID NO 248
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 248
gaagccuuuu gagacccugu u                                            21

<210> SEQ ID NO 249
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 249
gaagccuuuu gagacccugu u                                            21

<210> SEQ ID NO 250
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
<223> OTHER INFORMATION: 2'-OMe-nucleotide -continued

```
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 250
gaagccuuuu gagacccugu u                                              21

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 251
cagggucuca aaaggcuucn n                                              21

<210> SEQ ID NO 252
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 252
cagggucuca aaaggcuucu u                                              21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 253
```
cagggucuca aaaggcuucu u                                    21

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 254
cagggucuca aaaggcuucu u                                    21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 255
cagggucuca aaaggcuucu u                                    21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:

```
<221> NAME/KEY: modified_base
<222> LOCATION: (20)..(21)
<223> OTHER INFORMATION: 2'-OMe-nucleotide

<400> SEQUENCE: 256
cagggucuca aaaggcuucu u                                              21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 257
cagggucuca aaaggcuucu u                                              21

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 258
cagggucuca aaaggcuucu u                                              21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 259
cagggucuca aaaggcuucu u                                              21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 260
cagggucuca aaaggcuucu u                                            21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 261
cagggucuca aaaggcuucu u                                            21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)

<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 262
cagggucuca aaaggcuucu u                                              21

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 263
ccucaucuac accaacuaun n                                              21

<210> SEQ ID NO 264
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 264
ccucaucuac accaacuauu u                                              21

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 265
ccucaucuac accaacuauu u                                              21

<210> SEQ ID NO 266
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 266
ccucaucuac accaacuauu u                                      21

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 267
ccucaucuac accaacuauu u                                      21

<210> SEQ ID NO 268
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 268
ccucaucuac accaacuauu u                                      21

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 269
ccucaucuac accaacuauu u                                      21

<210> SEQ ID NO 270
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 270
ccucaucuac accaacuauu u                                      21

<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:

-continued

<221> NAME/KEY: modified_base
<222> LOCATION: (20)..(21)
<223> OTHER INFORMATION: 2'-OMe-nucleotide

<400> SEQUENCE: 271
ccucaucuac accaacuauu u                                             21

<210> SEQ ID NO 272
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 272
ccucaucuac accaacuauu u                                             21

<210> SEQ ID NO 273
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 273
ccucaucuac accaacuauu u                                             21

<210> SEQ ID NO 274
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-OMe-nucleotide
<220> FEATURE:
<221> NAME/KEY: modified_base
<222> LOCATION: (3)..(3)
<223> OTHER INFORMATION: 2'-OMe-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (7)..(7)
<223> OTHER INFORMATION: 2'-OMe-nucleotide
<220> FEATURE:
<221> NAME/KEY: modified_base
<222> LOCATION: (9)..(9)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 274
ccucaucuac accaacuauu u                                             21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: a, c, t, g, u, unknown or other

<400> SEQUENCE: 275
auaguuggug uagaugaggn n                                              21

<210> SEQ ID NO 276
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(21)
<223> OTHER INFORMATION: 2'-OMe-nucleotide

<400> SEQUENCE: 276
auaguuggug uagaugaggu u                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 277
auaguuggug uagaugaggu u                                              21

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)

```
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 278
auaguuggug uagaugaggu u                                              21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 279
auaguuggug uagaugaggu u                                              21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 280
auaguuggug uagaugaggu u                                              21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
```

```
<222> LOCATION: (20)..(21)
<223> OTHER INFORMATION: 2'-OMe-nucleotide

<400> SEQUENCE: 281
auaguuggug uagaugaggu u                                              21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 282
auaguuggug uagaugaggu u                                              21

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (5)..(5)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 283
auaguuggug uagaugaggu u                                              21

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide
```

-continued

```
<400> SEQUENCE: 284
auaguuggug uagaugaggu u                                           21

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 285
auaguuggug uagaugaggu u                                           21

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-deoxy-nucleotide
<220> FEATURE:
<221> NAME/KEY: modified_base
<222> LOCATION: (5)..(6)
<223> OTHER INFORMATION: 2'-deoxy-nucleotide
<220> FEATURE:
<221> NAME/KEY: modified_base
<222> LOCATION: (14)..(14)
<223> OTHER INFORMATION: 2'-OMe-nucleotide
<220> FEATURE:
<221> NAME/KEY: modified_base
<222> LOCATION: (16)..(16)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 286
auaguuggug uagaugaggu u                                           21

<210> SEQ ID NO 287
<211> LENGTH: 986
<212> TYPE: DNA
<213> ORGANISM: Homo sapiens

<400> SEQUENCE: 287
tgggaaagag ggaaaggctt ccccggccag ctgcgcggcg actccgggga ctccagggcg      60
cccctctgcg gccgacgccc ggggtgcagc ggccgccggg gctggggccg gcgggagtcc     120
```

```
gcgggaccct ccagaagagc ggccggcgcc gtgactcagc actggggcgg agcggggcgg        180
gaccacccct ataaggctcg gaggccgcga ggccttcgct ggagtttcgc cgccgcagtc        240
ttcgccacca tgccgcccta caccgtggtc tatttcccag ttcgaggccg ctgcgcggcc        300
ctgcgcatgc tgctggcaga tcagggccag agctggaagg aggaggtggt gaccgtggag        360
acgtggcagg agggctcact caaagcctcc tgcctatacg ggcagctccc caagttccag        420
gacggagacc tcaccctgta ccagtccaat accatcctgc gtcacctggg ccgcacccct        480
gggctctatg gaaggacca gcaggaggca gccctggtgg acatggtgaa tgacggcgtg         540
gaggacctcc gctgcaaata catctccctc atctacacca actatgaggc gggcaaggat        600
gactatgtga aggcactgcc cgggcaactg aagccttttg agaccctgct gtcccagaac        660
cagggaggca agaccttcat tgtgggagac cagatctcct tcgctgacta caacctgctg        720
gacttgctgc tgatccatga ggtcctagcc cctggctgcc tggatgcgtt ccccctgctc        780
tcagcatatg tggggcgcct cagtgccgg cccaagctca aggccttcct ggcctcccct         840
gagtacgtga acctccccat caatggcaac gggaaacagt gagggttggg gggactctga        900
gcgggaggca gagtttgcct tcctttctcc aggaccaata aaatttctaa gagagctaaa        960
aaaaaaaaaa aaaaaaaaa aaaaaa                                             986
```

<210> SEQ ID NO 288
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288

```
ctcgaggggc aactgaagcc ttttgagacc ctgctgtccc aggcggccgc                    50
```

<210> SEQ ID NO 289
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289

```
ctcgagctgg acagcaggg tctcaaaagg cttcagttgc ccgcggccgc                     50
```

<210> SEQ ID NO 290
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290

```
ctcgaggggc aactctacgc aaaacagacc ctgctgtccc aggcggccgc                    50
```

<210> SEQ ID NO 291
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
ctcgaggggc aactctacgc aaaacagacc ctgctctacg caaaacagac cctgctgtcc      60
caggcggccg c                                                          71

<210> SEQ ID NO 292
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
ctcgaggggc aactctacgc aaaacagacc ctgctctacg caaaacagac cctgctctac      60
gcaaaacaga ccctgctgtc caggcggcc gc                                    92

<210> SEQ ID NO 293
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293
ctcgaggggc aactctacgc aaaacagacc ctgctctacg caaaacagac cctgctctac      60
gcaaaacaga ccctgctcta cgcaaaacag accctgctgt cccaggcggc cgc            113

<210> SEQ ID NO 294
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (13)..(14)
<223> OTHER INFORMATION: 2'-OMe-nucleotide
<220> FEATURE:

```
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 294
ccuuuugaga cccugcuguu u                                              21

<210> SEQ ID NO 295
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 295
ccuuuugaga cccugcuguu u                                              21

<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (13)..(14)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 296
ccuuuugaga cccugcuguu u                                              21

<210> SEQ ID NO 297
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (1)..(3)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (13)..(14)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 297
ccuuuugaga cccugcuguu u                                              21

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 298
acagcagggu cucaaaaggu u                                              21

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (4)..(4)
<223> OTHER INFORMATION: 2'-deoxy-nucleotide
```

```
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (13)..(13)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 299
acagcagggu cucaaaaggu u                                              21

<210> SEQ ID NO 300
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (4)..(4)
<223> OTHER INFORMATION: 2'-deoxy-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (13)..(13)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 300
acagcagggu cucaaaaggu u                                              21

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide
<220> FEATURE:
<221> NAME/KEY: modified_base
<222> LOCATION: (2)..(2)
<223> OTHER INFORMATION: 2'-OMe-nucleotide
<220> FEATURE:
<221> NAME/KEY: modified_base
<222> LOCATION: (4)..(4)
<223> OTHER INFORMATION: 2'-deoxy-nucleotide
<220> FEATURE:
<221> NAME/KEY: modified_base
<222> LOCATION: (5)..(5)
<223> OTHER INFORMATION: 2'-OMe-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (13)..(13)
<223> OTHER INFORMATION: 2'-OMe-nucleotide
<220> FEATURE:
<221> NAME/KEY: modified_base
<222> LOCATION: (15)..(15)
<223> OTHER INFORMATION: 2'-OMe-nucleotide
<220> FEATURE:
<221> NAME/KEY: modified_base
<222> LOCATION: (17)..(17)
<223> OTHER INFORMATION: 2'-OMe-nucleotide
<220> FEATURE:
<221> NAME/KEY: modified_base
<222> LOCATION: (19)..(21)
<223> OTHER INFORMATION: 2'-OMe-nucleotide

<400> SEQUENCE: 301
acagcagggu cucaaaaggu u                                       21

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-OMe-nucleotide
<220> FEATURE:
<221> NAME/KEY: modified_base
<222> LOCATION: (11)..(11)
<223> OTHER INFORMATION: 2'-OMe-nucleotide
<220> FEATURE:
<221> NAME/KEY: modified_base
<222> LOCATION: (13)..(13)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 302
ggaugacuau gugaaggcau u                                       21

<210> SEQ ID NO 303
<211> LENGTH: 21
<212> TYPE: RNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 2'-OMe-nucleotide
<220> FEATURE:
<221> NAME/KEY: modified_base
<222> LOCATION: (4)..(4)
<223> OTHER INFORMATION: 2'-OMe-nucleotide
<220> FEATURE:
<221> NAME/KEY: modified_base
<222> LOCATION: (8)..(8)
<223> OTHER INFORMATION: 2'-OMe-nucleotide
<220> FEATURE:
<221> NAME/KEY: modified_base
<222> LOCATION: (10)..(10)
<223> OTHER INFORMATION: 2'-OMe-nucleotide
<220> FEATURE:
<221> NAME/KEY: modified_base
<222> LOCATION: (12)..(12)
<223> OTHER INFORMATION: 2'-OMe-nucleotide
<220> FEATURE:
<221> NAME/KEY: modified_base
<222> LOCATION: (18)..(18)
<223> OTHER INFORMATION: 2'-OMe-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 303
ggaugacuau gugaaggcau u                                              21

<210> SEQ ID NO 304
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (4)..(4)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 304
ugccuucaca uagucauccu u                                              21

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

```
    Synthetic oligonucleotide
<220> FEATURE:
<221> NAME/KEY: modified_base
<222> LOCATION: (4)..(4)
<223> OTHER INFORMATION: 2'-deoxy-nucleotide
<220> FEATURE:
<221> NAME/KEY: modified_base
<222> LOCATION: (6)..(6)
<223> OTHER INFORMATION: 2'-deoxy-nucleotide
<220> FEATURE:
<221> NAME/KEY: modified_base
<222> LOCATION: (8)..(8)
<223> OTHER INFORMATION: 2'-deoxy-nucleotide
<220> FEATURE:
<221> NAME/KEY: modified_base
<222> LOCATION: (20)..(21)
<223> OTHER INFORMATION: 2'-OMe-nucleotide

<400> SEQUENCE: 305
ugccuucaca uagucauccu u                                              21
```